(12) United States Patent
    Kavazov et al.

(10) Patent No.: US 8,613,725 B2
(45) Date of Patent: Dec. 24, 2013

(54) RESERVOIR SYSTEMS AND METHODS

(75) Inventors: Julian D. Kavazov, Arcadia, CA (US);
    Ian B. Hanson, Granada Hills, CA (US);
    Colin A. Chong, Burbank, CA (US);
    Eric M. Lorenzen, Granada Hills, CA (US);
    Rafael Bikovsky, Oak Park, CA (US);
    Truong Gia Luan, Winnetka, CA (US);
    Mike Teang Lee, Burbank, CA (US);
    Thomas P. Miller, Porter Ranch, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 29 days.

(21) Appl. No.: 13/083,512

(22) Filed: Apr. 8, 2011

(65) Prior Publication Data
    US 2011/0190700 A1    Aug. 4, 2011

Related U.S. Application Data

(63) Continuation-in-part of application No. 11/964,649, filed on Dec. 26, 2007, now Pat. No. 8,083,716.

(60) Provisional application No. 60/927,032, filed on Apr. 30, 2007.

(51) Int. Cl.
    *A61M 1/00*    (2006.01)

(52) U.S. Cl.
    USPC ............ 604/123; 601/122; 601/151; 601/152

(58) Field of Classification Search
    USPC .................. 604/221, 222, 151–155, 121–127
    See application file for complete search history.

(56) References Cited

U.S. PATENT DOCUMENTS

| 1,948,982 | A | 2/1934 | Cutter |
| 2,064,815 | A | 12/1936 | Armstrong |

(Continued)

FOREIGN PATENT DOCUMENTS

| DE | 10 2004 055 870 A1 | 5/2006 |
| DE | 20 2007 006 363 U1 | 8/2007 |

(Continued)

OTHER PUBLICATIONS

International Search Report and Written Opinion for related PCT Application No. PCT/US2007/076641 dated Feb. 27, 2008.

(Continued)

*Primary Examiner* — Theodore Stigell
*Assistant Examiner* — Leah Stohr
(74) *Attorney, Agent, or Firm* — Foley & Lardner LLP

(57) ABSTRACT

A reservoir includes a reservoir body portion and a collecting portion. The reservoir body portion having a wall defining an interior volume for containing fluidic media, the reservoir having a first port in the reservoir body portion to be in fluid flow communication with the interior volume, the first port for expelling fluidic media from the interior volume as a plunger is moved within the reservoir. The collecting portion having a wall defining a volume in fluid flow communication with the interior volume, the volume of the collecting portion for collecting gas bubbles in the fluidic media as the fluidic media is expelled through the first port from the interior volume of the reservoir body portion, the reservoir having a second port in the collecting portion to be in fluid flow communication with the volume of the collecting portion, the second port for receiving fluidic media into the reservoir.

47 Claims, 27 Drawing Sheets

(56) References Cited

U.S. PATENT DOCUMENTS

| | | |
|---|---|---|
| 2,570,625 A | 10/1951 | Zimmerman et al. |
| 2,644,450 A | 7/1953 | Krewson |
| RE24,918 E | 1/1961 | Mills |
| 2,973,758 A | 3/1961 | Murrish |
| 3,223,289 A | 12/1965 | Bouet |
| 3,342,180 A | 9/1967 | Ellsworth et al. |
| 3,343,422 A | 9/1967 | McSmith |
| 3,572,552 A | 3/1971 | Guinn |
| 3,623,474 A | 11/1971 | Heilman et al. |
| 3,650,093 A | 3/1972 | Rosenberg |
| 3,662,753 A | 5/1972 | Tassell |
| 3,729,032 A | 4/1973 | Tischlinger et al. |
| 3,802,430 A | 4/1974 | Schwebel et al. |
| 3,963,151 A | 6/1976 | North, Jr. |
| 3,993,061 A * | 11/1976 | O'Leary ............... 604/152 |
| 4,064,879 A | 12/1977 | Leibinsohn |
| 4,089,624 A | 5/1978 | Nichols et al. |
| 4,117,841 A | 10/1978 | Perrotta et al. |
| 4,215,701 A | 8/1980 | Raitto |
| 4,219,055 A | 8/1980 | Wright |
| 4,234,108 A | 11/1980 | Diamond |
| 4,373,535 A | 2/1983 | Martell |
| 4,392,850 A | 7/1983 | Elias et al. |
| 4,434,820 A | 3/1984 | Glass |
| 4,448,206 A | 5/1984 | Martell |
| 4,493,704 A | 1/1985 | Beard et al. |
| 4,568,336 A | 2/1986 | Cooper |
| 4,572,210 A | 2/1986 | McKinnon |
| 4,585,435 A | 4/1986 | Vaillancourt |
| 4,684,365 A | 8/1987 | Reinicke |
| 4,684,366 A | 8/1987 | Denny et al. |
| 4,703,763 A | 11/1987 | McAlister et al. |
| 4,743,249 A | 5/1988 | Loveland |
| 4,744,955 A | 5/1988 | Shapiro |
| 4,759,756 A | 7/1988 | Forman et al. |
| 4,838,857 A | 6/1989 | Strowe et al. |
| 4,865,592 A | 9/1989 | Rycroft |
| 4,883,101 A | 11/1989 | Strong |
| 4,913,703 A | 4/1990 | Pasqualucci et al. |
| 4,957,637 A | 9/1990 | Cornell |
| 4,976,696 A | 12/1990 | Sanderson et al. |
| 4,986,820 A | 1/1991 | Fischer |
| 4,994,034 A | 2/1991 | Botich et al. |
| 5,002,527 A | 3/1991 | Reller et al. |
| 5,045,096 A | 9/1991 | Quang et al. |
| 5,049,129 A | 9/1991 | Zdeb et al. |
| 5,053,001 A | 10/1991 | Reller et al. |
| 5,062,834 A | 11/1991 | Gross et al. |
| 5,090,963 A | 2/1992 | Gross et al. |
| 5,115,948 A | 5/1992 | Johnson |
| 5,156,591 A | 10/1992 | Gross et al. |
| 5,176,502 A | 1/1993 | Sanderson et al. |
| 5,186,805 A | 2/1993 | Gross et al. |
| 5,190,522 A | 3/1993 | Wojcicki et al. |
| 5,203,506 A | 4/1993 | Gross et al. |
| 5,232,449 A | 8/1993 | Stern et al. |
| 5,242,406 A | 9/1993 | Gross et al. |
| 5,242,408 A | 9/1993 | Jhuboo et al. |
| 5,246,147 A | 9/1993 | Gross |
| 5,254,096 A | 10/1993 | Rondelet et al. |
| 5,259,732 A | 11/1993 | Stern |
| 5,261,884 A | 11/1993 | Stern et al. |
| 5,275,582 A | 1/1994 | Wimmer |
| 5,284,570 A | 2/1994 | Savage et al. |
| 5,292,318 A | 3/1994 | Haber et al. |
| 5,295,966 A | 3/1994 | Stern et al. |
| 5,295,967 A | 3/1994 | Rondelet et al. |
| 5,308,333 A | 5/1994 | Skakoon |
| 5,312,364 A | 5/1994 | Jacobs |
| 5,356,632 A | 10/1994 | Gross et al. |
| 5,367,891 A | 11/1994 | Furuyama |
| 5,385,559 A | 1/1995 | Mannix |
| 5,387,450 A | 2/1995 | Stewart |
| 5,407,434 A | 4/1995 | Gross |
| 5,409,236 A | 4/1995 | Therrien |
| 5,425,706 A | 6/1995 | Gross et al. |
| 5,496,285 A | 3/1996 | Schumacher et al. |
| 5,527,288 A | 6/1996 | Gross et al. |
| 5,533,964 A | 7/1996 | Halperin et al. |
| 5,697,916 A | 12/1997 | Schraga |
| 5,704,520 A | 1/1998 | Gross |
| 5,800,420 A | 9/1998 | Gross et al. |
| 5,807,375 A | 9/1998 | Gross et al. |
| 5,820,622 A | 10/1998 | Gross et al. |
| 5,848,991 A | 12/1998 | Gross et al. |
| 5,851,549 A | 12/1998 | Svec |
| 5,858,001 A | 1/1999 | Tsals et al. |
| 5,865,803 A | 2/1999 | Major |
| 5,871,125 A | 2/1999 | Gross |
| 5,887,752 A | 3/1999 | Strother |
| 5,933,287 A | 8/1999 | Muller |
| 5,951,523 A | 9/1999 | Osterlind et al. |
| 5,954,697 A | 9/1999 | Srisathapat et al. |
| 5,957,889 A | 9/1999 | Poulsen et al. |
| 5,984,894 A | 11/1999 | Poulsen et al. |
| 5,997,501 A | 12/1999 | Gross et al. |
| 6,003,736 A | 12/1999 | Ljunggren |
| 6,033,377 A | 3/2000 | Rasmussen et al. |
| 6,067,906 A | 5/2000 | Ryan et al. |
| 6,088,608 A | 7/2000 | Schulman et al. |
| 6,099,504 A | 8/2000 | Gross et al. |
| 6,117,107 A * | 9/2000 | Chen ............... 604/110 |
| 6,119,028 A | 9/2000 | Schulman et al. |
| 6,126,643 A | 10/2000 | Vaillancouert |
| 6,186,982 B1 | 2/2001 | Gross et al. |
| 6,229,584 B1 | 5/2001 | Chuo et al. |
| 6,242,665 B1 | 6/2001 | Malowaniec |
| 6,248,093 B1 | 6/2001 | Moberg |
| 6,261,272 B1 | 7/2001 | Gross et al. |
| 6,275,717 B1 | 8/2001 | Gross et al. |
| 6,277,095 B1 | 8/2001 | Kriesel et al. |
| 6,312,409 B1 | 11/2001 | Gross |
| 6,314,317 B1 | 11/2001 | Willis |
| 6,346,095 B1 | 2/2002 | Gross et al. |
| 6,364,865 B1 | 4/2002 | Lavi et al. |
| 6,375,047 B1 | 4/2002 | Herda et al. |
| 6,406,455 B1 | 6/2002 | Willis et al. |
| 6,423,035 B1 | 7/2002 | Das et al. |
| 6,440,096 B1 | 8/2002 | Lastovich et al. |
| 6,450,993 B1 | 9/2002 | Lin |
| 6,461,329 B1 | 10/2002 | Van Antwerp et al. |
| 6,474,219 B2 | 11/2002 | Klitmose et al. |
| 6,474,375 B2 | 11/2002 | Spero et al. |
| 6,478,771 B1 | 11/2002 | Lavi et al. |
| 6,485,461 B1 | 11/2002 | Mason et al. |
| 6,485,465 B2 | 11/2002 | Moberg et al. |
| 6,490,483 B2 | 12/2002 | Willis |
| 6,503,225 B1 | 1/2003 | Kirsch et al. |
| 6,508,788 B2 | 1/2003 | Preuthun |
| 6,537,251 B2 | 3/2003 | Klitmose |
| 6,551,285 B1 | 4/2003 | Bierman |
| 6,572,600 B1 | 6/2003 | Roe et al. |
| 6,585,707 B2 | 7/2003 | Cabiri et al. |
| 6,589,229 B1 | 7/2003 | Connelly et al. |
| 6,595,956 B1 | 7/2003 | Gross et al. |
| 6,607,509 B2 | 8/2003 | Bobroff et al. |
| 6,607,513 B1 | 8/2003 | Down et al. |
| 6,613,019 B2 | 9/2003 | Munk |
| 6,616,627 B2 | 9/2003 | Willis et al. |
| 6,626,874 B1 | 9/2003 | Duchamp |
| 6,641,565 B1 | 11/2003 | Lavi et al. |
| 6,641,566 B2 | 11/2003 | Douglas et al. |
| 6,645,181 B1 | 11/2003 | Lavi et al. |
| 6,656,147 B1 | 12/2003 | Gertsek et al. |
| 6,656,158 B2 | 12/2003 | Mahoney et al. |
| 6,656,159 B2 | 12/2003 | Flaherty |
| 6,669,669 B2 | 12/2003 | Flaherty et al. |
| 6,689,100 B2 | 2/2004 | Connelly et al. |
| 6,692,457 B2 | 2/2004 | Flaherty |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,195 B2 | 4/2004 | Nolan, Jr. et al. |
| 6,719,734 B1 | 4/2004 | Harkless |

(56) References Cited

U.S. PATENT DOCUMENTS

| | | |
|---|---|---|
| 6,723,068 B2 | 4/2004 | Lavi et al. |
| 6,723,072 B2 | 4/2004 | Flaherty et al. |
| 6,740,059 B2 | 5/2004 | Flaherty |
| 6,740,072 B2 | 5/2004 | Starkweather et al. |
| 6,749,587 B2 | 6/2004 | Flaherty |
| 6,767,188 B2 | 7/2004 | Vrane et al. |
| 6,768,425 B2 | 7/2004 | Flaherty et al. |
| 6,786,246 B2 | 9/2004 | Ohms et al. |
| 6,796,965 B2 | 9/2004 | Dumaresq-Lucas et al. |
| 6,808,506 B2 | 10/2004 | Lastovich et al. |
| 6,827,702 B2 | 12/2004 | Lebel et al. |
| 6,830,558 B2 | 12/2004 | Flaherty et al. |
| 6,830,560 B1 | 12/2004 | Gross et al. |
| 6,886,724 B2 | 5/2005 | Hung |
| 6,899,699 B2 | 5/2005 | Enggaard |
| 6,915,147 B2 | 7/2005 | Lebel et al. |
| 6,918,887 B1 | 7/2005 | Gremel et al. |
| 6,936,006 B2 | 8/2005 | Sabra |
| 6,939,324 B2 | 9/2005 | Gonnelli et al. |
| 6,948,522 B2 | 9/2005 | Newbrough et al. |
| 6,948,918 B2 | 9/2005 | Hansen |
| 6,952,604 B2 | 10/2005 | DeNuzzio et al. |
| 6,960,184 B2 | 11/2005 | Willis et al. |
| 6,960,192 B1 | 11/2005 | Flaherty et al. |
| 6,997,911 B2 | 2/2006 | Klitmose |
| 7,008,399 B2 | 3/2006 | Larsen et al. |
| 7,018,360 B2 | 3/2006 | Flaherty et al. |
| 7,027,478 B2 | 4/2006 | Ackley |
| 7,029,455 B2 | 4/2006 | Flaherty |
| 7,083,592 B2 | 8/2006 | Lastovich et al. |
| 7,083,599 B2 | 8/2006 | Alchas et al. |
| 7,115,108 B2 | 10/2006 | Wilkinson et al. |
| 7,128,727 B2 | 10/2006 | Flaherty et al. |
| 7,133,329 B2 | 11/2006 | Skyggebjerg et al. |
| 7,137,964 B2 | 11/2006 | Flaherty |
| 7,144,384 B2 | 12/2006 | Gorman et al. |
| 7,150,409 B2 | 12/2006 | Gonnelli et al. |
| 7,156,838 B2 | 1/2007 | Gabel et al. |
| 7,187,969 B2 | 3/2007 | Willis |
| 7,220,245 B2 | 5/2007 | Kriesel |
| 7,220,889 B2 | 5/2007 | Sigurjonsson et al. |
| 7,318,816 B2 | 1/2008 | Bobroff et al. |
| 7,323,142 B2 | 1/2008 | Pendo et al. |
| 7,390,294 B2 | 6/2008 | Hassler, Jr. |
| 7,399,484 B2 | 7/2008 | Ellefson et al. |
| 7,621,429 B2 | 11/2009 | Wu et al. |
| 7,686,787 B2 | 3/2010 | Moberg et al. |
| 7,858,112 B2 | 12/2010 | Hatanaka et al. |
| 7,981,085 B2 | 7/2011 | Ethelfeld |
| 8,409,143 B2 | 4/2013 | Lanigan et al. |
| 2001/0041869 A1 | 11/2001 | Causey, III et al. |
| 2002/0040208 A1 | 4/2002 | Flaherty et al. |
| 2002/0072733 A1 | 6/2002 | Flaherty |
| 2002/0104584 A1 | 8/2002 | Spero et al. |
| 2002/0123740 A1 | 9/2002 | Flaherty et al. |
| 2002/0126036 A1 | 9/2002 | Flaherty et al. |
| 2002/0169439 A1 | 11/2002 | Flaherty |
| 2003/0023206 A1* | 1/2003 | Bausmith et al. ............ 604/122 |
| 2003/0055380 A1 | 3/2003 | Flaherty |
| 2003/0073952 A1 | 4/2003 | Flaherty et al. |
| 2003/0097092 A1 | 5/2003 | Flaherty |
| 2003/0104032 A1 | 6/2003 | Sawhney et al. |
| 2003/0125672 A1 | 7/2003 | Adair et al. |
| 2003/0167035 A1 | 9/2003 | Flaherty et al. |
| 2003/0167036 A1 | 9/2003 | Flaherty |
| 2003/0199824 A1 | 10/2003 | Mahoney et al. |
| 2003/0199825 A1 | 10/2003 | Flaherty |
| 2003/0212364 A1 | 11/2003 | Mann et al. |
| 2003/0229310 A1 | 12/2003 | Flaherty et al. |
| 2003/0233069 A1 | 12/2003 | Gillespie et al. |
| 2004/0002682 A1 | 1/2004 | Kovelman et al. |
| 2004/0010207 A1 | 1/2004 | Flaherty et al. |
| 2004/0011866 A1 | 1/2004 | Saad |
| 2004/0015131 A1 | 1/2004 | Flaherty et al. |
| 2004/0064088 A1 | 4/2004 | Gorman et al. |
| 2004/0064096 A1 | 4/2004 | Flaherty et al. |
| 2004/0073095 A1 | 4/2004 | Causey, III et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0116866 A1 | 6/2004 | Gorman et al. |
| 2004/0140327 A1 | 7/2004 | Osborne et al. |
| 2004/0158207 A1 | 8/2004 | Hunn et al. |
| 2004/0199140 A1 | 10/2004 | Rue et al. |
| 2004/0204673 A1 | 10/2004 | Flaherty et al. |
| 2004/0220551 A1 | 11/2004 | Flaherty et al. |
| 2004/0235446 A1 | 11/2004 | Flaherty et al. |
| 2004/0236201 A1 | 11/2004 | Lebel et al. |
| 2004/0260233 A1 | 12/2004 | Garibotto et al. |
| 2005/0022274 A1 | 1/2005 | Campbell et al. |
| 2005/0065760 A1 | 3/2005 | Murtfeldt et al. |
| 2005/0101920 A1 | 5/2005 | Keane et al. |
| 2005/0119618 A1 | 6/2005 | Gonnelli |
| 2005/0137530 A1 | 6/2005 | Campbell et al. |
| 2006/0184119 A1 | 8/2006 | Remde et al. |
| 2006/0253085 A1 | 11/2006 | Geismar et al. |
| 2006/0264835 A1 | 11/2006 | Nielsen et al. |
| 2006/0264894 A1 | 11/2006 | Moberg et al. |
| 2007/0062068 A1 | 3/2007 | Li |
| 2007/0066939 A1 | 3/2007 | Krulevich et al. |
| 2007/0073235 A1 | 3/2007 | Estes et al. |
| 2007/0293826 A1 | 12/2007 | Wall et al. |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051710 A1 | 2/2008 | Moberg et al. |
| 2008/0051711 A1 | 2/2008 | Mounce et al. |
| 2008/0051714 A1 | 2/2008 | Moberg et al. |
| 2008/0051716 A1 | 2/2008 | Stutz |
| 2008/0051718 A1 | 2/2008 | Kavazov et al. |
| 2008/0051727 A1 | 2/2008 | Moberg et al. |
| 2008/0051730 A1 | 2/2008 | Bikovsky |
| 2008/0051738 A1 | 2/2008 | Griffin |
| 2008/0051765 A1 | 2/2008 | Mounce |
| 2008/0077081 A1 | 3/2008 | Mounce et al. |
| 2008/0097291 A1 | 4/2008 | Hanson et al. |
| 2008/0097321 A1 | 4/2008 | Mounce et al. |
| 2008/0097326 A1 | 4/2008 | Moberg et al. |
| 2008/0097327 A1 | 4/2008 | Bente et al. |
| 2008/0097328 A1 | 4/2008 | Moberg et al. |
| 2008/0097375 A1 | 4/2008 | Bikovsky |
| 2008/0097381 A1 | 4/2008 | Moberg et al. |
| 2008/0257916 A1 | 10/2008 | Chang |
| 2008/0269682 A1 | 10/2008 | Kavazov et al. |
| 2009/0206111 A1 | 8/2009 | Conrardy et al. |

FOREIGN PATENT DOCUMENTS

| | | |
|---|---|---|
| EP | 1 462 134 A1 | 9/2004 |
| EP | 1 527 792 A1 | 5/2005 |
| EP | 1 347 705 | 12/2005 |
| EP | 1 423 079 | 7/2006 |
| EP | 1 135 056 | 8/2006 |
| EP | 1 545 657 | 11/2006 |
| EP | 1 546 556 | 12/2006 |
| EP | 1 341 569 | 1/2007 |
| EP | 1 461 070 | 1/2007 |
| EP | 1 464 351 | 1/2007 |
| EP | 1 309 366 | 2/2007 |
| EP | 0 944 648 | 3/2007 |
| EP | 1 646 412 | 3/2007 |
| EP | 1 095 668 | 4/2007 |
| EP | 1 702 635 | 1/2008 |
| FR | 1.496.026 | 9/1967 |
| GB | 1 452 104 | 10/1976 |
| GB | 2 176 711 A | 1/1987 |
| GB | 2 207 652 A | 2/1989 |
| WO | WO 95/32015 | 11/1995 |
| WO | WO 96/26702 | 9/1996 |
| WO | WO 97/44078 | 11/1997 |
| WO | WO 97/46203 | 12/1997 |
| WO | WO 99/48546 | 9/1999 |
| WO | WO-99/59665 | 11/1999 |
| WO | WO-00/47254 | 8/2000 |

(56) References Cited

FOREIGN PATENT DOCUMENTS

| | | |
|---|---|---|
| WO | WO 00/69488 | 11/2000 |
| WO | WO 01/70307 | 9/2001 |
| WO | WO-01/76684 A1 | 10/2001 |
| WO | WO 02/02165 A2 | 1/2002 |
| WO | WO-02/20073 A2 | 3/2002 |
| WO | WO-02/28454 A2 | 4/2002 |
| WO | WO-02/40083 A2 | 5/2002 |
| WO | WO-02/49509 A2 | 6/2002 |
| WO | WO-02/068015 A2 | 9/2002 |
| WO | WO-03/006090 A1 | 1/2003 |
| WO | WO-03/024504 A2 | 3/2003 |
| WO | WO 03/026728 | 4/2003 |
| WO | WO-03/033051 A1 | 4/2003 |
| WO | WO-03/059372 A3 | 7/2003 |
| WO | WO 03/072172 A2 | 9/2003 |
| WO | WO-03/074121 A1 | 9/2003 |
| WO | WO-03/090509 A2 | 11/2003 |
| WO | WO-03/090819 A2 | 11/2003 |
| WO | WO-03/090838 A1 | 11/2003 |
| WO | WO-03/103758 A1 | 12/2003 |
| WO | WO-03/103763 A1 | 12/2003 |
| WO | WO 2004/006981 A2 | 1/2004 |
| WO | WO-2004/006982 A2 | 1/2004 |
| WO | WO 2004/030716 | 4/2004 |
| WO | WO 2004/030717 | 4/2004 |
| WO | WO-2004/047641 A2 | 6/2004 |
| WO | WO-2004/060436 A2 | 7/2004 |
| WO | WO-2004/093648 A2 | 11/2004 |
| WO | WO-2004/098390 A2 | 11/2004 |
| WO | WO-2004/098454 A2 | 11/2004 |
| WO | WO 2004/098683 A1 | 11/2004 |
| WO | WO 2004/110526 A1 | 12/2004 |
| WO | WO 2005/000382 A2 | 1/2005 |
| WO | WO 2005/072795 A2 | 8/2005 |
| WO | WO-2005/094920 A1 | 10/2005 |
| WO | WO 2005/097237 A1 | 10/2005 |
| WO | WO-2006/015922 A1 | 2/2006 |
| WO | WO-2006/018425 A3 | 2/2006 |
| WO | WO-2006/018447 A3 | 2/2006 |
| WO | WO-2006/024671 A1 | 3/2006 |
| WO | WO-2006/024672 A1 | 3/2006 |
| WO | WO-2006/032692 A1 | 3/2006 |
| WO | WO-2006/042811 A3 | 4/2006 |
| WO | WO 2006/058435 A2 | 6/2006 |
| WO | WO-2006/072416 A2 | 7/2006 |
| WO | WO-2006/075016 A1 | 7/2006 |
| WO | WO-2006/077262 A1 | 7/2006 |
| WO | WO-2006/077263 A1 | 7/2006 |
| WO | WO-2006/084464 A1 | 8/2006 |
| WO | WO-2006/086980 A1 | 8/2006 |
| WO | WO-2006/089547 A1 | 8/2006 |
| WO | WO-2006/089548 A1 | 8/2006 |
| WO | WO-2006/089965 A1 | 8/2006 |
| WO | WO-2006/096746 A1 | 9/2006 |
| WO | WO-2006/097453 A1 | 9/2006 |
| WO | WO-2006/104806 A2 | 10/2006 |
| WO | WO-2006/108775 A2 | 10/2006 |
| WO | WO-2006/108809 A1 | 10/2006 |
| WO | WO-2006/116997 A1 | 11/2006 |
| WO | WO-2006/120253 A2 | 11/2006 |
| WO | WO-2006/125692 A1 | 11/2006 |
| WO | WO-2007/000425 A2 | 1/2007 |
| WO | WO-2007/000426 A2 | 1/2007 |
| WO | WO-2007/000427 A1 | 1/2007 |
| WO | WO-2007/038091 A2 | 4/2007 |
| WO | WO 2007062068 A2 | 5/2007 |
| WO | WO-2007/071255 A1 | 6/2007 |
| WO | WO-2007/076641 A1 | 7/2007 |
| WO | PCT/US2007/76641 | 8/2007 |
| WO | WO-2007/087808 A1 | 8/2007 |
| WO | WO 2007/130809 A2 | 11/2007 |
| WO | WO 2008/024614 A2 | 2/2008 |
| WO | WO 2008/093063 A2 | 8/2008 |
| WO | WO 2008/151241 A2 | 12/2008 |

OTHER PUBLICATIONS

Office Action dated Jan. 7, 2010 from related U.S. Appl. No. 11/964,649.
Office Action dated Jul. 8, 2009 from related U.S. Appl. No. 11/964,649.
US Office Action dated Mar. 29, 2011 from related U.S. Appl. No. 11/964,649.
International Search Report and Written Opinion for PCT patent application No. PCT/US2007/076474 dated Feb. 29, 2008.
Notice of Allowance dated Jan. 19, 2010 from related U.S. Appl. No. 11/759,725.
Office Action dated Feb. 17, 2010 from related U.S. Appl. No. 11/604,172.
Office Action dated Jan. 14, 2010 from related U.S. Appl. No. 12/411,247.
Office Action dated Mar. 2, 2010 from related U.S. Appl. No. 11/588,832.
Office Action dated Mar. 4, 2010 from related U.S. Appl. No. 12/099,738.
Office Action dated Nov. 19, 2008 from related U.S. Appl. No. 11/515,225.
Office Action dated Nov. 21, 2008 from related patent U.S. Appl. No. 11/588,832.
Office Action dated Nov. 21, 2008 from related patent U.S. Appl. No. 11/604,171.
Office Action dated Oct. 19, 2009 from related U.S. Appl. No. 11/515,225.
Office Action dated Oct. 9, 2009 from related U.S. Appl. No. 11/604,171.
Search Report dated Jan. 11, 2010 from related European patent application No. 07841183.2.
Office Action dated Dec. 22, 2010 from related U.S. Appl. No. 12/111,815.
Office Action dated Dec. 30, 2010 from related U.S. Appl. No. 12/107,580.
Office Action dated Dec. 9, 2010 from related U.S. Appl. No. 12/099,738.
US Office Action dated Oct. 15, 2010 from related U.S. Appl. No. 12/027,963.
US Office Action dated Aug. 18, 2010 from related U.S. Appl. No. 12/107,580.
International Search Report and Written Opinion for PCT application No. PCT/US2008/082193 dated Jun. 29, 2010.
Office Action dated Jul. 21, 2010 from related U.S. Appl. No. 12/099,738.
Office Action dated Jun. 16, 2010 from related U.S. Appl. No. 12/027,963.
U.S. Office Action dated Mar. 8, 2011 from related U.S. Appl. No. 12/411,247.
US Notice of Allowance dated Mar. 3, 2011 from related U.S. Appl. No. 12/107,580.
US Office Action dated Feb. 23, 2011 from related U.S. Appl. No. 12/411,236.
US Office Action dated Oct. 1, 2010 U.S. Appl. No. 12/411,247.
US Office Action dated Sep. 28, 2010 from related U.S. Appl. No. 12/411,236.
PCT Search Report Dated Jun. 5, 2009 from related PCT application No. PCT/US2008/082187.
Office Action dated Apr. 30, 2009 from related U.S. Appl. No. 12/027,963.
Office Action dated Jul. 10, 2009 from related U.S. Appl. No. 12/411,236.
Office Action dated Aug. 4, 2009 from related U.S. Appl. No. 12/411,247.
Final Office Action dated Jun. 17, 2009 from U.S. Appl. No. 11/604,172.
Notice of Allowance dated Jun. 23, 2009 from related U.S. Appl. No. 11/759,725.
Final Office Action dated Sep. 24, 2009 from related U.S. Appl. No. 12/027,963.
Final Office Action dated Oct. 23, 2009 from U.S. Appl. No. 12/411,236.

(56) References Cited

OTHER PUBLICATIONS

Non-Final Office Action dated Nov. 10, 2009 from related U.S. Appl. No. 12/099,738.
PCT search report dated Feb. 3, 2009 from PCT Application No. PCT/US2008/082185.
Partial PCT Search Report (Invitation to Pay Additional Fees) dated Feb. 2, 2009 for related PCT application No. PCT/US2008/082186.
Partial PCT Search Report dated Mar. 5, 2009 from related PCT application No. PCT/US2008/082187.
PCT Search Report dated Apr. 28, 2009 from related PCT application No. PCT/US2008/082186.
Office Action dated Jan. 29, 2009 from related patent U.S. Appl. No. 11/604,172.
Office Action dated Nov. 24, 2008 from related U.S. Appl. No. 11/759,725.
Office Action dated Apr. 13, 2009 from related U.S. Appl. No. 11/604,171.
Office Action dated Apr. 9, 2009 from related U.S. Appl. No. 11/515,225.
PCT Search Report dated May 15, 2008 for PCT application No. PCT/US2007/076679.
US Notice of Allowance dated Jul. 27, 2011 from related U.S. Appl. No. 12/411,247.
US Office Action from related U.S. Appl. No. 12/111,751, mailed Nov. 21, 2012, 13 pages.
US Office Action from related U.S. Appl. No. 12/099,738, mailed Dec. 20, 2012, 27 pages.
U.S. Notice of Allowance dated Apr. 29, 2013 from related U.S. Appl. No. 12/497,345.
U.S. Notice of Allowance dated May 8, 2013 from related U.S. Appl. No. 11/515,225.
U.S. Notice of Allowance from related U.S. Appl. No. 12/111,751, mailed Mar. 4, 2013.
U.S. Notice of Allowance dated Aug. 8, 2013 from related U.S. Appl. No. 13/163,548.
U.S. Notice of Allowance dated Aug. 21, 2013 from related U.S. Appl. No. 12/099,738.

\* cited by examiner

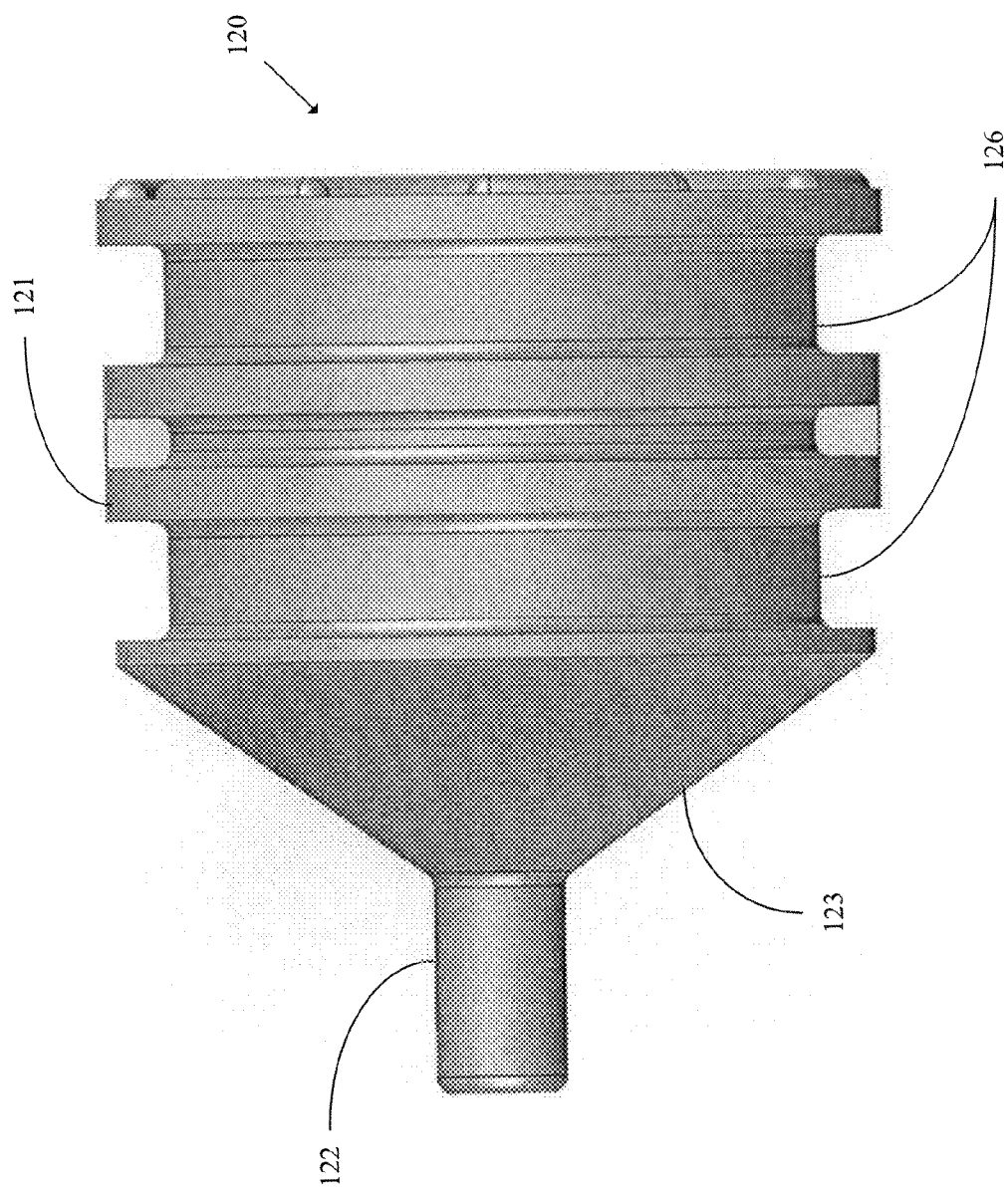

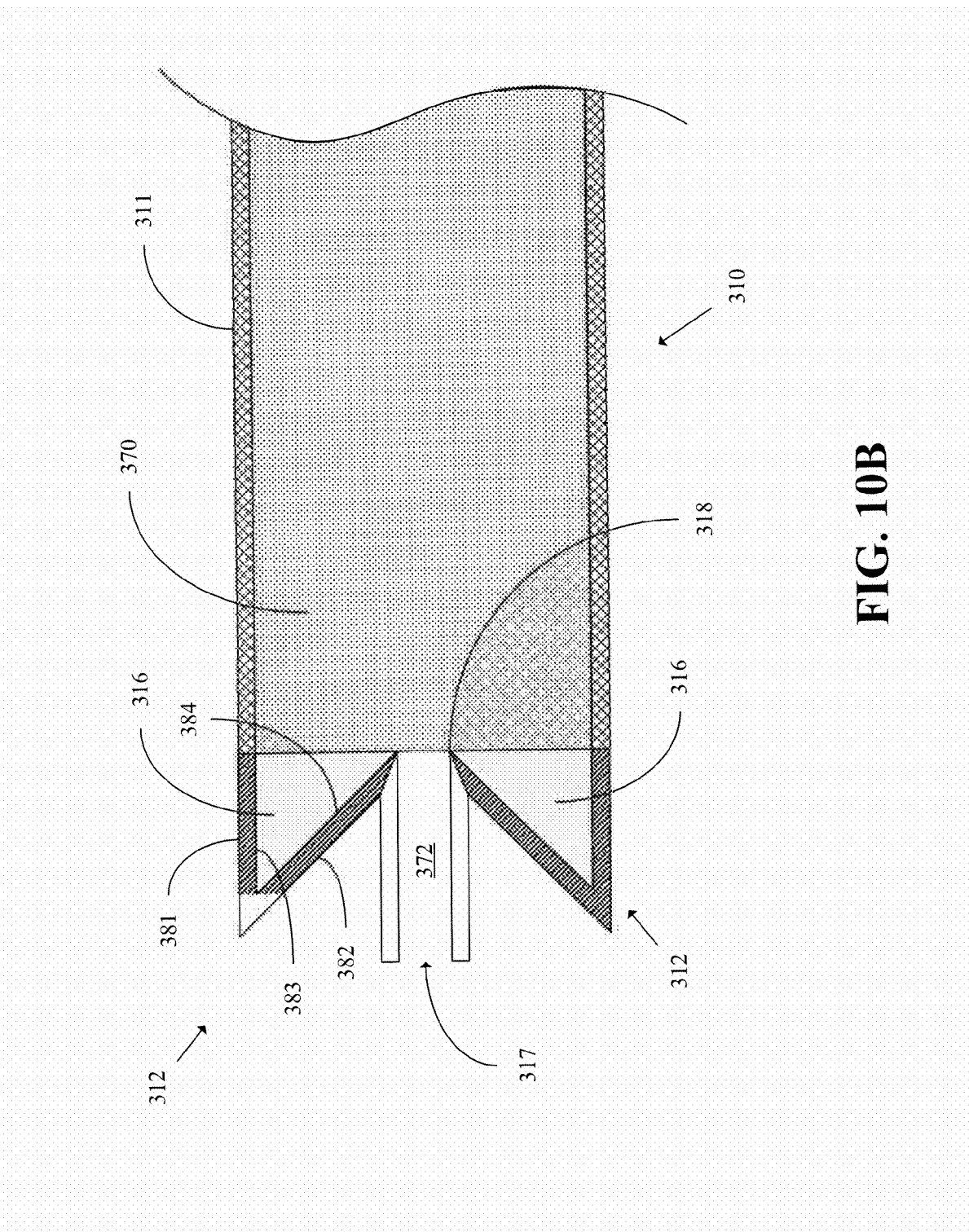

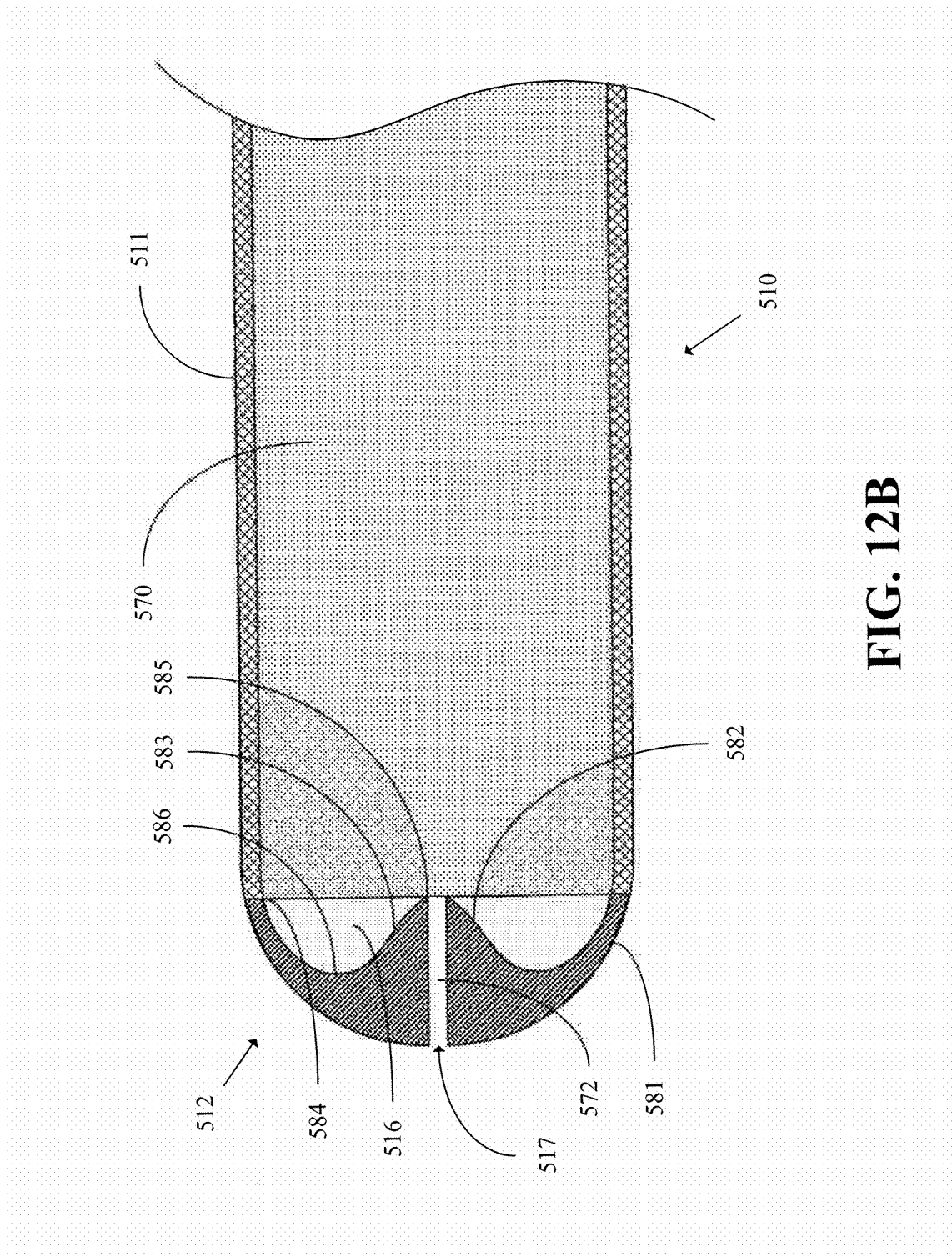

RESERVOIR SYSTEMS AND METHODS

CROSS-REFERENCE TO RELATED PATENT APPLICATIONS

This application is a Continuation-In-Part of U.S. application Ser. No. 11/964,649, filed Dec. 26, 2007, incorporated herein by reference in its entirety, which claims priority from Provisional Application U.S. Application No. 60/927,032, filed Apr. 30, 2007, incorporated herein by reference in its entirety.

BACKGROUND

1. Field

Embodiments of the present invention relate generally to systems and methods with reservoirs and, in specific embodiments, to a system with a reservoir and a plunger that are shaped to limit a presence of gas in a fluidic medium expelled from the reservoir.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have been configured in implantable devices, which are implanted inside of the body of a patient. External pump type delivery devices include devices designed for use in a stationary location, such as a hospital, a clinic, or the like, and further include devices configured for ambulatory or portable use, such as devices designed to be carried by a patient, or the like. External pump-type delivery devices may contain reservoirs of fluidic media, such as, but is not limited to, insulin.

External pump-type delivery devices may be connected in fluid flow communication to a patient or user-patient, for example, through suitable hollow tubing. The hollow tubing may be connected to a hollow needle that is designed to pierce the skin of the patient and to deliver fluidic media there through. Alternatively, the hollow tubing may be connected directly to the patient as through a cannula, or the like.

Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump-type delivery devices may be connected in fluid-flow communication to a patient-user, for example, through suitable hollow tubing. The hollow tubing may be connected to a hollow needle that is designed to pierce the patient-user's skin and deliver an infusion medium to the patient-user. Alternatively, the hollow tubing may be connected directly to the patient-user as or through a cannula or set of micro-needles.

In contexts in which the hollow tubing is connected to the patient-user through a hollow needle that pierces skin of the user-patient, a manual insertion of the needle into the patient-user can be somewhat traumatic to the user-patient. Accordingly, insertion mechanisms have been made to assist the insertion of a needle into the user-patient, whereby a needle is forced by a spring to move quickly from a retracted position into an extended position. As the needle is moved into the extended position, the needle is quickly forced through the skin of the user-patient in a single, relatively abrupt motion that can be less traumatic to certain user-patients as compared to a slower, manual insertion of a needle. While a quick thrust of the needle into the skin of the user-patient may be less traumatic to some user-patients than a manual insertion, it is believed that, in some contexts, some user-patients may feel less trauma if the needle is moved a very slow, steady pace.

Examples of insertion mechanisms that may be used with and may be built into a delivery device are described in: U.S. patent application Ser. No. 11/645,435, filed Dec. 26, 2006, titled "Infusion Medium Delivery system, Device And Method With Needle Inserter And Needle Inserter Device And Method,"; and U.S. patent application Ser. No. 11/211, 095, filed Aug. 23, 2005, titled "Infusion Device And Method With Disposable Portion" (each of which is assigned to the assignee of the present invention), each of which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety. Further examples of various insertion tools are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," all of which are herein incorporated by reference in their entirety.

Pump-type delivery devices can allow accurate doses of insulin to be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump-type delivery devices have become an important aspect of modern medical treatments of various types of medical conditions, such as diabetes. As pump technologies improve and as doctors and patient-users become more familiar with such devices, the popularity of external medical infusion pump treatment increases and is expected to increase substantially over the next decade.

SUMMARY OF THE DISCLOSURE

Various embodiments of the present invention are directed to limiting a presence of air bubbles in a fluidic medium expelled from a reservoir. In various embodiments, a plunger head within a reservoir is shaped so as to limit a presence of air bubbles in a fluidic medium expelled from the reservoir. In addition, in various embodiments, a reservoir is shaped so as to limit a presence of air bubbles in a fluidic medium expelled from the reservoir. In some embodiments, both a reservoir and a plunger head within the reservoir are shaped so as to limit a presence of air bubbles in a fluidic medium expelled from the reservoir.

A reservoir having a plunger head moveable within the reservoir to transfer fluidic media may include, but is not limited to, a reservoir body portion and a collecting portion. The reservoir body portion may have a wall defining an interior volume. The interior volume may be for containing the fluidic media. The reservoir may have a first port in the reservoir body portion to be in fluid flow communication with the interior volume of the reservoir body portion. The first port may be for expelling fluidic media from the interior volume of the reservoir body portion as the plunger is moved within the reservoir.

The collecting portion may have a wall defining a volume in fluid flow communication with the interior volume of the reservoir body portion. The volume of the collecting portion may be for collecting gas bubbles in the fluidic media as the fluidic media is expelled through the first port from the interior volume of the reservoir body portion. The reservoir may have a second port in the collecting portion to be in fluid flow communication with the volume of the collecting portion. The second port may be for receiving fluidic media into the reservoir.

In various embodiments, the first port and the second port may be are located to a same side of the interior volume of reservoir body portion.

In various embodiments, the reservoir may have an axis along which the plunger head moves to expel fluidic media from the interior volume of the reservoir body portion through the first port. The reservoir may be shaped to be asymmetric about its axis.

In various embodiments, the second port may be arranged further from the interior volume of the reservoir body portion than the first port.

In various embodiments, the reservoir may have a channel leading from the interior volume of the reservoir body portion to the first port of the reservoir.

In some embodiments, at least a portion of the reservoir may be arranged between the channel and the volume of the collecting portion.

In various embodiments, the reservoir may have a channel leading from the interior volume of the reservoir body portion to the second port of the reservoir. The volume of the collection portion may surround the channel.

In various embodiments, the reservoir body portion may have a length dimension extending from a rear end of the reservoir body portion to a front end of the reservoir body portion. The first port may be arranged on the front end of the reservoir body portion. The reservoir may have a length dimension extending from the rear end of the reservoir body portion to a front end of the collecting portion. The second port may be arranged on the front end of the collecting portion. The length dimension of the reservoir may be greater than the length dimension of the reservoir body.

In various embodiments, the collecting portion may protrude from the reservoir body portion.

In various embodiments, the second port may be for expelling gas collected in the volume of the collecting portion.

In various embodiments, the reservoir may be shaped such that in order for the fluidic media to flow from the volume of the collecting portion to the first port of the reservoir, the fluidic media must flow through the interior volume of the reservoir body portion.

In various embodiments, the collecting portion may have a first portion that extends from the reservoir body portion away from the interior volume of the reservoir body portion, and a second portion that returns toward the interior volume of the reservoir body portion.

In various embodiments, the collecting portion may have a first portion that extends from the reservoir body portion away from the interior volume of the reservoir body portion, and a second portion that extends from the first portion toward the interior volume of the reservoir body portion.

In various embodiments, the wall of the collecting portion may comprise a curved surface. The curved surface may have a first end region, a second end region, and a middle region between the first end region and the second end region. The first end region and the second end region may extend from the middle region toward the interior volume of the reservoir body portion such that the first end region and the second end region are located closer to the interior volume of the reservoir body portion than the middle region is to the interior volume of the reservoir body portion.

In some embodiments, the second port may be arranged in the middle region.

In some embodiments, the first end region may be in contact with the wall of the reservoir body portion; The second end region may be located adjacent the interior volume of the reservoir body portion.

In various embodiments, the reservoir may further comprise at least one of a surface treatment and a material on at least a portion of a surface of the wall of the collecting portion that causes the at least a portion of the surface to be hydrophobic.

In various embodiments, the reservoir may further comprise at least one of a surface treatment and a material on at least a portion of a surface of the wall of the collecting portion that causes the at least a portion of the surface to be hydrophilic.

In various embodiments, the reservoir may further comprise at least one of a first surface treatment and a first material on at least a first portion of the wall of the collecting portion that causes the at least a first portion to be hydrophobic and at least one of a second surface treatment and a second material on at least a second portion of the wall of the collecting portion that causes the at least a second portion to be hydrophilic.

In some embodiments, the at least a second portion of the wall of the collecting portion may be located closer to the interior volume of the reservoir body portion than the at least a first portion is to the interior volume of the reservoir body portion.

A method of manufacturing a reservoir having a plunger head moveable within the reservoir to transfer fluidic media may include, but is not limited to, any one or combination of: providing a reservoir body portion having a wall defining an interior volume, the interior volume for containing the fluidic media, the reservoir having a first port in the reservoir body portion to be in fluid flow communication with the interior volume of the reservoir body portion, the first port for expelling fluidic media from the interior volume of the reservoir body portion as the plunger is moved within the reservoir; and (ii) providing a collecting portion having a wall defining a volume in fluid flow communication with the interior volume of the reservoir body portion, the volume of the collecting portion for collecting gas bubbles in the fluidic media as the fluidic media is expelled through the first port from the interior volume of the reservoir body portion, the reservoir having a second port in the collecting portion to be in fluid flow communication with the volume of the collecting portion, the second port for receiving fluidic media into the reservoir.

A system for transferring fluidic media may include, but is not limited to, a plunger head and a reservoir. The reservoir may include a reservoir body portion and a collecting portion. The reservoir body portion may have a wall defining an interior volume. The interior volume may be for containing the fluidic media. The reservoir may have a first port in the reservoir body portion to be in fluid flow communication with the interior volume of the reservoir body portion. The first port may be for expelling fluidic media from the interior volume of the reservoir body portion as the plunger is moved within the reservoir. The collecting portion may have a wall defining a volume in fluid flow communication with the interior volume of the reservoir body portion. The volume of the collecting portion may be for collecting gas bubbles in the fluidic media as the fluidic media is expelled through the first port from the interior volume of the reservoir body portion. The reservoir may have a second port in the collecting portion to be in fluid flow communication with the volume of the collecting portion. The second port may be for receiving fluidic media into the reservoir. The plunger head may be moveable with the reservoir along a length dimension of the reservoir body portion to expel the fluidic media through the first port from the interior volume of the reservoir body portion.

In various embodiments, the plunger head may have a contour that substantially matches an inner contour of the wall of the collecting portion.

In various embodiments, the reservoir has an axis along which the plunger head moves to expel fluidic media from the interior volume of the reservoir body portion through the first port. The plunger head may be shaped to be asymmetric about the axis of the reservoir.

In various embodiments, the plunger may have a first side and a second side opposite the first side. The first side may have a length dimension. The second side may have a length dimension greater than the length dimension of the first side.

In various embodiments, the plunger head may comprise a body portion and a protruding portion. The protruding portion may extend toward the collecting portion.

In some embodiments, the protruding portion may have a contour that substantially matches an inner contour of the wall of the collecting portion.

In some embodiments, the protruding portion may be arranged to be aligned with the second port in a direction parallel to the length dimension of the reservoir body portion.

In some embodiments, the protruding portion may be wedge shaped so as to direct gas in the fluidic media in the interior volume of the reservoir body portion into the volume of the collecting portion.

In some embodiments, the protruding portion of the plunger may have a concavity for collecting gas bubbles as the fluidic media is expelled through the first port.

In some embodiments, the protruding portion may have a size such that when the plunger head is fully advanced within the reservoir, the protruding portion substantially fills the volume of the collecting portion.

In further embodiments, the protruding portion may be shaped such that the protruding portion fills less than all of the volume of the collecting portion when the plunger head is fully advanced within the reservoir, so that one or more pockets of gas exist between the protruding portion and an inner surface of the wall of the collecting portion when the plunger head is fully advanced within the reservoir.

In some embodiments, the protruding portion may be positioned and shaped such that the protruding portion extends at least partially into the volume of the collecting portion when the plunger head is sufficiently advanced within the reservoir.

In various embodiments, the system may further include at least one of a surface treatment and a material on at least a portion of a surface of the plunger head that causes the at least a portion of the surface to be hydrophobic.

In various embodiments, the system may further include at least one of a surface treatment and a material on at least a portion of a surface of the plunger head that causes the at least a portion of the surface to be hydrophilic.

In various embodiments, the plunger head may comprise a seal member arranged to provide a seal between the plunger head and the wall of the reservoir body portion.

In some embodiments, the plunger head may have a recess for receiving the seal member. The plunger head may have a channel from the recess to the interior volume of the reservoir body portion through which fluidic media may enter the recess from the interior volume of the reservoir body portion.

A method of manufacturing a system for transferring fluidic media may include, but is not limited, any one or combination of (i) providing a plunger head; and (ii) providing a reservoir, the reservoir comprising: a reservoir body portion having a wall defining an interior volume, the interior volume for containing the fluidic media, the reservoir having a first port in the reservoir body portion to be in fluid flow communication with the interior volume of the reservoir body portion, the first port for expelling fluidic media from the interior volume of the reservoir body portion as the plunger is moved within the reservoir; and a collecting portion having a wall defining a volume in fluid flow communication with the interior volume of the reservoir body portion, the volume of the collecting portion for collecting gas bubbles in the fluidic media as the fluidic media is expelled through the first port from the interior volume of the reservoir body portion, the reservoir having a second port in the collecting portion to be in fluid flow communication with the volume of the collecting portion, the second port for receiving fluidic media into the reservoir; the plunger head moveable with the reservoir along a length dimension of the reservoir body portion to expel the fluidic media through the first port from the interior volume of the reservoir body portion.

A plunger head may be moveable along an axial dimension of a reservoir to expel fluidic media from an interior volume of the reservoir through a port of the reservoir. The plunger head may be asymmetric about the axial dimension of the reservoir.

In various embodiments, the plunger head may have an axial dimension. The plunger head may be asymmetric about the axial dimension.

In various embodiments, the plunger head may have a contour that substantially matches an inner contour of the reservoir.

In various embodiments, the plunger may have a first side and a second side opposite the first side. The first side may have a length dimension parallel the axial dimension of the reservoir. The second side may have a length dimension parallel the axial dimension of the reservoir. The length dimension of the second side may be greater than the length dimension of the first side.

In various embodiments, the plunger head may further include at least one of a surface treatment and a material on at least a portion of a surface of the plunger head that causes the at least a portion of the surface to be hydrophobic.

In various embodiments, the plunger head may further include at least one of a surface treatment and a material on at least a portion of a surface of the plunger head that causes the at least a portion of the surface to be hydrophilic.

In various embodiments, the plunger head may include a body portion and a protruding portion. The protruding portion may extend from the body portion along the axial dimension of the reservoir in a direction of movement that the plunger moves to expel fluidic media from the reservoir.

In some embodiments, the protruding portion of the plunger may have a concavity for collecting gas bubbles as the fluidic media from the reservoir.

In some embodiments, as the plunger head is moved in the reservoir, the protruding portion may be aligned with a port of the reservoir through which fluidic media is received into the reservoir in a direction parallel to the axial dimension of the reservoir.

In further embodiments, as the plunger head is moved in the reservoir, the protruding portion may not aligned with the port of the reservoir through which fluidic media is expelled from the reservoir in a direction parallel to the axial dimension of the reservoir.

In various embodiments, the plunger head may include a seal member arranged to provide a seal between the plunger head and the reservoir.

In some embodiments, the plunger head may have a recess for receiving the seal member. The plunger head may have a channel from the recess to the interior volume of the reservoir through which fluidic media may enter the recess from the interior volume of the reservoir.

BRIEF DESCRIPTION OF THE DRAWINGS

FIG. 7D illustrates a side view of a plunger head in accordance with an embodiment of the present invention;

FIG. 10B illustrates a cross-sectional view of a reservoir in accordance with an embodiment of the present invention;

FIG. 12B illustrates a cross-sectional view of a reservoir in accordance with an embodiment of the present invention;

DETAILED DESCRIPTION

Figure 1:
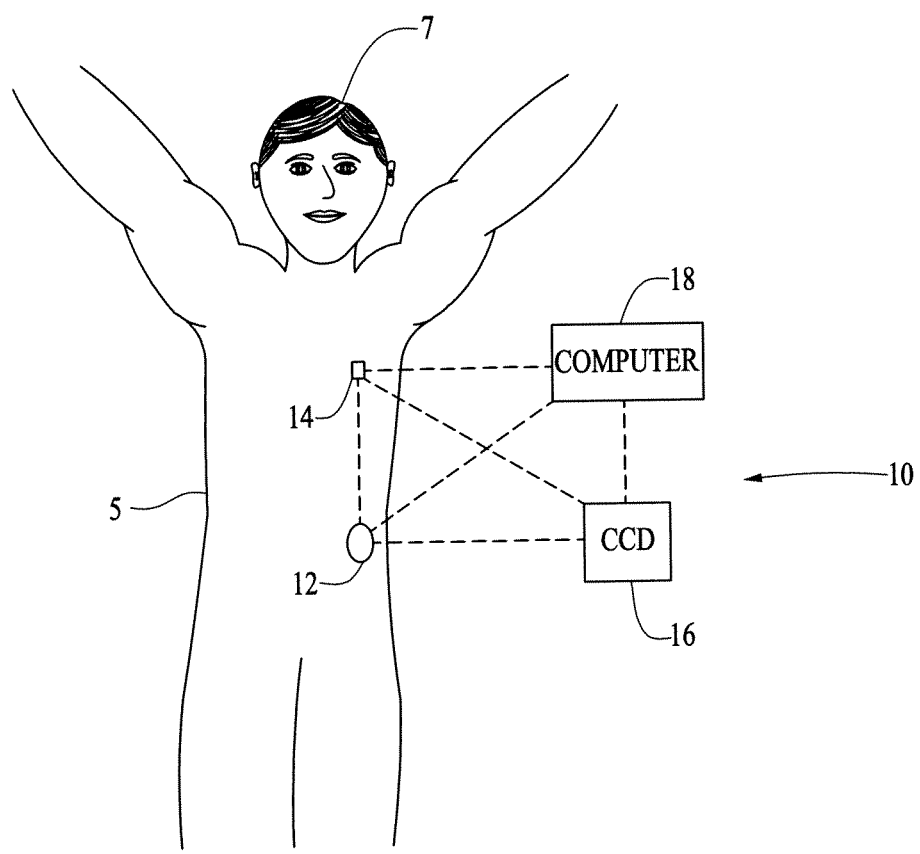
FIG. 1 illustrates a generalized representation of a system in accordance with an embodiment of the present invention.

FIG. 1 illustrates a generalized representation of a system 10 in accordance with an embodiment of the present invention. The system 10 may include a delivery device 12. The system 10 may further include a sensing device 14, a command control device (CCD) 16, and a computer 18. In various embodiments, the delivery device 12 and the sensing device 14 may be secured at desired locations on the body 5 of a patient or user-patient 7. The locations at which the delivery device 12 and the sensing device 14 are secured to the body 5 of the user-patient 7 in FIG. 1 are provided only as representative, non-limiting, examples.

The system 10, the delivery device 12, the sensing device 14, the CCD 16, and computer 18 may be similar to those described in the following U.S. patent applications that were assigned to the assignee of the present invention, where each of following patent applications is incorporated herein by reference in its entirety: (i) U.S. patent application Ser. No. 11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588,847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No. 11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604,172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S. patent application Ser. No. 11/606,836, filed Nov. 30, 2006, "Infusion Pumps And Methods And Delivery Devices And Methods With Same"; U.S. patent application Ser. No. 11/636,384, filed Dec. 8, 2006, "Infusion Medium Delivery Device And Method With Compressible Or Curved Reservoir Or Conduit"; (xv) U.S. patent application Ser. No. 11/645,993, filed Dec. 26, 2006, "Infusion Medium Delivery Device And Method With Compressible Or Curved Reservoir Or Conduit"; U.S. patent application Ser. No. 11/645,972, filed Dec. 26, 2006, "Infusion Medium Delivery System, Device And Method With Needle Inserter And Needle Inserter Device And Method"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; (xix) U.S. patent application Ser. No. 11/759,725, filed Jun. 7, 2007, "Infusion Medium Delivery Device And Method With Drive Device For Driving Plunger In Reservoir"; (xx) U.S. patent application Ser. No. 11/606,837, filed Nov. 30, 2006, "Method And Apparatus For Enhancing The Integrity Of An Implantable Sensor Device"; (xxi) U.S. patent application Ser. No. 11/702,713, filed Feb. 5, 2007, "Selective Potting For Controlled Failure And Electronic Devices Employing The Same"; (xxii) U.S. patent application Ser. No. 11/843,601, filed Aug. 22, 2007, "System And Method For Sensor Recalibration"; (xxiii) U.S. patent application Ser. No. 11/868,898, filed Oct. 8, 2007, "Multilayer Substrate"; (xxiv) U.S. patent application Ser. No. 11/964,649, filed Dec. 26, 2007, "System And Methods Allowing For Reservoir Air Bubble Management"; (xxv) U.S. patent application Ser. No. 12/111,751, filed Apr. 29, 2008, "Systems And Methods For Reservoir Filling"; (xxvi) U.S. patent application Ser. No. 12/111,815, filed Apr. 29, 2008, "Systems And Methods For Reservoir Air Bubble Management"; (xxvii) U.S. patent application Ser. No. 11/924,402, filed Oct. 25, 2007, "Sensor Substrate And Method Of Fabricating Same"; (xxviii) U.S. patent application Ser. No. 11/929,428, filed Oct. 30, 2007, "Telemetry System And Method With Variable Parameters"; (xxix) U.S. patent application Ser. No. 11/965,578, filed Dec. 27, 2007, "Reservoir Pressure Equalization Systems And Methods"; (xxx) U.S. patent application Ser. No. 12/107,580, filed Apr. 22, 2008, "Automative Filling Systems And Methods"; (xxxi) U.S. patent application Ser. No. 11/964,663, filed Dec. 26, 2007, "Medical Device With Full Options And Selective Enablement/Disablement"; (xxxii) U.S. patent application Ser. No. 10/180,732, filed Jun. 26, 2002, "Communication Station And Software For Interfacing With An Infusion Pump, Analyte Monitor, Analyte Meter, Or The Like"; (xxxiii) U.S. patent application Ser. No. 12/099,738, filed Apr. 8, 2008, "Systems And Methods Allowing For Reservoir Air Bubble Management"; (xxxiv) U.S. patent application Ser. No. 12/027,963, filed Feb. 7, 2008, "Adhesive Patch Systems And Methods"; (xxxv) U.S. patent application Ser. No. 12/121,647, filed May 15, 2008, "Multi-Lumen Catheter"; (xxxvi) U.S. Patent Provisional Application Ser. No. 61/044,269, filed Apr. 11, 2008, "Reservoir Plunger Head Systems And Methods"; (xxxvii) U.S. Patent Application Ser. No. 61/044,292, filed Apr. 11, 2008, "Reservoir Barrier Layer Systems And Methods"; (xxxviii) U.S. Patent Provisional Application Ser. No. 61/044,322, filed Apr. 11, 2008, "Reservoir Seal Retainer Systems And Methods"; (xxxix) U.S. patent application Ser. No. 12/179,502, filed Jul. 24, 2008, "Method For Formulating And Immobilizing A Matrix Protein And A Matrix Protein For Use In A Sensor"; (xl) U.S. patent application Ser. No. 12/336,367, filed Dec. 16, 2008, "Needle Insertions Systems And Methods"; (xli) U.S. patent application Ser. No. 12/166,210, filed Jul. 1, 2008, "Electronic Device For Controlled Failure"; (xlii) U.S. patent application Ser. No. 12/271,134, filed Nov. 14, 2008, "Multilayer Circuit Devices And Manufacturing Methods Using Electroplated Sacrificial Structures"; (xliii) U.S. patent application Ser. No. 12/171,971, filed Jul. 11, 2008, "Infusion Medium Delivery System, Device And Method With Needle Inserter And Needle Inserter Device And Method"; (xliv) U.S. patent application Ser. No. 12/189,077, filed Aug. 8, 2008, "Packaging System"; (xlv) U.S. patent application Ser. No. 12/179,536, filed Jul. 24, 2008, "Real Time Self-Adjusting Calibration Algorithm"; (xlvii) U.S. patent application Ser. No. 12/277,186, filed Nov. 24, 2008, "Infusion Medium Delivery System, Device And Method With Needle Inserter And Needle Inserter Device And Method"; (xlviii) U.S. patent application Ser. No. 12/211,783, filed Sep. 16, 2008, "Implantable Sensor Method And System"; (xlix) U.S. patent application Ser. No. 12/247,945, filed Oct. 8, 2008, "Infusion Medium Delivery Device And Method With Drive Device For Driving Plunger In Reservoir"; (1) U.S. patent application Ser. No. 12/360,077, filed Jan. 26, 2009, "Reservoir Barrier Layer Systems And Methods"; (li) U.S. patent application Ser. No. 12/345,362, filed Dec. 29, 2008, "Reservoir Seal Retainer Systems And Methods"; (lii) U.S. patent application Ser. No. 12/353,181, filed Jan. 13, 2009, "Systems And Methods Allowing For Reservoir Filling And Infusion Medium Delivery"; (liii) U.S. patent application Ser. No. 12/360,813, filed Jan. 27, 2009, "Multi-Position Infusion Set Device And Process"; (liv) U.S. Patent Pub. No. US 2007/0142776 (application Ser. No. 10/314,653), filed Dec. 9, 2002, "Insertion Device For An Insertion Set and Methods Of Using The Same." In other embodiments, the system 10, delivery device 12, sensing device 14, CCD 16, and computer 18 may have other suitable configurations.

The delivery device 12 may be configured to deliver fluidic media to the body 5 of the user-patient 7. In various embodiments, fluidic media may include a liquid, a fluid, a gel, or the like. In some embodiments, fluidic media may include a medicine or a drug for treating a disease or a medical condition. For example, fluidic media may include insulin for treating diabetes, or may include a drug for treating pain, cancer, a pulmonary disorder, HIV, or the like. In some embodiments, fluidic media may include a nutritional supplement, a dye, a tracing medium, a saline medium, a hydration medium, or the like.

The sensing device 14 may include a sensor, a monitor, or the like, for providing sensor data or monitor data. In various embodiments, the sensing device 14 may be configured to sense a condition of the user-patient 7. For example, the sensing device 14 may include electronics and enzymes reactive to a biological condition, such as a blood glucose level, or the like, of the user-patient 7.

In various embodiments, the sensing device 14 may be secured to the body 5 of the user-patient 7 or embedded in the body 5 of the user-patient 7 at a location that is remote from the location at which the delivery device 12 is secured to the body 5 of the user-patient 7. In various other embodiments, the sensing device 14 may be incorporated within the delivery device 12. In other embodiments, the sensing device 14 may be separate and apart from the delivery device, and may be, for example, part of the CCD 16. In such embodiments, the sensing device 14 may be configured to receive a biological sample, analyte, or the like, to measure a condition of the user-patient 7.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S. patent application Ser. No. 09/360,342, filed Jul. 22, 1999, entitled "Substrate Sensor"; and (viii) U.S. Provisional Patent Application Ser. No. 60/318,060, filed Sep. 7, 2001, entitled "Sensing Apparatus and Process", all of which are incorporated herein by reference in their entirety.

In such embodiments, the sensing device 14 may be configured to sense a condition of the user-patient 7, such as, but not limited to, blood glucose level, or the like. The delivery device 12 may be configured to deliver fluidic media in response to the condition sensed by the sensing device 14. In turn, the sensing device 14 may continue to sense a new condition of the user-patient, allowing the delivery device 12 to deliver fluidic media continuously in response to the new condition sensed by the sensing device 14 indefinitely. In some embodiments, the sensing device 14 and/or the delivery device 12 may be configured to utilize the closed-loop system only for a portion of the day, for example only when the user-patient is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user-patient 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. In addition, in various embodiments, the delivery device 12 and/or the sensing device 14 may be configured to transmit data to the CCD 16 and/or the computer 18 for display or processing of the data by the CCD 16 and/or the computer 18.

In some embodiments, the sensing device 14 may be integrated into the CCD 16. Such embodiments may allow the user-patient to monitor a condition by providing, for example, a sample of his or her blood to the sensing device 14 to assess his or her condition. In some embodiments, the sensing device 14 and the CCD 16 may be for determining glucose levels in the blood and/or body fluids of the user-patient without the use of, or necessity of, a wire or cable connection between the delivery device 12 and the sensing device 14 and/or the CCD 16.

In some embodiments, the CCD 16 may be for providing information to the user-patient that facilitates the user-patient's subsequent use of a drug delivery system. For example, the CCD 16 may provide information to the user-patient to allow the user-patient to determine the rate or dose of medication to be administered into the body of the user-patient. In other embodiments, the CCD 16 may provide information to the delivery device 12 to control the rate or dose of medication administered into the body of the user-patient Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same," all of which are incorporated herein by reference in their entirety.

Figure 2:
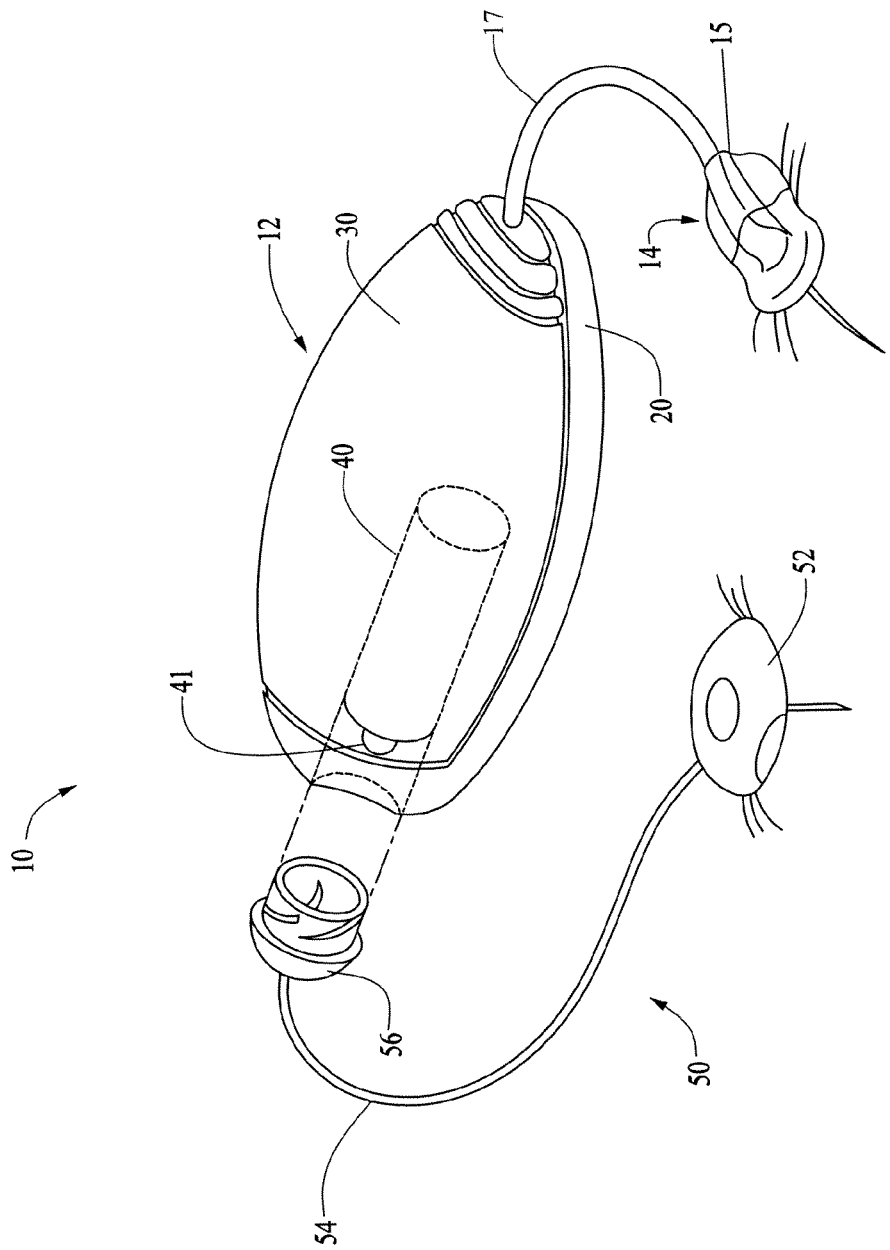
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention may include a disposable housing 20, a durable housing 30, and a reservoir system 40. The delivery device 12 may further include an infusion path 50.

Elements of the delivery device 12 that ordinarily contact the body of a user-patient or that ordinarily contact fluidic media during operation of the delivery device 12 may be considered as a disposable portion of the delivery device 12. For example, a disposable portion of the delivery device 12 may include the disposable housing 20 and the reservoir system 40. The disposable portion of the delivery device 12 may be recommended for disposal after a specified number of uses.

On the other hand, elements of the delivery device 12 that do not ordinarily contact the body of the user-patient or fluidic media during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user-patient or fluidic media during normal operation of the delivery device 12 and, thus, may be retained for re-use with replaced disposable portions of the delivery device 12.

In various embodiments, the disposable housing 20 may support the reservoir system 40 and has a bottom surface (facing downward and into the page in FIG. 2) configured to secure to the body of the user-patient. An adhesive may be employed at an interface between the bottom surface of the disposable housing 20 and the skin of the user-patient to adhere the disposable housing 20 to the skin of the user-patient. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the user-patient, for example against the skin of the user-patient. Thus in some embodiments, the delivery device 12 may be attached to the skin of the user-patient.

In other embodiments, the disposable housing 20 and/or the remaining portions of the delivery device 12 may be worn or otherwise attached on or underneath clothing of the user-patient. Similarly, the delivery device 12 may be supported by any suitable manner, such as, but not limited to, on a belt, in a pocket, and the like. Representative examples of such delivery devices 12, and delivery devices in general, may include, but is not limited to, the MiniMed Paradigm 522 Insulin Pump, MiniMed Paradigm 722 Insulin Pump, MiniMed Paradigm 515 Insulin Pump, MiniMed Paradigm 715 Insulin Pump, MiniMed Paradigm 512R Insulin Pump, MiniMed Paradigm 712R Insulin Pump, MiniMed 508 Insulin Pump, MiniMed 508R Insulin Pump, and any other derivatives thereof.

The reservoir system 40 may be configured for containing or holding fluidic media, such as, but not limited to insulin. In various embodiments, the reservoir system 40 may include a hollow interior volume for receiving fluidic media, such as, but not limited to, a cylinder-shaped volume, a tubular-shaped volume, or the like. In some embodiments, the reservoir system 40 may be provided as a cartridge or canister for containing fluidic media. In various embodiments, the reservoir system 40 can be refilled with fluidic media. In further embodiments, the reservoir system 40 is pre-filled with fluidic media.

The reservoir system 40 may be supported by the disposable housing 20 in any suitable manner. For example, the disposable housing 20 may be provided with projections or struts (not shown), or a trough feature (not shown), for holding the reservoir system 40. In some embodiments, the reservoir system 40 may be supported by the disposable housing 20 in a manner that allows the reservoir system 40 to be removed from the disposable housing 20 and replaced with another reservoir. Alternatively, or in addition, the reservoir system 40 may be secured to the disposable housing 20 by a suitable adhesive, a strap, or other coupling structure.

In various embodiments, the reservoir system 40 may include at least one port 41 for allowing fluidic media to flow into and/or flow out of the interior volume of the reservoir system 40. In some embodiments, the infusion path 50 may include a connector 56, a tube 54, and a needle apparatus 52. The connector 56 of the infusion path 50 may be connectable to the port 41 of the reservoir system 40. In various embodiments, the disposable housing 20 may be configured with an opening near the port 41 of the reservoir system 40 for allowing the connector 56 of the infusion path 50 to be selectively connected to and disconnected from the port 41 of the reservoir system 40.

In various embodiments, the port 41 of the reservoir system 40 may be covered with or supports a septum (not shown in FIG. 2), such as a self-sealing septum, or the like. The septum may be configured to prevent fluidic media from flowing out of the reservoir system 40 through the port 41 when the septum is not pierced. In addition, in various embodiments, the connector 56 of the infusion path 50 may include a needle for piercing the septum covering the port 41 of the reservoir system 40 to allow fluidic media to flow out of the interior volume of the reservoir system 40.

Examples of needle/septum connectors can be found in U.S. patent application Ser. No. 10/328,393, filed Dec. 22, 2003, entitled "Reservoir Connector," which is incorporated herein by reference in its entirety. In other alternatives, non-septum connectors such as Luer locks, or the like may be used. In various embodiments, the needle apparatus 52 of the infusion path 50 may include a needle that is able to puncture the skin of the user-patient. In addition, in various embodiments, the tube 54 connects the connector 56 with the needle apparatus 52 and may be hollow, such that the infusion path 50 is able to provide a path to allow for the delivery of fluidic media from the reservoir system 40 to the body of a user-patient.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features that allow the two parts to connect together easily, by manually pressing the two housings together, by twist or threaded connection, or other suitable manner of connecting the parts that is well known in the mechanical arts.

In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20 to provide a seal against water entering between the durable housing 30 and the disposable housing 20.

The durable housing 30 of the delivery device 12 may support a drive device (not shown in FIG. 2), including a motor and a drive device linkage portion, for applying a force to fluidic media within the reservoir system 40 to force fluidic media out of the reservoir system 40 and into an infusion path, such as the infusion path 50, for delivery to a user-patient. For example, in some embodiments, an electrically driven motor may be mounted within the durable housing 30 with appropriate linkage for operatively coupling the motor to a plunger arm (not shown in FIG. 2) connected to a plunger head (not shown in FIG. 2) that is within the reservoir system 40 and to drive the plunger head in a direction to force fluidic media out of the port 41 of the reservoir system 40 and to the user-patient.

Also, in some embodiments, the motor may be controllable to reverse direction to move the plunger arm and the plunger head to cause fluid to be drawn into the reservoir system 40 from a patient. The motor may be arranged within the durable housing 30 and the reservoir system 40 may be correspondingly arranged on the disposable housing 20, such that the operable engagement of the motor with the plunger head, through the appropriate linkage, occurs automatically upon the user-patient connecting the durable housing 30 with the disposable housing 20 of the delivery device 12. Further examples of linkage and control structures may be found in U.S. patent application Ser. No. 09/813,660, filed Mar. 21, 2001, entitled "Control Tabs for Infusion Devices and Methods of Using the Same," which is incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user-patient, a greater level of user-patient comfort may be achieved when the disposable housing 20 is secured to the skin of the user-patient. In addition, a flexible disposable housing 20 may result in an increase in site options on the body of the user-patient at which the disposable housing 20 may be secured.

In the embodiment illustrated in FIG. 2, the delivery device 12 is connected to the sensing device 14 through a connection element 17 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

In some embodiments, the sensor 15 may include a continuous glucose sensor. The continuous glucose sensor may be implantable within the body of the user-patient. In other embodiments, the continuous glucose sensor may be located externally, for example on the skin of the user-patient, or attached to clothing of the user-patient. In such embodiments, fluid may be drawn continually from the user-patient and sensed by the continuous glucose sensor. In various embodiments, the continuous glucose sensor may be configured to sense and/or communicate with the CCD 16 continuously. In other embodiments, the continuous glucose sensor may be configured to sense and/or communicate with the CCD 16 intermittently, for example sense glucose levels and transmit information every few minutes. In various embodiments, the continuous glucose sensor may utilize glucose oxidase.

The sensor 15 may be an external sensor that secures to the skin of a user-patient or, in other embodiments, may be an implantable sensor that is located in an implant site within the body of the user-patient. In further alternatives, the sensor may be included with as a part or along side the infusion cannula and/or needle, such as for example as shown in U.S. patent application Ser. No. 11/149,119, filed Jun. 8, 2005, entitled "Dual Insertion Set," which is incorporated herein by reference in its entirety. In the illustrated example of FIG. 2, the sensor 15 is an external sensor having a disposable needle pad that includes a needle for piercing the skin of the user-patient and enzymes and/or electronics reactive to a biological condition, such as blood glucose level or the like, of the user-patient. In this manner, the delivery device 12 may be provided with sensor data from the sensor 15 secured to the user-patient at a site remote from the location at which the delivery device 12 is secured to the user-patient.

While the embodiment shown in FIG. 2 may include a sensor 15 connected by the connection element 17 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic media delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (unused) disposable housing 20 for further delivery operation with a user-patient.

Figure 3:
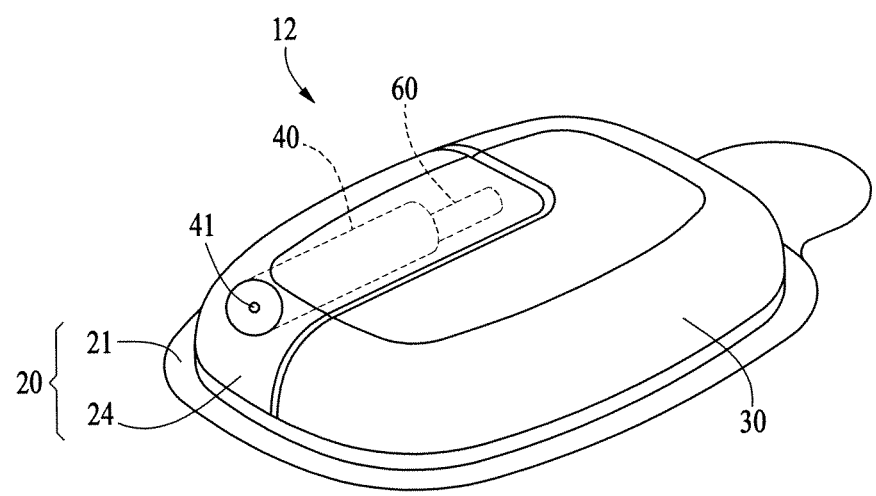
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir system 40, the delivery device 12 in the embodiment of FIG. 3 provides for the durable housing 30 to secure to the disposable housing 20 without covering the reservoir system 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 may be configured to be securable to a body of a user-patient. The reservoir-retaining portion 24 of the disposable housing 20 is configured to house the reservoir system 40. The reservoir-retaining portion 24 of the disposable housing 20 may be configured to have an opening to allow for the port 41 of the reservoir system 40 to be accessed from outside of the reservoir-retaining portion 24 while the reservoir system 40 is housed in the reservoir-retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir system 40.

Figure 4:
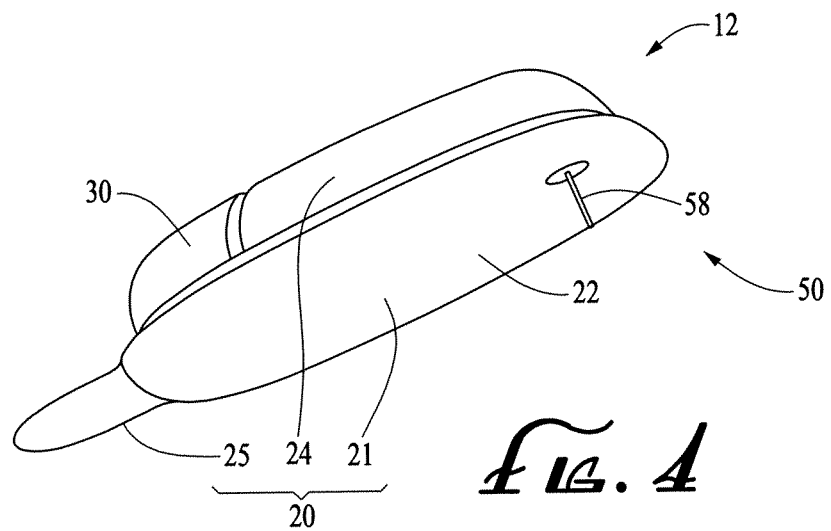
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir-retaining portion 24, and a peelable cover layer 25. The peelable cover layer 25 may cover an adhesive material on the bottom surface 22 of the base 21. The peelable cover layer 25 may be configured to be peelable by a user-patient to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user-patient under the base 21, when extended. In this manner, the needle 58 may be used to pierce the skin of the user-patient and deliver fluidic media to the user-patient.

Alternatively, the needle 58 may be extended through a hollow cannula (not shown in FIG. 4), such that upon piercing the skin of the user-patient with the needle 58, an end of the hollow cannula is guided through the skin of the user-patient by the needle 58. Thereafter, the needle 58 may be removed, leaving the hollow cannula in place, with one end of the cannula located within the body of the user-patient and the other end of the cannula in fluid flow connection with fluidic media within the reservoir system 40, to convey pumped infusion media from the reservoir system 40 to the body of the user-patient.

Figure 5A:
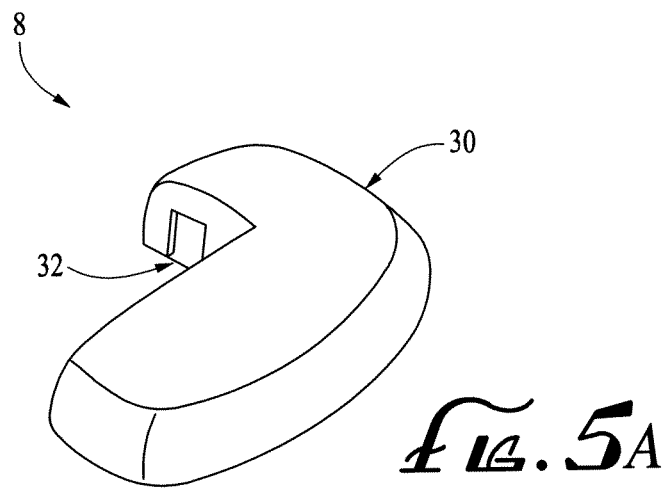
FIG. 5A illustrates a durable portion of a delivery device in accordance with an embodiment of the present invention.
Figure 5B:
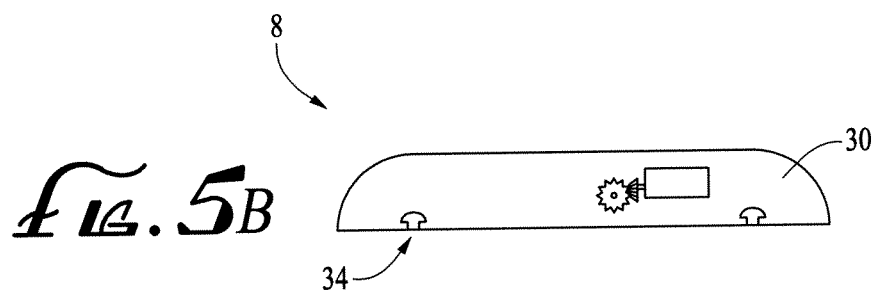
FIG. 5B illustrates a section view of a durable portion of a delivery device in accordance with an embodiment of the present invention.
Figure 5C:
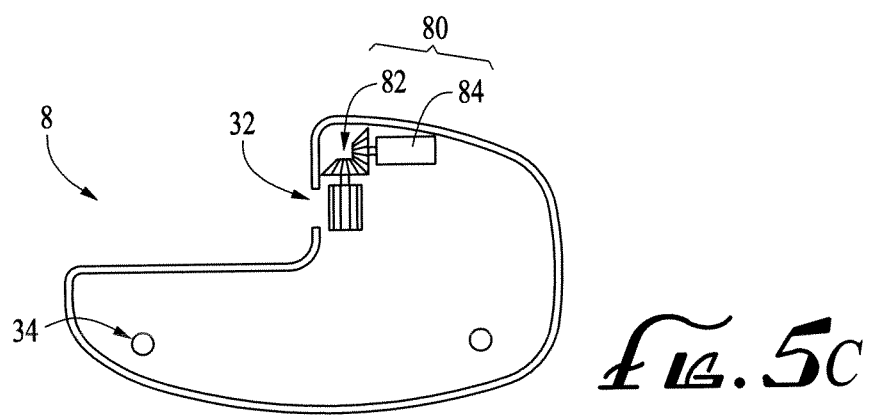
FIG. 5C illustrates a section view of a durable portion of a delivery device in accordance with an embodiment of the present invention.

FIG. 5A illustrates a durable portion 8 of the delivery device 12 (refer to FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 may include the durable housing 30, and a drive device 80. The drive device 80 may include a motor 84 and a drive device linkage portion 82.

In various embodiments, the durable housing 30 may include an interior volume for housing the motor 84, the drive device linkage portion 82, other electronic circuitry, and a power source (not shown in FIGS. 5A, 5B, and 5C). In addition, in various embodiments, the durable housing 30 may be configured with an opening 32 for receiving a plunger arm 60 (refer to FIG. 3). In addition, in various embodiments, the durable housing 30 may include one or more connection members 34, such as tabs, insertion holes, or the like, for connecting with the base 21 of the disposable housing 20 (refer to FIG. 3).

Figure 6A:
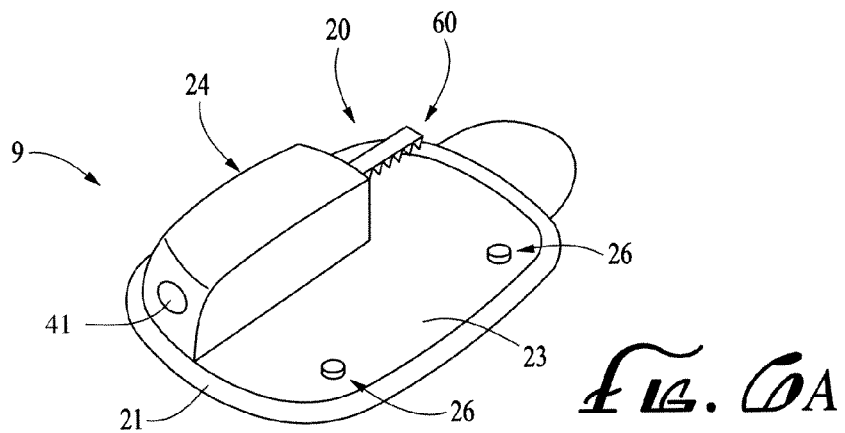
FIG. 6A illustrates a disposable portion of a delivery device in accordance with an embodiment of the present invention.
Figure 6B:
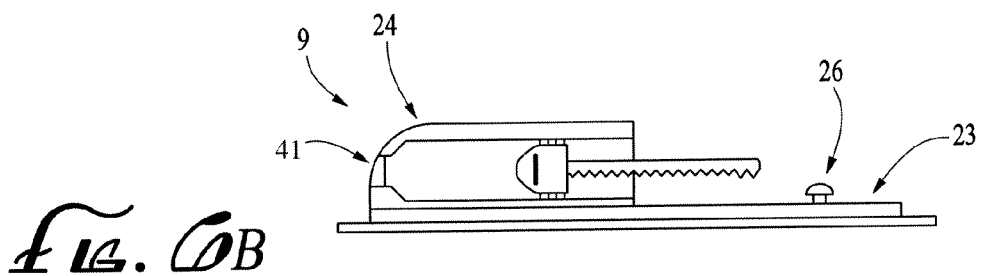
FIG. 6B illustrates a section view of a disposable portion of a delivery device in accordance with an embodiment of the present invention.
Figure 6C:
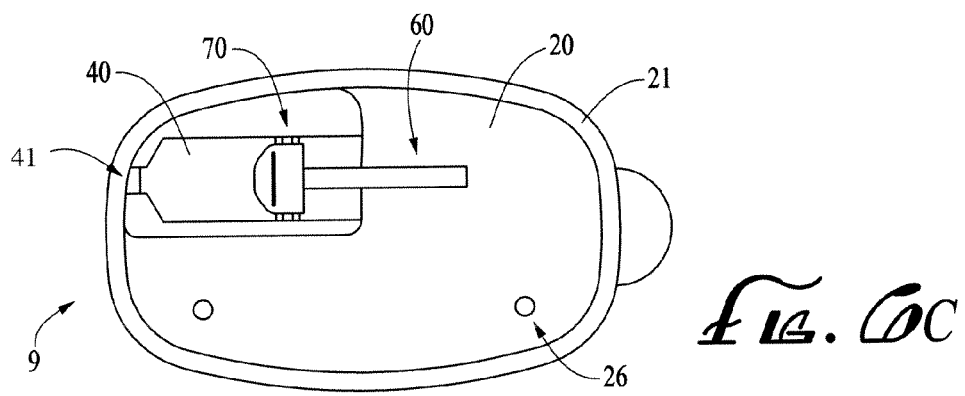
FIG. 6C illustrates a section view of a disposable portion of a delivery device in accordance with an embodiment of the present invention.

FIG. 6A illustrates a disposable portion 9 of the delivery device 12 (refer to FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir system 40, the plunger arm 60, and a plunger head 70. In some embodiments, the disposable housing 20 may include the base 21 and the reservoir-retaining portion 24. In various embodiments, the base 21 may include a top surface 23 having one or more connection members 26, such as tabs, grooves, or the like, for allowing connections with the one or more connection members 34 of embodiments of the durable housing 30 (refer to FIG. 5B).

In various embodiments, the reservoir system 40 may be housed within the reservoir retaining portion 24 of the disposable housing 20, and the reservoir system 40 may be configured to hold fluidic media. In addition, in various embodiments, the plunger head 70 may be disposed at least partially within the reservoir system 40 and may be moveable within the reservoir system 40 to allow fluidic media to fill into the reservoir system 40 and to force fluidic media out of the reservoir system 40. In some embodiments, the plunger arm 60 may be connected to or is connectable to the plunger head 70.

Also, in some embodiments, a portion of the plunger arm 60 may extend to outside of the reservoir-retaining portion 24 of the disposable housing 20. In various embodiments, the plunger arm 60 may have a mating portion for mating with the drive device linkage portion 82 of the drive device 80 (refer to FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82 and, thus, move the plunger arm 60 to cause the plunger head 70 to move within the reservoir system 40. When the interior volume of the reservoir system 40 is filled with fluidic media and an infusion path is provided from the reservoir system 40 to the body of a user-patient, the plunger head 70 may be moved within the reservoir system 40 to force fluidic media from the reservoir system 40 and into the infusion path, so as to deliver fluidic media to the body of the user-patient.

In various embodiments, once the reservoir system 40 has been sufficiently emptied or otherwise requires replacement, the user-patient may simply remove the durable housing 30 from the disposable housing 20, and replace the disposable portion 9, including the reservoir system 40, with a new disposable portion having a new reservoir. The durable housing 30 may be connected to the new disposable housing of the new disposable portion, and the delivery device including the new disposable portion may be secured to the skin of a user-patient, or otherwise attached to the user-patient.

In various other embodiments, rather than replacing the entire disposable portion 9 every time the reservoir system 40 is emptied, the reservoir system 40 may be refilled with fluidic media. In some embodiments, the reservoir system 40 may be refilled while remaining within the reservoir retaining portion 24 (refer to FIG. 6B) of the disposable housing 20. In addition, in various embodiments, the reservoir system 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 may include reservoir status circuitry (not shown), and the reservoir system 40 may include reservoir circuitry (not shown). In various embodiments, the reservoir circuitry stores information such as, but not limited to, at least one of (i) an identification string identifying the reservoir system 40; (ii) a manufacturer of the reservoir system 40; (iii) contents of the reservoir system 40; and (iv) an amount of contents in the reservoir system 40. In some embodiments, the delivery device 12 may include the reservoir status circuitry (not shown), and the reservoir status circuitry may be configured to read data from the reservoir circuitry (not shown) when the reservoir system 40 is inserted into the disposable portion 9.

In various embodiments, the reservoir status circuitry (not shown) may be further configured to store data to the reservoir circuitry after at least some of the contents of the reservoir system 40 have been transferred out of the reservoir system 40 to update information in the reservoir circuitry (not shown) related to an amount of contents still remaining in the reservoir system 40. In some embodiments, the reservoir status circuitry (not shown) may be configured to store data to the reservoir circuitry (not shown) to update information in the reservoir circuitry (not shown) related to an amount of contents remaining in the reservoir system 40 when the reservoir system 40 is inserted into the disposable portion 9. In some embodiments, the delivery device 12 may include the reservoir status circuitry (not shown) and the reservoir system 40 may include the reservoir circuitry (not shown), and the reservoir status circuitry (not shown) may selectively inhibit use of the delivery device 12 or may selectively provide a warning signal based on information read by the reservoir status circuitry (not shown) from the reservoir circuitry (not shown).

In addition, embodiments may be configured to establish a contiguous fluid flow passage for fluid transfer between a reservoir and the user-patient when the hollow needle or cannula is inserted into the user-patient. Needle-inserting devices according to embodiments of the present invention may be used with, connectable to and disconnectable from, or incorporated in a portion of an infusion medium delivery system. For example, a needle-inserting device may be connectable to a base structure of a pump-type delivery device for insertion of a needle, after which the needle-inserting device may be removed from the base structure, whereupon a further housing portion of the delivery device (containing components such as, but not limited to, a reservoir and pump or drive device) may be coupled to the base structure for operation.

Alternatively, the needle-inserting device may be incorporated into the further housing portion that contains other components as described above. In yet other embodiments, the needle-inserting device may be connectable to (and releasable from) or incorporated within an injection site module or other housing that connects, for example, by flexible tubing, to other components of a medical device (such as, but not limited to an infusion medium delivery device). In yet other embodiments, needle inserter devices may be configured for use with systems other than infusion medium delivery systems, such as, but not limited to sensor and monitor systems, or the like.

Figure 7A:
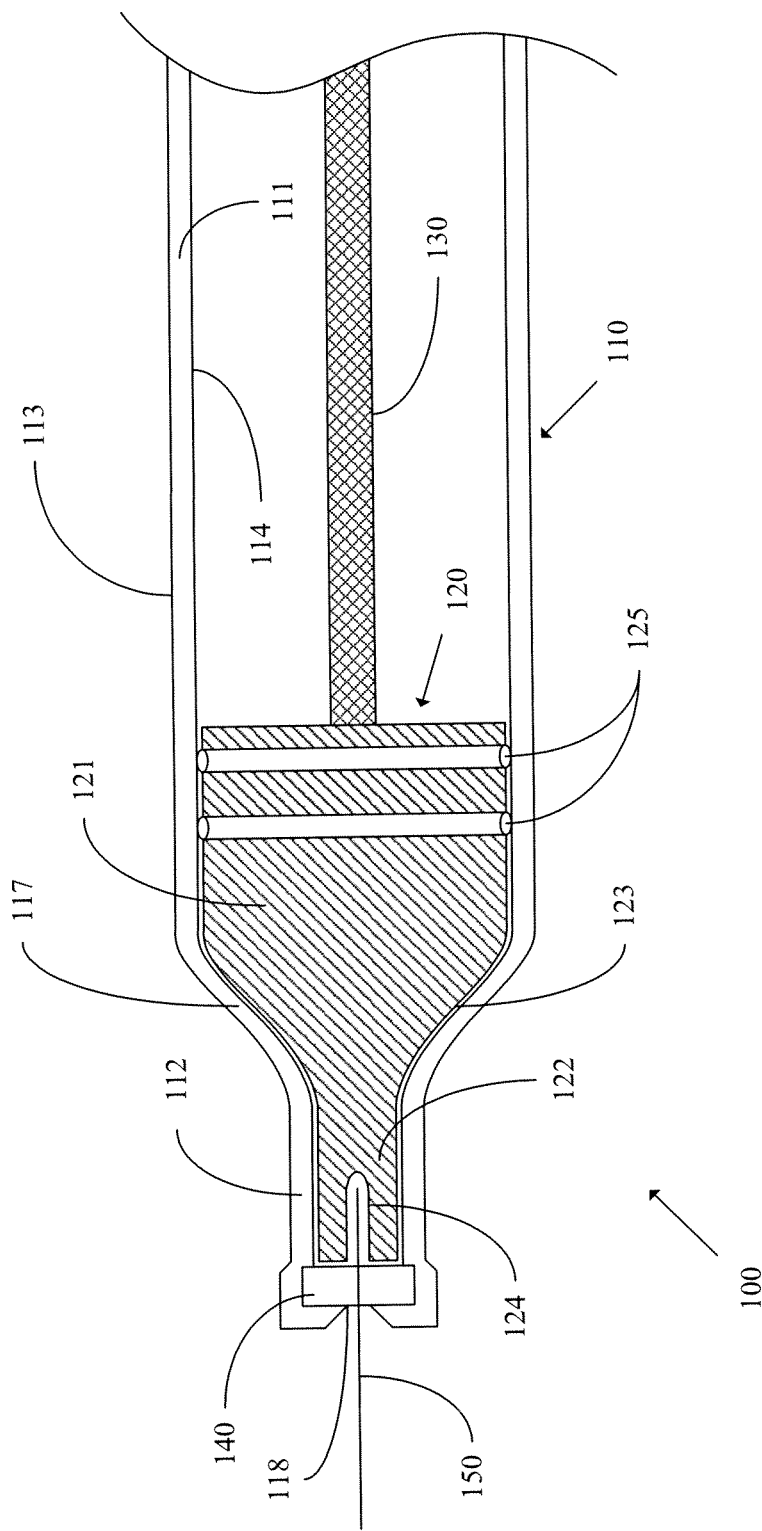
FIG. 7A illustrates a cross-sectional view of a system in accordance with an embodiment of the present invention.

FIG. 7A illustrates a cross-sectional view of a system 100 in accordance with an embodiment of the present invention. The system 100 includes a reservoir 110, a plunger head 120, a plunger arm 130, and a septum 140. In various embodiments, the system 100 further includes a needle 150. In some embodiments, the system 100 may further include similar elements as elements of embodiments of the delivery device 12 (refer to FIGS. 2 and 3), in which case the reservoir 110 would correspond to the reservoir 40 (refer to FIGS. 2, 3, and 6C). In various embodiments, the reservoir 110 may be made of a material, such as but not limited to a suitable metal, plastic, ceramic, glass, composite material, or the like. In various embodiments, the plunger head 120 may be made of a suitably rigid material such as, but not limited to, metal, plastic, ceramic, glass, composite material, or the like. In various other embodiments, the plunger head 120 may be made of a compressible material such as, but not limited to, an elastically compressible plastic, rubber, silicone, or the like.

In various embodiments, the reservoir 110 includes a reservoir body portion 111, a body headspace or neck portion 112, and a curved or sloped portion 117 that connects the reservoir body portion 111 and the neck portion 112. The reservoir 110 has an outer surface 113 and an inner surface 114. The inner surface 114 of the reservoir 110 defines a hollow interior of the reservoir 110, and the hollow interior of the reservoir 110 is able to contain a fluidic medium. The reservoir 110 further includes a port 118 at an end of the neck portion 112, through which the fluidic medium may be filled into or expelled from the hollow interior of the reservoir 110. The reservoir body portion 111 of the reservoir 110 may have any suitable shape and may have, for example, a cylinder shape, a tube shape, a barrel shape, a spherical shape, a shape with a rectangular cross-section, or the like. Similarly, the neck portion 112 of the reservoir 110 may have any suitable shape and may have, for example, a cylinder shape, a tube shape, a barrel shape, a spherical shape, a shape with a rectangular cross-section, or the like.

The plunger head 120 is located within the reservoir 110, and is moveable in an axial direction of the reservoir 110, to expand or contract an interior volume of the reservoir 110 in which a fluidic medium may be contained. The plunger head 120 is connected to the plunger arm 130, such that movement of the plunger arm 130 in the axial direction of the reservoir 110 causes movement of the plunger head 120 in the axial direction of the reservoir 110. The plunger head 120 includes a plunger body portion 121, a plunger headspace or neck portion 122, and a plunger curved or sloped portion 123 that connects the plunger body portion 121 and the plunger neck portion 122. In various embodiments, the plunger head 120 further includes one or more seals 125 that surround a portion of the plunger body portion 121.

The plunger body portion 121 is shaped such that a contour of an outer surface of the plunger body portion 121 substantially matches or is substantially the same as a contour of an inner surface of the reservoir body portion 111 of the reservoir 110. In various embodiments, the plunger body portion 121 has a diameter that is slightly smaller than a diameter of the inner surface of the reservoir body portion 111 of the reservoir 110, such that the plunger head 120 is able to slide within the reservoir 110. In some embodiments, the one or more seals 125 on the plunger body portion 121 are in contact with the inner surface of the reservoir body portion 111 of the reservoir 110 when the plunger head 120 is within the reservoir 110.

The plunger neck portion 122 is shaped such that a contour of an outer surface of the plunger neck portion 122 substantially matches or is substantially the same as a contour of an inner surface of the neck portion 112 of the reservoir 110. In various embodiments, the plunger neck portion 122 has a diameter that is slightly smaller than a diameter of the inner surface of the neck portion 112 of the reservoir 110, such that the plunger neck portion 122 is able to slide within the neck portion 112 of the reservoir 110. In some embodiments, a diameter of an outer surface of the plunger neck portion 122 closely matches or substantially matches a diameter of an inner surface of the neck portion 112 of the reservoir 110. Also, in some embodiments, the plunger neck portion 122 is shaped such that the plunger neck portion 122 substantially fills an area within the neck portion 112 of the reservoir 110 when the plunger head 120 is fully advanced within the reservoir 110. The plunger sloped portion 123 is shaped such that a contour of an outer surface of the plunger sloped portion 123 substantially matches or is substantially the same as a contour of an inner surface of the sloped portion 117 of the reservoir 110.

The septum 140 is located at the port 118 of the reservoir 110. The septum 140 may be formed of a suitable material, such as, but not limited to, rubber, silicone rubber, polyurethane, or other materials that may be pierced by a needle and form a seal around a needle. The neck portion 112 has a certain length from an end of the sloped portion 117 to the septum 140. In various embodiments, the plunger neck portion 122 has a length that is substantially the same as the certain length of the neck portion 112 of the reservoir 110. In some such embodiments, the plunger neck portion 122 is able to extend substantially all of the way into the neck portion 112 of the reservoir 110 when the plunger head 120 is fully advanced within the reservoir 110. Thus, in some embodiments, an end of the plunger neck portion 122 may be close to or in contact with the septum 140 when the plunger head 120 is fully advanced within the reservoir 110. In various embodiments, a length of the plunger neck portion 122 from an end of the plunger neck portion 122 to the plunger sloped portion 123 substantially matches a length of the neck portion 112 of the reservoir 110 from the septum 140 to the sloped portion 117 of the reservoir 110.

The septum 140 is able to be pierced by the needle 150, such as to allow for a fluidic medium to be passed through the needle 150 and into the hollow interior of the reservoir 110. In various embodiments, the plunger head 120 includes a hole or a channel or a relief or a cavity 124 that is able to accommodate a portion of the needle 150 when the plunger head 120 is sufficiently advanced within the reservoir 110 and the septum 140 is pierced by the needle 150. The cavity 124 may have any suitable shape for accommodating a portion of the needle 150, and may have, for example, a cylindrical shape, a tube shape with a half-sphere bottom, a shape with a rectangular cross-section, or the like. In various embodiments, a diameter of the cavity 124 is larger than a diameter of the needle 150, such that an end of the needle 150 is able to fit within the cavity 124.

In various embodiments, the cavity 124 is in the plunger neck portion 122 of the plunger head 120. In some embodiments, a length of the cavity 124 in the plunger neck portion 122 in a direction from the septum 140 toward the plunger body portion 121 is greater than one-quarter of a length of the plunger neck portion 122. Also, in some embodiments, the cavity 124 is positioned at a center of an end surface of the plunger neck portion 122. In some embodiments, the cavity 124 is positioned off-center at an end surface of the plunger neck portion 122. In various embodiments, an end of the neck portion 112 of the reservoir 110 partially covers the septum 140, such that the needle 150 may only pierce the septum 140 in a location that is aligned with the cavity 124 of the plunger head 120.

Figure 8:
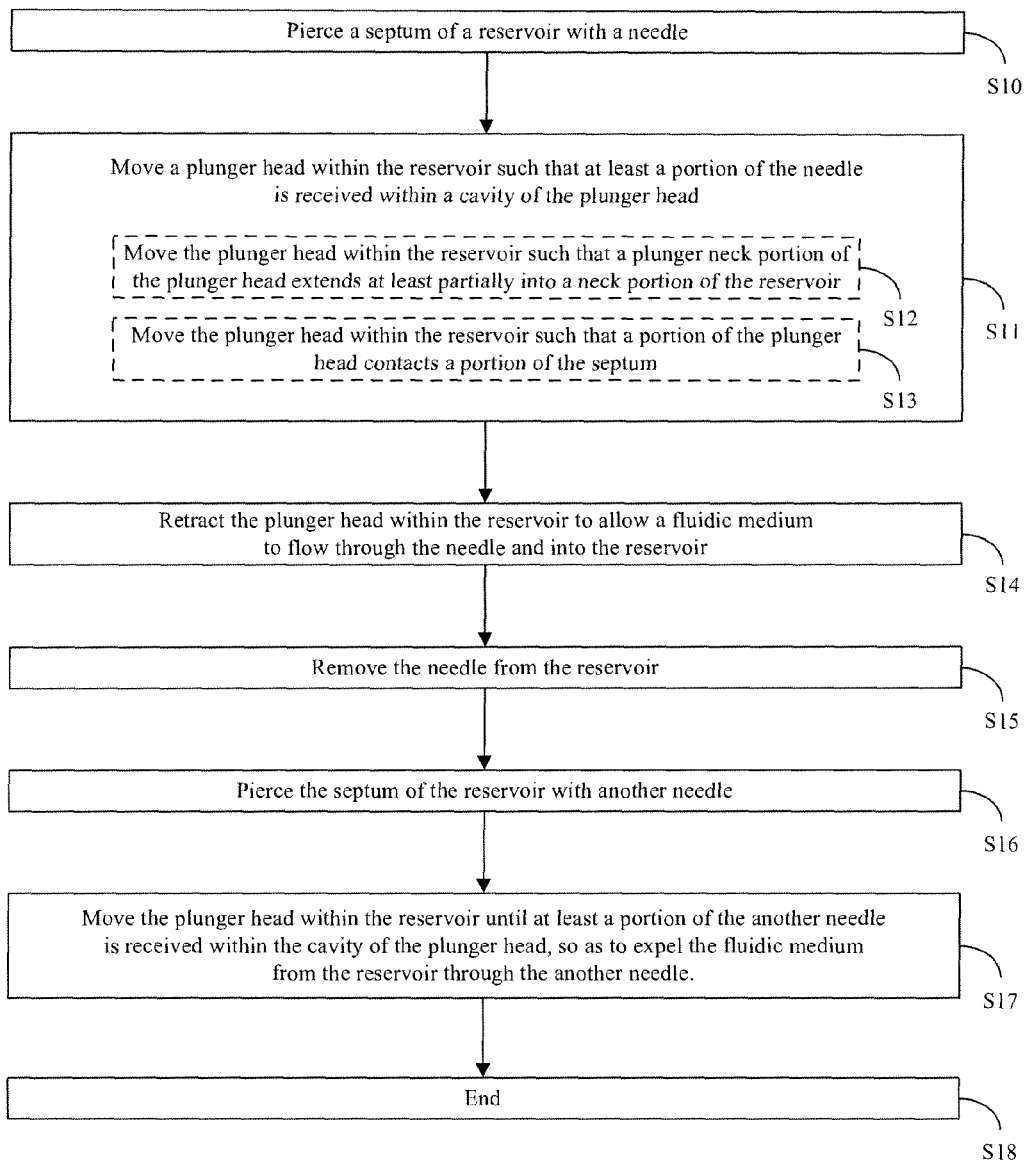
FIG. 8 illustrates a flowchart for a method in accordance with an embodiment of the present invention.

FIG. 8 illustrates a flowchart for a method in accordance with an embodiment of the present invention. With reference to FIGS. 7A and 8, in various embodiments the method of FIG. 8 allows for filling the reservoir 110 with a fluidic medium and for expelling the fluidic medium from the reservoir 110. In S10, the septum 140 of the reservoir 110 is pierced with the needle 150, and the method continues to S11. In S11, the plunger head 120 is advanced within the reservoir 110, such that at least a portion of the needle 150 is received within the cavity 124 of the plunger head 120. For example, the plunger arm 130 may be driven by a motor (not shown in FIG. 7A) or by a force applied by a user to advance the plunger head 120 within the reservoir 110. In various embodiments, moving the plunger head 120 includes moving the plunger head 120 within the reservoir 110 such that the plunger neck portion 122 extends at least partially into the neck portion 112 of the reservoir 110 (S12). Also, in various embodiments, moving the plunger head 120 includes moving the plunger head 120 within the reservoir 110 such that a portion of the plunger head 120 contacts a portion of the septum 140 (S13). In some embodiments, S10 and S11 are performed in a reverse order, such that the plunger head 120 is moved and then the septum 140 is pierced with the needle 150.

When the plunger head 120 is sufficiently advanced within the reservoir 110, a portion of the needle 150 may extend into the cavity 124 of the plunger neck portion 122, which may allow the plunger neck portion 122 to extend substantially all the way to the septum 140. As a consequence, a presence of air pockets between an end of the plunger head 120 and the septum 140 is able to be substantially limited or eliminated when the plunger head 120 is fully advanced within the reservoir 110. Reducing air pockets between the plunger head 120 and the septum 140 prior to filling the reservoir 110 is beneficial, because it limits an amount of air bubbles that subsequently enter the fluidic medium when the fluidic medium is drawn into the reservoir 110.

Figure 7B:
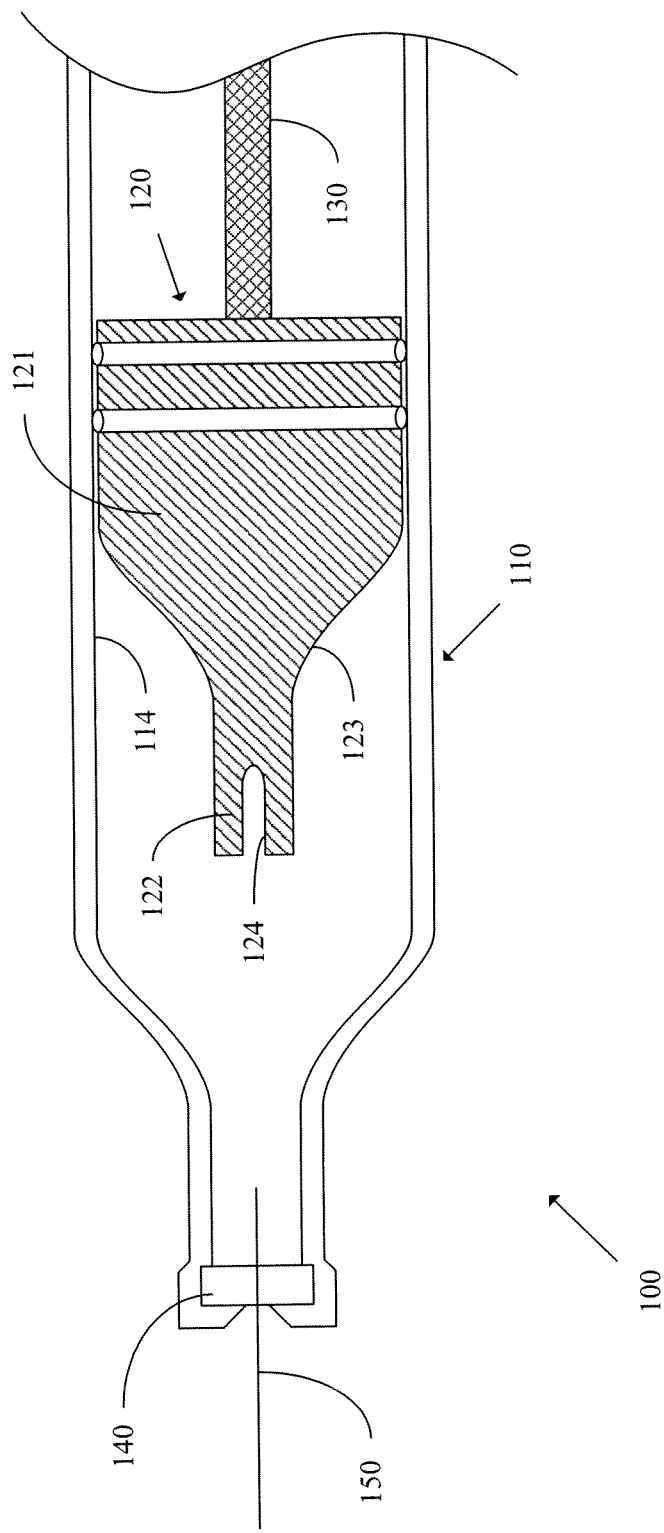
FIG. 7B illustrates a cross-sectional view of a system in accordance with an embodiment of the present invention.

In various embodiments, the method then continues to S14. In S14, the plunger head 120 is retracted within the reservoir 110 to allow a fluidic medium to flow through the needle 150 and into the reservoir 110. For example, the plunger arm 130 may be retracted by a motor (not shown in FIG. 7A) or by a pulling force exerted by a user to cause the plunger head 120 to retract within the reservoir 110. FIG. 7B illustrates a cross-sectional view of the system 100 in accordance with an embodiment of the present invention when the plunger head 120 has been partially retracted within the reservoir 110. By retracting the plunger head 120 within the reservoir 110, the fluidic medium is able to pass through the needle 150 and into the hollow interior of the reservoir 110. For example, one end of the needle 150 may be in the reservoir 110, and another end of the needle 150 may be in a vial (not shown in FIG. 7B) or other container that stores the fluidic medium, and the fluidic medium may pass from the vial to the reservoir 110 through the needle 150. In some embodiments, the needle 150 is part of a transfer guard or other similar device. Because an amount of air in the reservoir 110 was limited prior to filling the reservoir 110, an amount of air bubbles in the fluidic medium is also limited when the fluidic medium is filled into the reservoir 110. Limiting or reducing a presence of air bubbles in the fluidic medium is beneficial, because it limits an amount of air bubbles that are later expelled from the reservoir 110 into a patient or user, and thus helps to improve a delivery accuracy when delivering a specified amount of the fluidic medium to a user.

With reference to FIGS. 7A, 7B, and 8, the method of FIG. 8 may then continue to S15 in which the needle 150 is removed from the reservoir 110. In various embodiments, the septum 140 is a self-healing septum, and when the needle 150 is removed from the reservoir 110 and the septum 140, the septum 140 closes such that the fluidic medium is contained within the reservoir 110. The method may then continue to S16. In S16, the septum 140 of the reservoir 110 is pierced with another needle. For example, the septum 140 of the reservoir 110 may be pierced with a needle of a connector of an infusion path, such as a needle of the connector 56 (refer to FIG. 2) of the infusion path 50 (refer to FIG. 2). The method then continues to S17.

In S17, the plunger head 120 is advanced within the reservoir 110 until at least a portion of the another needle is received within the cavity of the plunger head 120, so as to expel the fluidic medium from the reservoir 110 through the another needle. FIG. 7A illustrates the system 100 when the plunger head 120 has been substantially fully advanced within the reservoir 110. When the plunger head 120 is advanced within the reservoir 110, the close fitting contour of the plunger head 120 to the interior surface of the reservoir 110 limits or reduces a volume of wasted fluidic medium that remains in the reservoir 110. Thus, by having a plunger head 120 with a plunger neck portion 122 that is shaped to very closely fit within the neck portion 112 of the reservoir 110 when the plunger head 120 is fully advanced, a presence of air bubbles in a fluidic medium may be limited during filling of the reservoir 110, and a volume of wasted fluidic medium may be reduced when the fluidic medium is expelled from the reservoir 110. The method then ends in S18.

Figure 7C:
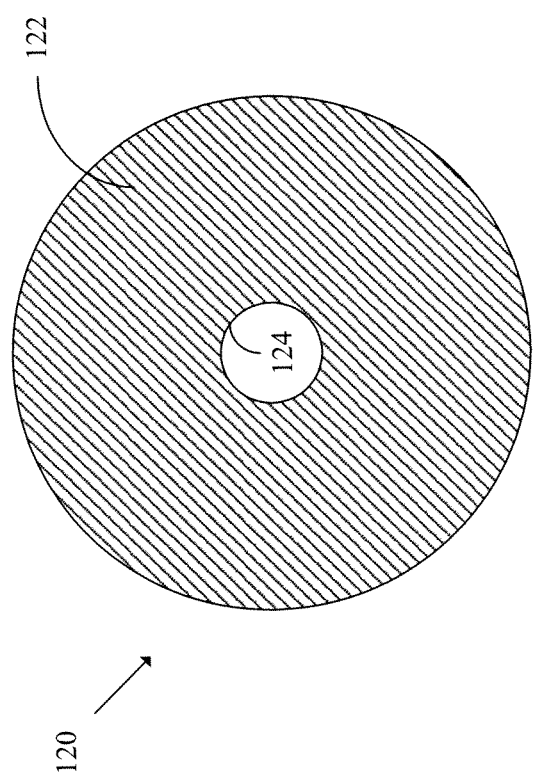
FIG. 7C illustrates a cross-sectional view from a front direction of a plunger neck portion of a plunger head in accordance with an embodiment of the present invention.

FIG. 7C illustrates a cross-sectional view from a front direction of the plunger neck portion 122 of the plunger head 120 in accordance with an embodiment of the present invention. The plunger neck portion 122 includes the cavity 124 for accommodating a needle. In various embodiments, the cavity 124 is positioned substantially near a center of a face of the plunger neck portion 122. FIG. 7D illustrates a side view of the plunger head 120 in accordance with an embodiment of the present invention. The plunger head 120 includes the plunger body portion 121, the plunger neck portion 122, and the plunger sloped portion 123. In various embodiments, the plunger body portion 121 includes one or more depressions or cavities 126 in which the one or more seals 125 (refer to FIG. 7A) may be placed.

FIGS. 9A, 10A, 11A, 12A, 12C, 14A, 14B, 15A, 16, and 17 illustrate systems in accordance with various embodiments of the present invention that include reservoirs with geometries that allow for capturing air bubbles so as to reduce a number of air bubbles that are delivered with a fluidic medium. Such systems allow for air bubble management since they have bubble trapping shapes and, by reducing a number of air bubbles that are delivered with a fluidic medium, such systems may be able to improve a delivery accuracy when attempting to deliver a specified volume of the fluidic medium. Thus, such systems provide reservoir geometries that allow for capturing a greater amount of air bubbles than with standard reservoir geometries, so that the captured air bubbles remain in the reservoir and are not dispensed with the fluidic medium.

In some embodiments, the systems in FIGS. 9A, 10A, 11A, 12A, 12C, 13A, 14A, 14B, 15A, 16, and 17 may include similar elements as elements of embodiments of the delivery device 12 (refer to FIGS. 2 and 3), in which case the reservoirs in those systems would correspond to the reservoir 40 (refer to FIGS. 2, 3, and 6C). In various embodiments, reservoirs of the systems in FIGS. 9A, 10A, 11A, 12A, 12C, 13A, 14A, 14B, 15A, 16, and 17 may be made of a material, such as but not limited to a suitable metal, plastic, ceramic, glass, composite material, TOPAS® polymer (or any other cyclic olefin copolymer (or polymer)), or the like. In various embodiments, the plunger heads of the systems in those figures may be made of a suitably rigid material such as, but not limited to, metal, plastic, ceramic, glass, composite material, or the like. In various other embodiments, the plunger heads in those systems may be made of a compressible material such as, but not limited to, an elastically compressible plastic, rubber, silicone, or the like.

Figure 9A:
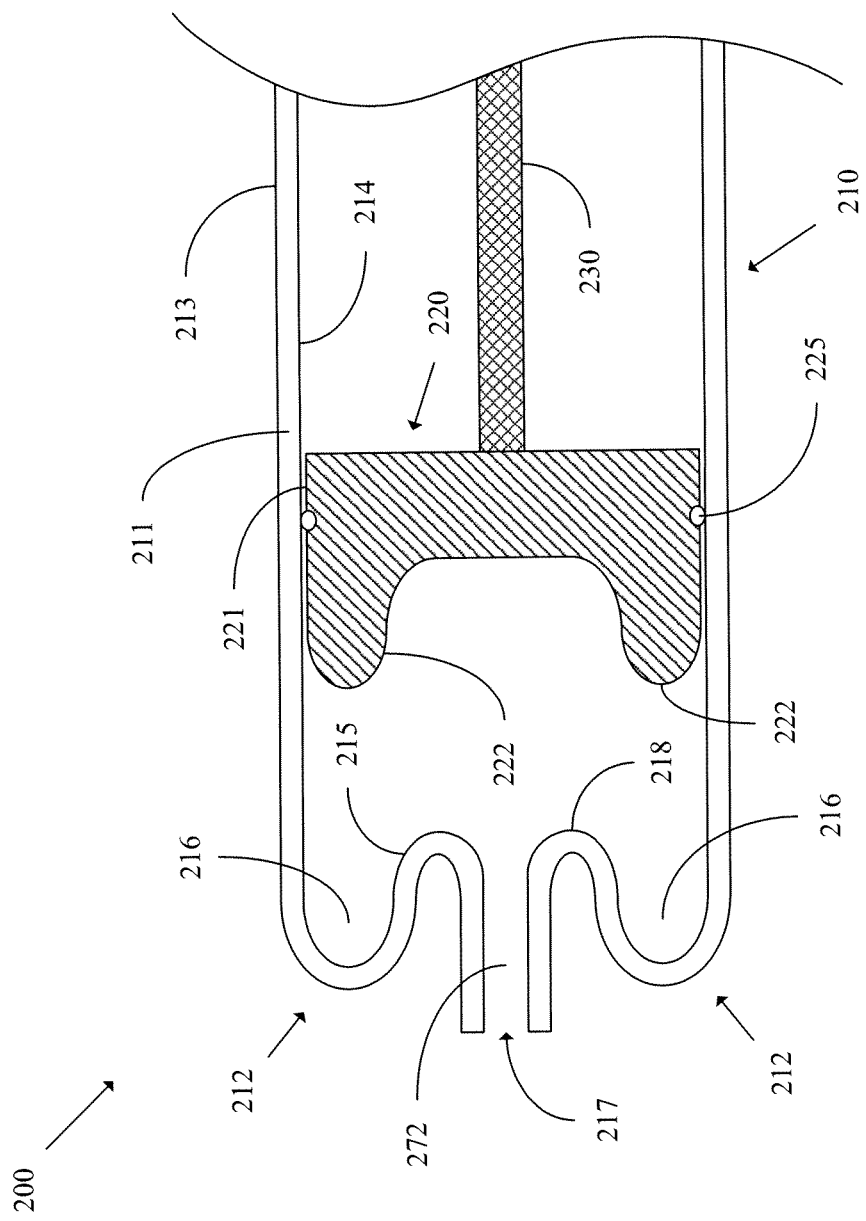
FIG. 9A illustrates a cross-sectional view of a system in accordance with an embodiment of the present invention.

FIG. 9A illustrates a cross-sectional view of a system 200 in accordance with an embodiment of the present invention. The system 200 includes a reservoir 210, a plunger head 220, and a plunger arm 230. The reservoir 210 includes a reservoir body portion 211, a bubble trap portion 212, and a port 217. The reservoir 210 has an outer surface 213 and an inner surface 214. The inner surface 214 of the reservoir 210 defines a hollow interior of the reservoir 210, and the hollow interior of the reservoir 210 is able to contain a fluidic medium. The port 217 of the reservoir 210 allows for the fluidic medium to be filled into or expelled from the hollow interior of the reservoir 210. The reservoir body portion 211 of the reservoir 210 may have any suitable shape, such as but not limited to, a cylinder shape, a tube shape, a barrel shape, a spherical shape, a shape with a rectangular cross-section, or the like.

The plunger head 220 is located within the reservoir 210, and is moveable in an axial direction of the reservoir 210, to expand or contract a volume of the reservoir 210 in which a fluidic medium may be contained. The plunger head 220 is connected to the plunger arm 230, such that movement of the plunger arm 230 in the axial direction of the reservoir 210 causes movement of the plunger head 220 in the axial direction of the reservoir 210. The plunger head 220 includes a plunger body portion 221 and a plunger protruding portion 222. In various embodiments, the plunger head 220 further includes one or more seals 225 that surround a portion of the plunger body portion 221. In various embodiments, the one or more seals 225 may be made of any suitable material, such as but not limited to, rubber, plastic, composite material, or the like.

The bubble trap portion 212 of the reservoir 210 is shaped to have a volume 216 within an interior of the reservoir 210, such that air bubbles in a fluidic medium may be trapped in the volume 216 when the fluidic medium is expelled from the reservoir 210 through the port 217. In various embodiments, an interior surface of the bubble trap portion 212 is curved or angled near the port 217, so as to define the volume 216. In some embodiments, the bubble trap portion 212 extends from the reservoir body portion 211 of the reservoir 210 past a point 218 of the reservoir 210 where a fluidic medium from an interior volume of the reservoir body portion 211 is able to move into an area or channel 272 of the reservoir 210 that leads to the port 217.

In various embodiments, the reservoir 210 is shaped such that as the plunger head 220 is advanced within the reservoir 210, a fluidic medium is able to pass through the port 217 while air bubbles in the reservoir 210 collect in the volume 216 defined by a curved or angled surface of the bubble trap portion 212 of the reservoir 210. Such a geometry of the reservoir 210 allows for decreasing an amount of air bubbles that are delivered with a fluidic medium as compared with traditional reservoir geometries. In some embodiments, the bubble trap portion 212 of the reservoir 210 is curved outward from an interior volume defined by the reservoir body portion 211, and a fluidic medium is able to pass directly from the interior volume defined by the reservoir body portion 211 to the port 217. In some embodiments, a surface 215 of the bubble trap portion 212 of the reservoir 210 includes a surface finish or material such that air bubbles substantially do not stick to the surface 215 and are shunted away from the port 217 toward the volume 216. In various embodiments, such a surface finish or material includes a hydrophobic material, a hydrophilic material, or other suitable material.

The plunger body portion 221 is shaped such that a contour of the plunger body portion 221 substantially matches or is substantially the same as an inner contour of the reservoir body portion 211 of the reservoir 210. In various embodiments, the plunger body portion 221 has a diameter that is slightly smaller than a diameter of the inner surface of the reservoir body portion 211 of the reservoir 210, such that the plunger head 220 is able to slide within the reservoir 210. In some embodiments, a seal 225 on the plunger body portion 221 is in contact with the inner surface of the reservoir body portion 211 of the reservoir 210 when the plunger head 220 is within the reservoir 210.

In various embodiments, the plunger protruding portion 222 is shaped such that a contour of the plunger protruding portion 222 substantially matches or is substantially the same as an inner contour of the bubble trap portion 212 of the reservoir 210. In some embodiments, the plunger protruding portion 222 is curved and protrudes from the plunger body portion 221. In various embodiments, the plunger protruding portion 222 has a size that is slightly smaller than a region defined by the inner surface of the bubble trap portion 212 of the reservoir 210, such that the plunger protruding portion 222 is able to slide within the volume 216 of the reservoir 210, and such that a space for a dead volume of air is left when the plunger head 220 is fully advanced within the reservoir 210. Thus, in various embodiments, the geometry of the reservoir 210 and the plunger head 220 allow for capturing air bubbles in a volume 216 of the bubble trap portion 212 when a fluidic medium is being expelled from the port 217 of the reservoir 210.

In various embodiments, the plunger protruding portion 222 has a size such that when the plunger head 220 is fully advanced within the reservoir 210, the plunger protruding portion 222 substantially fills the volume 216 of the bubble trap portion 212. Also, in various embodiments, the plunger protruding portion 222 fills less than all of the volume 216 of the bubble trap portion 212 when the plunger head 220 is fully advanced within the reservoir 210, so that one or more air pockets for holding air exist between the plunger protruding portion 222 and an inner surface of the bubble trap portion 212 when the plunger head 220 is fully advanced within the reservoir 210. In some embodiments, the plunger protruding portion 222 extends at least partially into the volume 216 of the bubble trap portion 212 when the plunger head 220 is sufficiently advanced within the reservoir 210.

Figure 9B:
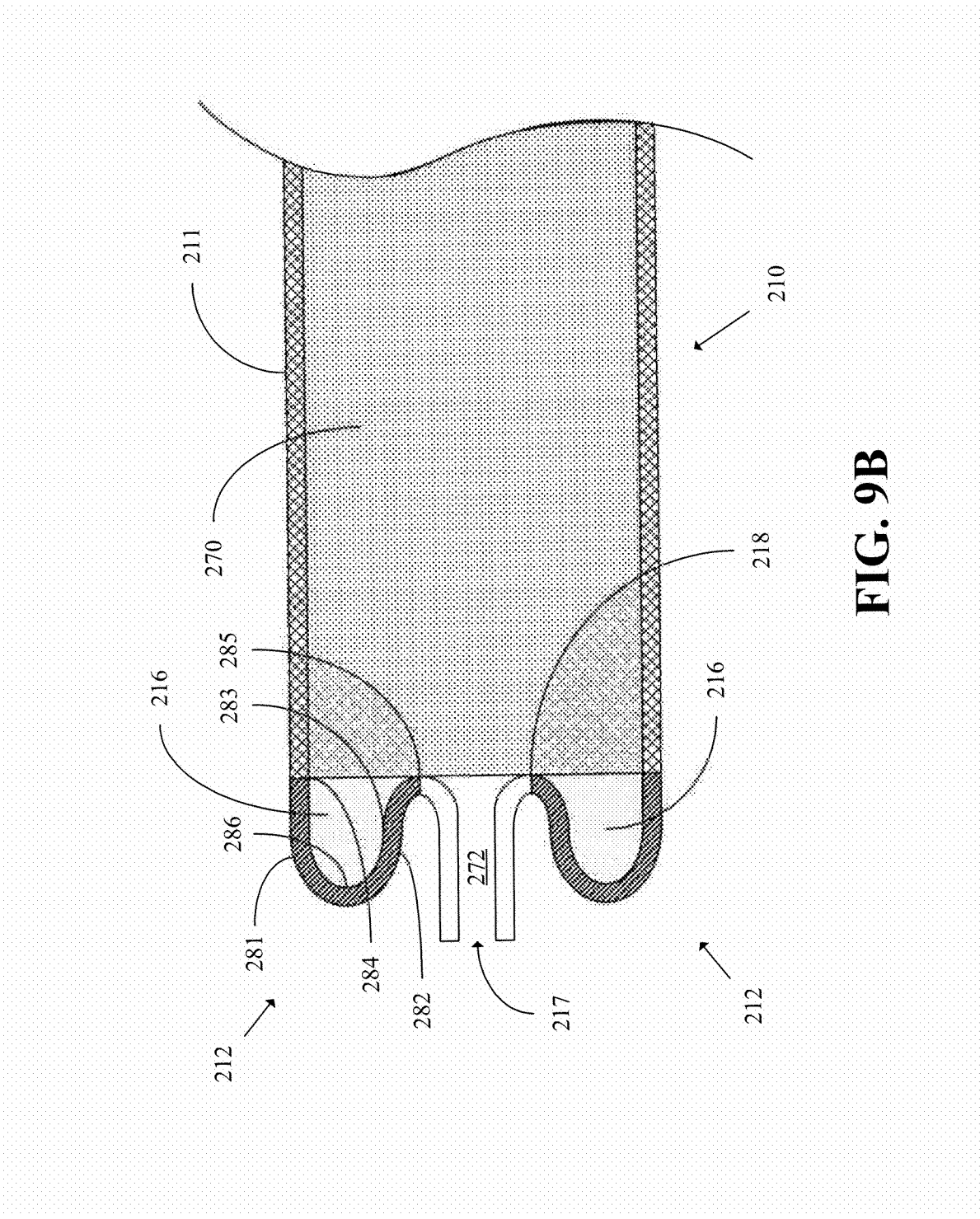
FIG. 9B illustrates a cross-sectional view of a reservoir in accordance with an embodiment of the present invention.

FIG. 9B illustrates a cross-sectional view of the reservoir 210 in accordance with an embodiment of the present invention. FIG. 9B is shaded to highlight various features of the reservoir 210. The reservoir 210 includes the reservoir body portion 211, the bubble trap portion 212, and the port 217. The reservoir body portion 211 has an interior volume 270 for containing a fluidic medium. The port 217 is in fluid flow communication with the interior volume 270 of the reservoir body portion 211. The bubble trap portion 212 has the volume 216 in fluid flow communication with the interior volume 270 of the reservoir body portion 211 for trapping air bubbles that are in the fluidic medium as the fluidic medium is being expelled from the interior volume 270.

In various embodiments, the port 217 is located to a particular side of the interior volume 270, and the bubble trap portion 212 is located to the particular side of the interior volume 270. Also, in various embodiments, the bubble trap portion 212 has a first portion 281 that extends from the reservoir body portion 211 away from the interior volume 270, and a second portion 282 that returns back toward the interior volume 270. In some embodiments, the reservoir body portion 211 and the bubble trap portion 212 are formed together as a single seamless unit. Also, in some embodiments, the first portion 281 of the bubble trap portion 212 extends from the reservoir body portion 211 away from the interior volume 270 and the second portion 282 of the bubble trap portion 212 extends from the first portion 281 toward the interior volume 270.

In various embodiments, the bubble trap portion 212 includes a curved surface 283 having a first end region 284, a second end region 285, and a middle region 286 between the first end region 284 and the second end region 285. In some embodiments, the first end region 284 and the second end region 285 are closer to the interior volume 270 of the reservoir body portion 211 than the middle region 286 is to the interior volume 270. Also, in some embodiments, the first end region 284 is in contact with the reservoir body portion 211, and the second end region 285 is located adjacent to the interior volume 270 of the reservoir body portion 211.

In various embodiments, the curved surface 283 of the bubble trap portion 212 is in contact with the fluidic medium when the fluidic medium is in the volume 216 of the bubble trap portion 212. In further embodiments, the curved surface 283 is approximately U-shaped. FIG. 9B illustrates a cross-sectional view, but in three-dimensions the bubble trap portion 212 may be shaped, for example, approximately as a semi-toroid. In various embodiments, the reservoir 210 is shaped such that in order for a fluidic medium to flow from the volume 216 of the bubble trap portion 212 to the port 217, the fluidic medium must flow through the interior volume 270 of the reservoir body portion 211. In some embodiments, the reservoir 210 includes the channel 272 that leads from the interior volume 270 of the reservoir body portion 211 to the port 217, and the bubble trap portion 212 encircles at least a portion of the channel 272.

Figure 10A:
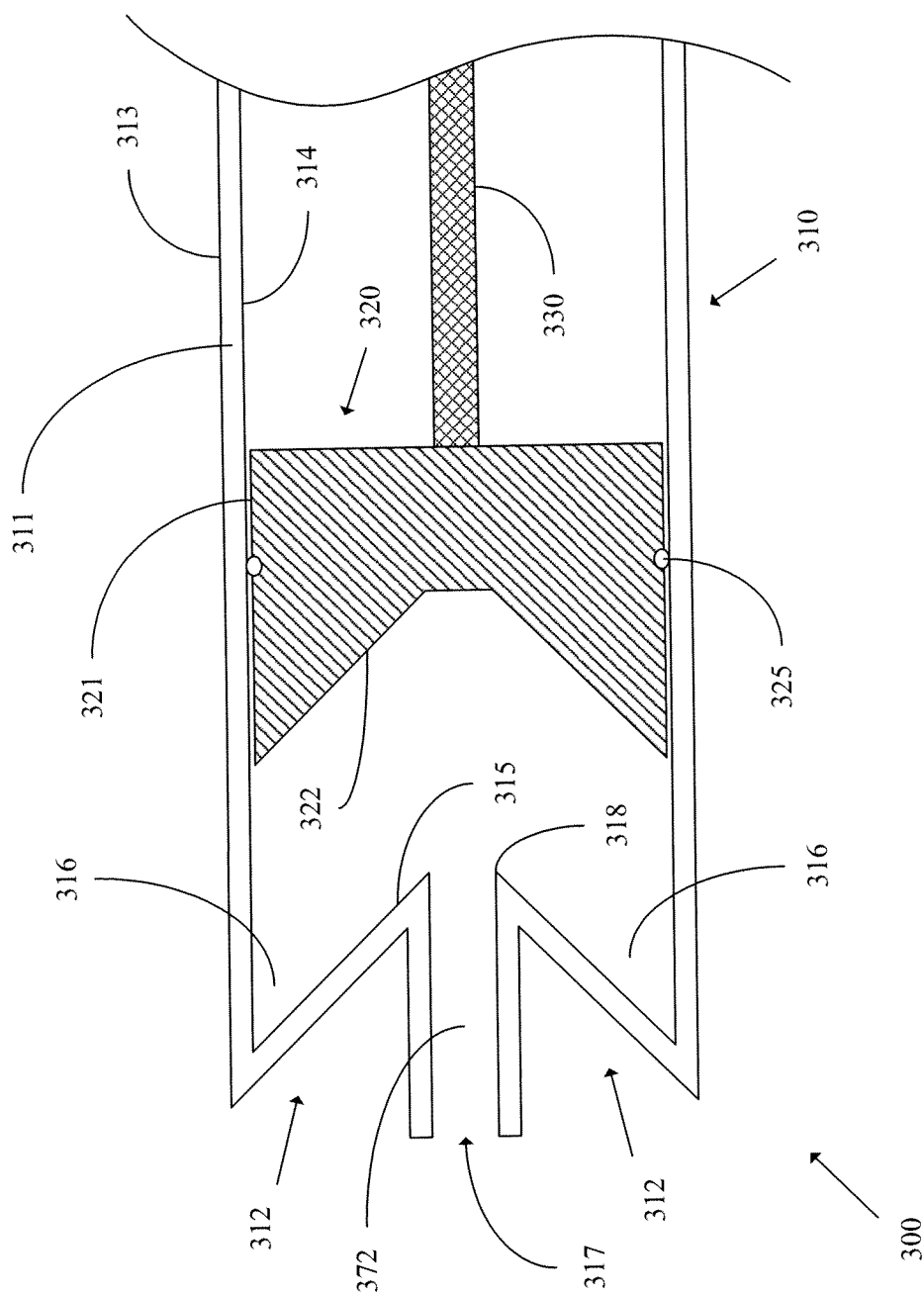
FIG. 10A illustrates a cross-sectional view of a system in accordance with an embodiment of the present invention.

FIG. 10A illustrates a cross-sectional view of a system 300 in accordance with an embodiment of the present invention. The system 300 includes a reservoir 310, a plunger head 320, and a plunger arm 330. The reservoir 310 includes a reservoir body portion 311, a bubble trap portion 312, and a port 317. The reservoir 310 has an outer surface 313 and an inner surface 314. The inner surface 314 of the reservoir 310 defines a hollow interior of the reservoir 310, and the hollow interior of the reservoir 310 is able to contain a fluidic medium. The port 317 of the reservoir 310 allows for the fluidic medium to be filled into or expelled from the hollow interior of the reservoir 310. The reservoir body portion 311 of the reservoir 310 may have any suitable shape, such as but not limited to, a cylinder shape, a tube shape, a barrel shape, a spherical shape, a shape with a rectangular cross-section, or the like.

The plunger head 320 is located within the reservoir 310, and is moveable in an axial direction of the reservoir 310, to expand or contract a volume of the reservoir 310 in which a fluidic medium may be contained. The plunger head 320 is connected to the plunger arm 330, such that movement of the plunger arm 330 in the axial direction of the reservoir 310 causes movement of the plunger head 320 in the axial direction of the reservoir 310. The plunger head 320 includes a plunger body portion 321 and a plunger protruding portion 322. In various embodiments, the plunger head 320 further includes one or more seals 325 that surround a portion of the plunger body portion 321.

The bubble trap portion 312 of the reservoir 310 is shaped so as to form a volume 316 within an interior of the reservoir 310, such that air bubbles in a fluidic medium may be trapped in the volume 316 of the bubble trap portion 312 when the fluidic medium is expelled from the reservoir 310 through the port 317. In various embodiments, an interior surface of the bubble trap portion 312 is angled at a substantially straight angle near the port 317, so as to define the volume 316. In some embodiments, the bubble trap portion 312 extends from the reservoir body portion 311 of the reservoir 310 past a point 318 of the reservoir 310 where a fluidic medium from an interior volume of the reservoir body portion 311 is able to move into an area or channel 372 of the reservoir 310 that leads to the port 317.

In various embodiments, the reservoir 310 is shaped such that as the plunger head 320 is advanced within the reservoir 310, a fluidic medium is able to pass through the port 317 while air bubbles in the reservoir 310 collect in the volume 316 defined by a substantially straight angled surface of the bubble trap portion 312 of the reservoir 310. Such a geometry of the reservoir 310 may allow for decreasing an amount of air bubbles that are delivered with a fluidic medium as compared with traditional reservoir geometries. In some embodiments, the bubble trap portion 312 of the reservoir 310 is angled outward from an interior region of the reservoir 310 defined by the reservoir body portion 311, and a fluidic medium is able to pass directly from the interior region of the reservoir 310 defined by the reservoir body portion 311 to the port 317. In some embodiments, a surface 315 of the bubble trap portion 312 of the reservoir 310 includes a surface finish or material such that air bubbles substantially do no stick to the surface 315 and are shunted away from the port 317 toward the volume 316.

The plunger body portion 321 is shaped such that a contour of the plunger body portion 321 substantially matches or is substantially the same as a contour of an inner surface of the reservoir body portion 311 of the reservoir 310. In various embodiments, the plunger body portion 321 has a diameter that is slightly smaller than a diameter of the inner surface of the reservoir body portion 311 of the reservoir 310, such that the plunger head 320 is able to slide within the reservoir 310. In some embodiments, the one or more seals 325 on the plunger body portion 321 are in contact with the inner surface of the reservoir body portion 311 of the reservoir 310 when the plunger head 320 is within the reservoir 310.

In various embodiments, the plunger protruding portion 322 is shaped such that a contour of the plunger protruding portion 322 substantially matches or is substantially the same as an inner contour of the bubble trap portion 312 of the reservoir 310. In some embodiments, the plunger protruding portion 322 is angled from the plunger body portion 321 at a substantially straight angle and protrudes from the plunger body portion 321. In various embodiments, the plunger protruding portion 322 has a size that is slightly smaller than a region defined by the inner surface of the bubble trap portion 312 of the reservoir 310, such that the plunger protruding portion 322 is able to slide within the volume 316 of the bubble trap portion 312, and such that a space for a dead volume of air is left when the plunger head 320 is fully advanced within the reservoir 310. Thus, in various embodiments, the geometry of the reservoir 310 and the plunger head 320 allow for capturing air bubbles in a volume 316 of the bubble trap portion 312 when a fluidic medium is being expelled from the port 317 of the reservoir 310.

In various embodiments, the plunger protruding portion 322 has a size such that when the plunger head 320 is fully advanced within the reservoir 310, the plunger protruding portion 322 substantially fills the volume 316 of the bubble trap portion 312. Also, in various embodiments, the plunger protruding portion 322 fills less than all of the volume 316 of the bubble trap portion 312 when the plunger head 320 is fully advanced within the reservoir 310, so that one or more air pockets for holding air exist between the plunger protruding portion 322 and an inner surface of the bubble trap portion 312 when the plunger head 320 is fully advanced within the reservoir 310. In some embodiments, the plunger protruding portion 322 extends at least partially into the volume 316 of the bubble trap portion 312 when the plunger head 320 is sufficiently advanced within the reservoir 310.

FIG. 10B illustrates a cross-sectional view of the reservoir 310 in accordance with an embodiment of the present invention. FIG. 10B is shaded to highlight various features of the reservoir 310. The reservoir 310 includes the reservoir body portion 311, the bubble trap portion 312, and the port 317. The reservoir body portion 311 has an interior volume 370 for containing a fluidic medium. The port 317 is in fluid flow communication with the interior volume 370 of the reservoir body portion 311. The bubble trap portion 312 has the volume 316 in fluid flow communication with the interior volume 370 of the reservoir body portion 311 for trapping air bubbles that are in the fluidic medium as the fluidic medium is being expelled from the interior volume 370.

In various embodiments, the port 317 is located to a particular side of the interior volume 370, and the bubble trap portion 312 is located to the particular side of the interior volume 370. Also, in various embodiments, the bubble trap portion 312 has a first portion 381 that extends from the reservoir body portion 311 away from the interior volume 370, and a second portion 382 that returns back toward the interior volume 370. In some embodiments, the reservoir body portion 311 and the bubble trap portion 312 are formed together as a single seamless unit. Also, in some embodiments, the first portion 381 of the bubble trap portion 312 extends from the reservoir body portion 311 away from the interior volume 370 and the second portion 382 of the bubble trap portion 312 extends from the first portion 381 toward the interior volume 370.

In various embodiments, the reservoir 310 is shaped such that in order for a fluidic medium to flow from the volume 316 of the bubble trap portion 312 to the port 317, the fluidic medium must flow through the interior volume 370 of the reservoir body portion 311. In some embodiments, the reservoir 310 includes the channel 372 that leads from the interior volume 370 of the reservoir body portion 311 to the port 317, and the bubble trap portion 312 encircles at least a portion of the channel 372.

In various embodiments, the bubble trap portion 312 includes a first surface 383 that defines an edge of the volume 316 of the bubble trap portion 312, and a second surface 384 that defines another edge of the volume 316 of the bubble trap portion 312, where the second surface 384 is positioned at an angle with respect to the first surface 383. In some embodiments, the angle between the first surface 383 and the second surface 384 is less than 90 degrees. Also, in some embodiments, the first surface 383 is planar with respect to an inner surface of the reservoir body portion 311 of the reservoir 310. In various embodiments, the port 317 is located to a particular side of the interior volume 370 and the first portion 381 of the bubble trap portion 312 extends from the reservoir body portion 311 to the particular side.

Figure 11A:
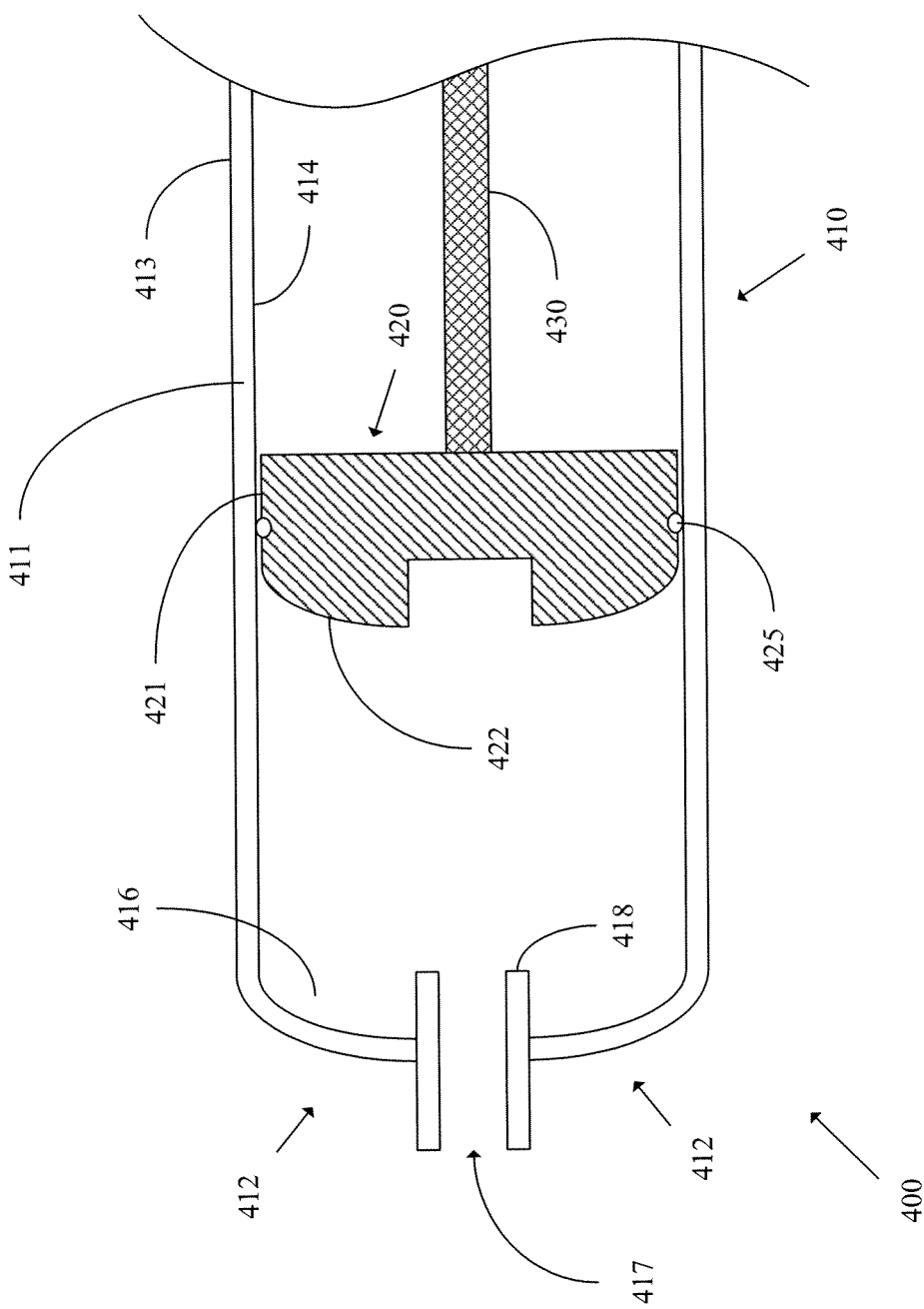
FIG. 11A illustrates a cross-sectional view of a system in accordance with an embodiment of the present invention.

FIG. 11A illustrates a cross-sectional view of a system 400 in accordance with an embodiment of the present invention. The system 400 includes a reservoir 410, a plunger head 420, and a plunger arm 430. The reservoir 410 includes a reservoir body portion 411, a bubble trap portion 412, and a port 417. The reservoir 410 has an outer surface 413 and an inner surface 414. The inner surface 414 of the reservoir 410 defines a hollow interior of the reservoir 410, and the hollow interior of the reservoir 410 is able to contain a fluidic medium. The port 417 of the reservoir 410 allows for the fluidic medium to be filled into or expelled from the hollow interior of the reservoir 410. The reservoir body portion 411 of the reservoir 410 may have any suitable shape, such as but not limited to, a cylinder shape, a tube shape, a barrel shape, a spherical shape, a shape with a rectangular cross-section, or the like.

The plunger head 420 is located within the reservoir 410, and is moveable in an axial direction of the reservoir 410, to expand or contract a volume of the reservoir 410 in which a fluidic medium may be contained. The plunger head 420 is connected to the plunger arm 430, such that movement of the plunger arm 430 in the axial direction of the reservoir 410 causes movement of the plunger head 420 in the axial direction of the reservoir 410. The plunger head 420 includes a plunger body portion 421 and a plunger protruding portion 422. In various embodiments, the plunger head 420 further includes one or more seals 425 that surround a portion of the plunger body portion 421.

The bubble trap portion 412 of the reservoir 410 is shaped so as to form a volume 416 within an interior of the reservoir 410, such that air bubbles in a fluidic medium may be trapped in the volume 416 of the bubble trap portion 412 when the fluidic medium is expelled from the reservoir 410 through the port 417. In various embodiments, the reservoir 410 is shaped such that as the plunger head 420 is advanced within the reservoir 410, a fluidic medium is able to pass through the port 417 while air bubbles in the reservoir 410 collect in the volume 416 of the reservoir 410. Such a geometry of the reservoir 410 may allow for decreasing an amount of air bubbles that are delivered with a fluidic medium as compared with traditional reservoir geometries.

The plunger body portion 421 is shaped such that a contour of an outer surface of the plunger body portion 421 substantially matches or is substantially the same as a contour of an inner surface of the reservoir body portion 411 of the reservoir 410. In various embodiments, the plunger body portion 421 has a diameter that is slightly smaller than a diameter of the inner surface of the reservoir body portion 411 of the reservoir 410, such that the plunger head 420 is able to slide within the reservoir 410. In some embodiments, the one or more seals 425 on the plunger body portion 421 are in contact with the inner surface of the reservoir body portion 411 of the reservoir 410 when the plunger head 420 is within the reservoir 410. In various embodiments, the plunger protruding portion 422 is shaped such that a contour of an outer surface of the plunger protruding portion 422 substantially matches or is substantially the same as a contour of an inner surface of the bubble trap portion 412 of the reservoir 410.

Figure 11B:
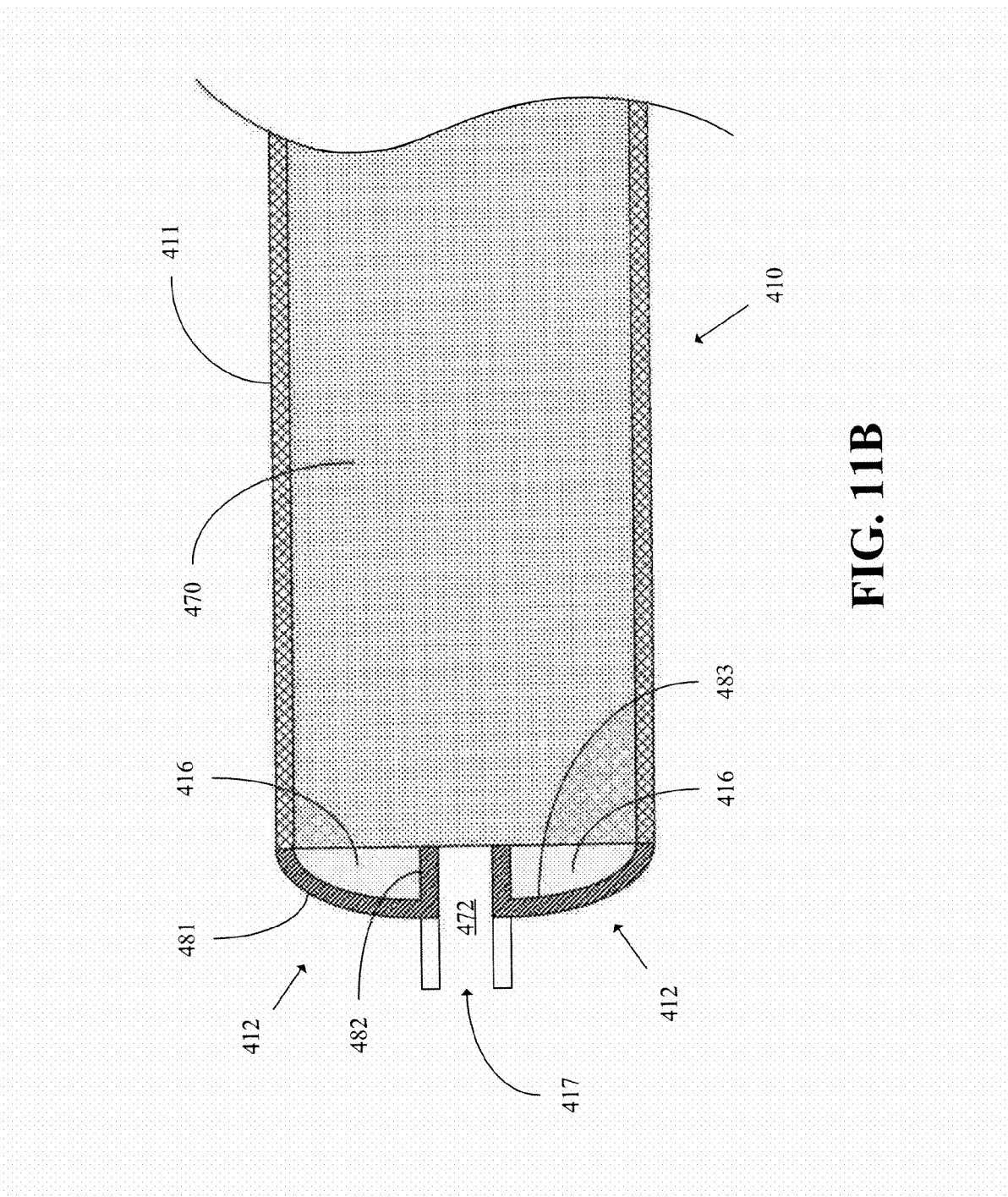
FIG. 11B illustrates a cross-sectional view of a reservoir in accordance with an embodiment of the present invention.

FIG. 11B illustrates a cross-sectional view of the reservoir 410 in accordance with an embodiment of the present invention. FIG. 11B is shaded to highlight various features of the reservoir 410. The reservoir 410 includes the reservoir body portion 411, the bubble trap portion 412, and the port 417. The reservoir body portion 411 has an interior volume 470 for containing a fluidic medium. The port 417 is in fluid flow communication with the interior volume 470 of the reservoir body portion 411. The bubble trap portion 412 has the volume 416 in fluid flow communication with the interior volume 470 of the reservoir body portion 411 for trapping air bubbles that are in the fluidic medium as the fluidic medium is being expelled from the interior volume 470.

In various embodiments, the port 417 is located to a particular side of the interior volume 470, and the bubble trap portion 412 is located to the particular side of the interior volume 470. Also, in various embodiments, the bubble trap portion 412 has a first portion 481 that extends from the reservoir body portion 411 away from the interior volume 470, and a second portion 482 that returns back toward the interior volume 470. In some embodiments, the reservoir body portion 411 and the bubble trap portion 412 are formed together as a single seamless unit. Also, in some embodiments, the first portion 481 of the bubble trap portion 412 extends from the reservoir body portion 411 away from the interior volume 470 and the second portion 482 of the bubble trap portion 412 extends from the first portion 481 toward the interior volume 470.

In various embodiments, the bubble trap portion 412 includes a curved surface 483. In some embodiments, the curved surface 483 of the bubble trap portion 412 is in contact with the fluidic medium when the fluidic medium is in the volume 416 of the bubble trap portion 412. In various embodiments, the reservoir 410 is shaped such that in order for a fluidic medium to flow from the volume 416 of the bubble trap portion 412 to the port 417, the fluidic medium must flow through the interior volume 470 of the reservoir body portion 411. In some embodiments, the reservoir 410 includes a channel 472 that leads from the interior volume 470 of the reservoir body portion 411 to the port 417, and the bubble trap portion 412 encircles at least a portion of the channel 472.

With reference to FIGS. 11A and 11B, in various embodiments, the plunger protruding portion 422 is shaped such that a contour of the plunger protruding portion 422 substantially matches or is substantially the same as an inner contour of the bubble trap portion 412 of the reservoir 410. In some embodiments, the plunger protruding portion 422 is at least partially curved and protrudes from the plunger body portion 421. Also, in some embodiments, the plunger protruding porting includes a surface that is substantially parallel to an inner surface of the reservoir body portion 411 of the reservoir 410. In various embodiments, the plunger protruding portion 422 has a size that is slightly smaller than a region defined by the inner surface of the bubble trap portion 412 of the reservoir 410, such that the plunger protruding portion 422 is able to slide within the volume 416 of the reservoir 410, and such that a space for a dead volume of air is left when the plunger head 420 is fully advanced within the reservoir 410. Thus, in various embodiments, the geometry of the reservoir 410 and the plunger head 420 allow for capturing air bubbles in a volume 416 of the bubble trap portion 412 when a fluidic medium is being expelled from the port 417 of the reservoir 410.

In various embodiments, the plunger protruding portion 422 has a size such that when the plunger head 420 is fully advanced within the reservoir 410, the plunger protruding portion 422 substantially fills the volume 416 of the bubble trap portion 412. Also, in various embodiments, the plunger protruding portion 422 fills less than all of the volume 416 of the bubble trap portion 412 when the plunger head 420 is fully advanced within the reservoir 410, so that one or more air pockets for holding air exist between the plunger protruding portion 422 and an inner surface of the bubble trap portion 412 when the plunger head 420 is fully advanced within the reservoir 410. In some embodiments, the plunger protruding portion 422 extends at least partially into the volume 416 of the bubble trap portion 412 when the plunger head 420 is sufficiently advanced within the reservoir 410.

Figure 12A:
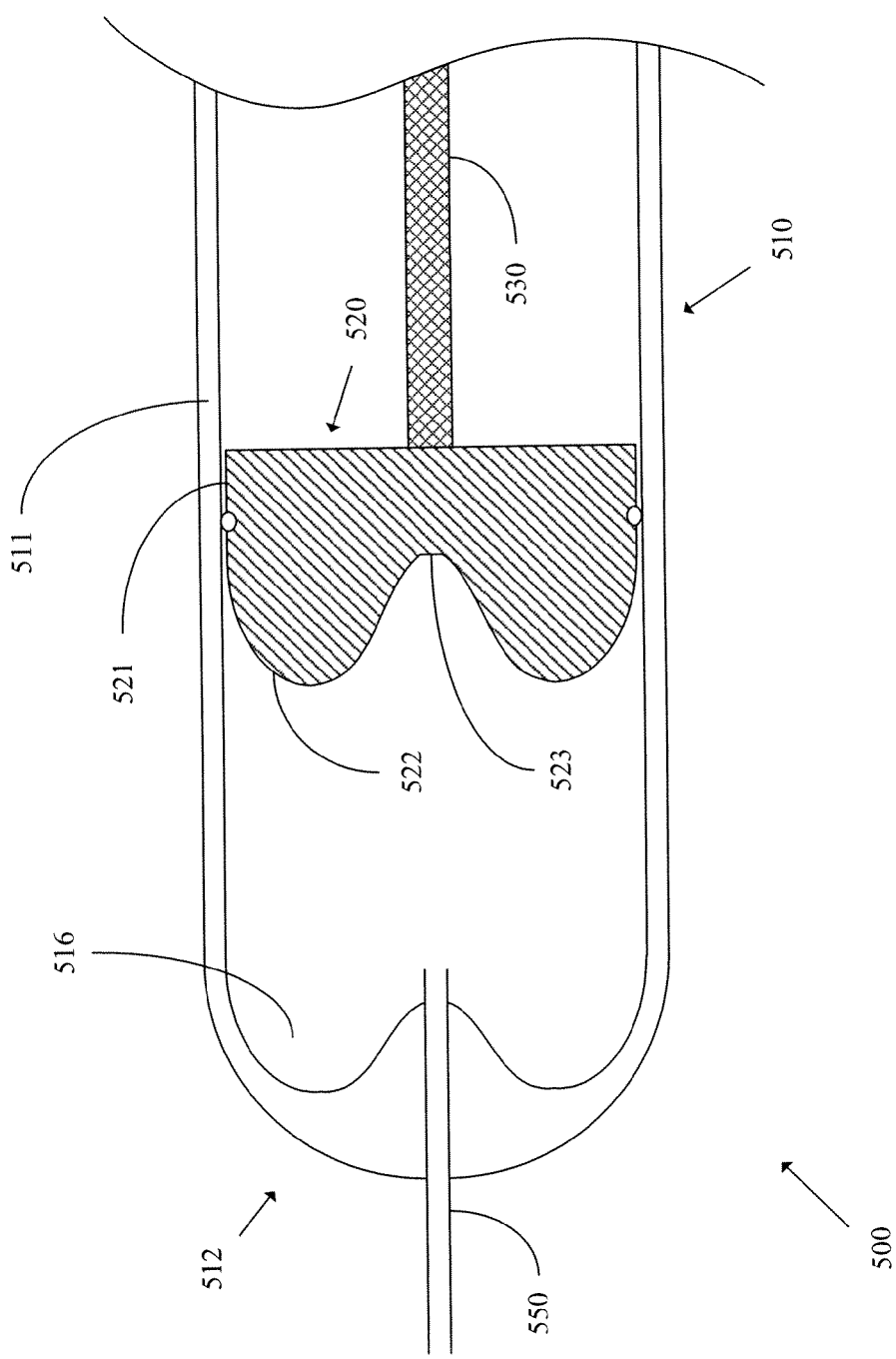
FIG. 12A illustrates a cross-sectional view of a system in accordance with an embodiment of the present invention.

FIG. 12A illustrates a cross-sectional view of a system 500 in accordance with an embodiment of the present invention. The system 500 includes a reservoir 510, a plunger head 520, and a plunger arm 530. In various embodiments, the system 500 further includes a needle 550. The reservoir 510 is similar to the reservoir 210 of the system 200 (refer to FIG. 9A), and includes a reservoir body portion 511 and a bubble trap portion 512. The bubble trap portion 512 defines a volume 516 for trapping air bubbles. Thus, the reservoir 510 has an air trap geometry that allows for capturing air bubbles.

The plunger head 520 is similar to the plunger head 220 of the system 200 (refer to FIG. 9A). The plunger head 520 includes a plunger body portion 521 and a plunger protruding portion 522. The plunger head 520 further includes a depression or relief 523 for allowing at least a portion of the needle 550 to be inserted into an interior of the reservoir 510 when the plunger head 520 is fully advanced within the reservoir 510. In various embodiments, the plunger head 520 has the relief 523 for receiving at least a portion of the needle 550 when the plunger head 520 is sufficiently advanced within the reservoir 510 and the portion of the needle 550 is inserted into the reservoir 510. In various embodiments, the reservoir 510 is shaped to trap air bubbles. Also, in various embodiments, the reservoir 510 and the plunger head 520 are shaped so as to minimize a delivery of air bubbles when a fluidic medium is expelled from the reservoir 510.

FIG. 12B illustrates a cross-sectional view of the reservoir 510 in accordance with an embodiment of the present invention. FIG. 12B is shaded to highlight various features of the reservoir 510. The reservoir 510 includes the reservoir body portion 511, the bubble trap portion 512, and a port 517. The reservoir body portion 511 has an interior volume 570 for containing a fluidic medium. The port 517 is in fluid flow communication with the interior volume 570 of the reservoir body portion 511. The bubble trap portion 512 has the volume 516 in fluid flow communication with the interior volume 570 of the reservoir body portion 511 for trapping air bubbles that are in the fluidic medium as the fluidic medium is being expelled from the interior volume 570.

In various embodiments, the port 517 is located to a particular side of the interior volume 570, and the bubble trap portion 512 is located to the particular side of the interior volume 570. Also, in various embodiments, the bubble trap portion 512 has a first portion 581 that extends from the reservoir body portion 511 away from the interior volume 570, and a second portion 582 that returns back toward the interior volume 570. In some embodiments, the reservoir body portion 511 and the bubble trap portion 512 are formed together as a single seamless unit. Also, in some embodiments, the first portion 581 of the bubble trap portion 512 extends from the reservoir body portion 511 away from the interior volume 570 and the second portion 582 of the bubble trap portion 512 extends from the first portion 581 toward the interior volume 570.

In various embodiments, the bubble trap portion 512 includes a curved surface 583 having a first end region 584, a second end region 585, and a middle region 586 between the first end region 584 and the second end region 585. In some embodiments, the first end region 584 and the second end region 585 are closer to the interior volume 570 of the reservoir body portion 511 than the middle region 586 is to the interior volume 570. Also, in some embodiments, the first end region 584 is in contact with the reservoir body portion 511, and the second end region 585 is located adjacent to the interior volume 570 of the reservoir body portion 511.

In various embodiments, the curved surface 583 of the bubble trap portion 512 is in contact with the fluidic medium when the fluidic medium is in the volume 516 of the bubble trap portion 512. In further embodiments, the curved surface 583 is approximately U-shaped. FIG. 9B illustrates a cross-sectional view, but in three-dimensions the bubble trap portion 512 may be shaped, for example, approximately as a semi-toroid. In various embodiments, the reservoir 510 is shaped such that in order for a fluidic medium to flow from the volume 516 of the bubble trap portion 512 to the port 517, the fluidic medium must flow through the interior volume 570 of the reservoir body portion 511. In some embodiments, the reservoir 510 includes a channel 572 that leads from the interior volume 570 of the reservoir body portion 511 to the port 517, and the bubble trap portion 512 encircles at least a portion of the channel 572.

Figure 12C:
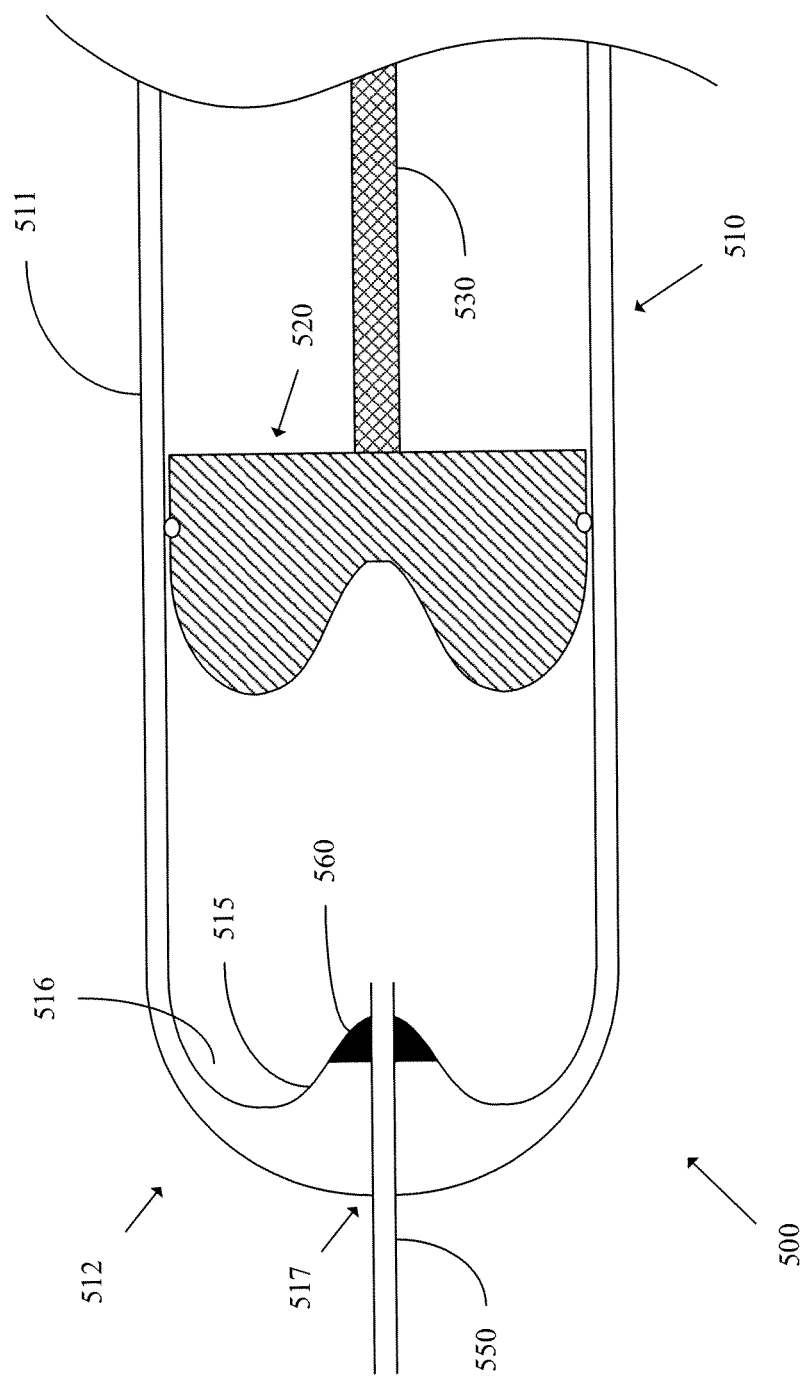
FIG. 12C illustrates a cross-sectional view of a system in accordance with an embodiment of the present invention.

FIG. 12C illustrates a cross-sectional view of the system 500 of FIG. 12A in accordance with another embodiment of the present invention. In the embodiment illustrated in FIG. 12C, the system 500 further includes a feature 560. In various embodiments, the feature 560 is located between an interior surface 515 of the bubble trap portion 512 of the reservoir 510 and a location of the reservoir 510 where a fluidic medium is able to be expelled from the reservoir 510. The feature 560 may comprise, for example, a hydrophilic material or a hydrophobic material, that will substantially keep air bubbles from being dispensed through the port 517 of the reservoir 510. As a consequence, a delivery accuracy may be able to be improved since a number of air bubbles expelled from the reservoir 510 is further limited by the feature 560. In various embodiments, the feature 560 shunts air bubbles in a fluidic medium away from the port 517 of the reservoir 510 and toward the volume 516 of the bubble trap portion 512 when the fluidic medium is being expelled from an interior volume of the reservoir body portion 511 of the reservoir 510.

Figure 13A:
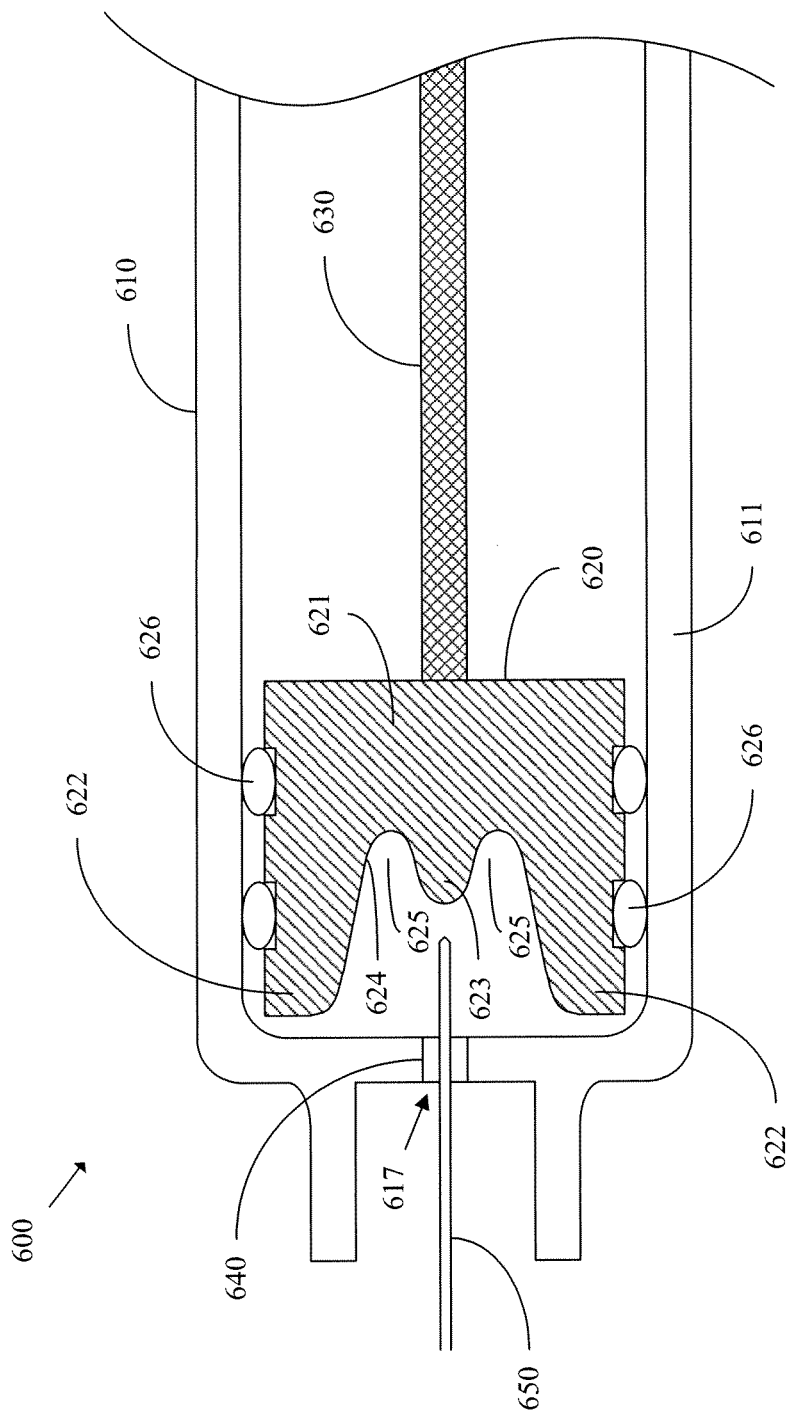
FIG. 13A illustrates a cross-sectional view of a system in accordance with an embodiment of the present invention.

FIG. 13A illustrates a cross-sectional view of a system 600 in accordance with an embodiment of the present invention. The system 600 includes a reservoir 610, a plunger head 620, and a plunger arm 630. The reservoir 610 has a hollow interior that is able to contain a fluidic medium. The reservoir 610 includes a port 617 that allows for the fluidic medium to be filled into or expelled from the hollow interior of the reservoir 610. In various embodiments, a septum 640 is located in the port 617 of the reservoir 610, where the septum 640 is able to be pierced by a needle 650. The reservoir 610 includes a reservoir body portion 611 that may have any suitable shape, such as but not limited to, a cylinder shape, a tube shape, a barrel shape, a spherical shape, a shape with a rectangular cross-section, or the like.

The plunger head 620 is located within the reservoir 610, and is moveable in an axial direction of the reservoir 610, to expand or contract a volume of the reservoir 610 in which a fluidic medium may be contained. The plunger head 620 is connected to the plunger arm 630, such that movement of the plunger arm 630 in the axial direction of the reservoir 610 causes movement of the plunger head 620 in the axial direction of the reservoir 610. The plunger head 620 is shaped to form a bubble trap region 625 for trapping air bubbles that are in the fluidic medium as the fluidic medium is expelled from the reservoir 610 by the plunger head 620. In various embodiments, the plunger head 620 includes a concave portion 624 that defines the bubble trap region 625. In various embodiments, the plunger head 620 further includes one or more seals 626 that surround a portion of the plunger head 620. In various embodiments, the one or more seals 626 may be made of any suitable material, such as but not limited to, rubber, plastic, composite material, or the like.

In various embodiments, the plunger head 620 includes a body portion 621, a first protrusion portion 622 protruding from the body portion 621, and a second protrusion portion 623 protruding from the body portion 621. In various embodiments, the bubble trap region 625 is located between the first protrusion portion 622 and the second protrusion portion 623. It should be appreciated that FIG. 13A is a cross-sectional view, and that the plunger head 620 is actually a three-dimensional object as rotated around a central axis passing in an axial direction of the reservoir 610. In various embodiments, the first protrusion portion 622 surrounds at least a portion of the second protrusion portion 623.

Figure 13B:
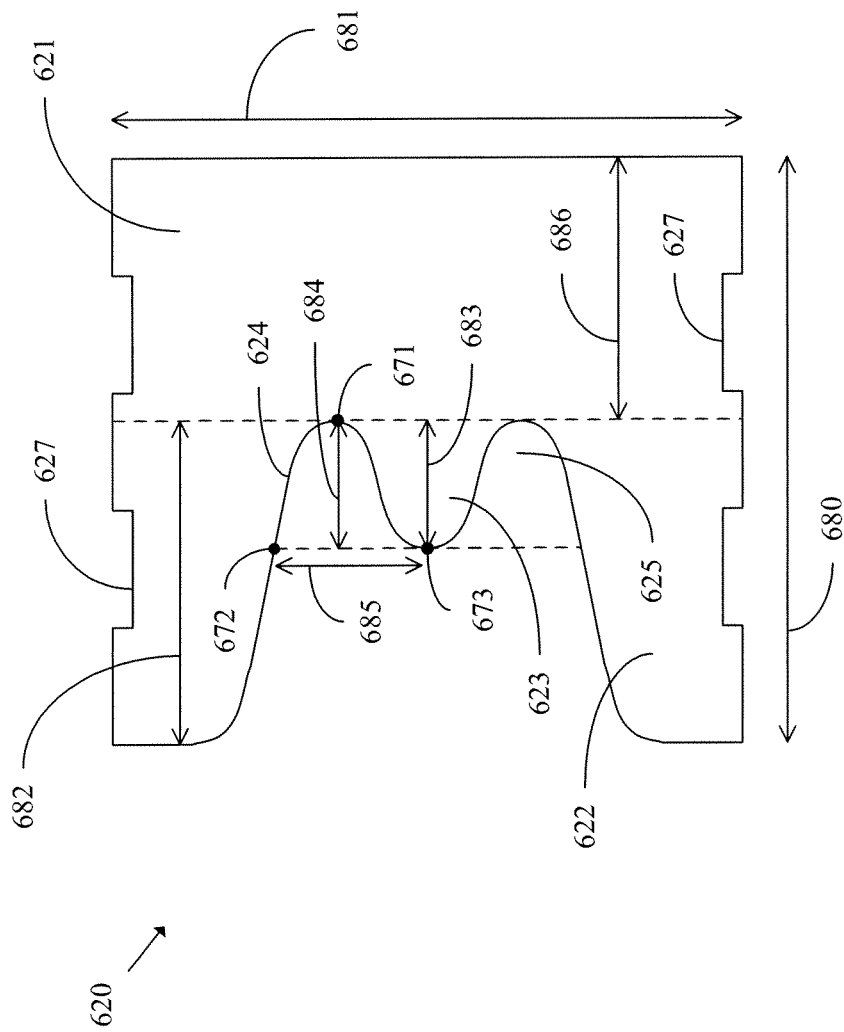
FIG. 13B illustrates a cross-sectional view of a plunger head in accordance with an embodiment of the present invention.

FIG. 13B illustrates a cross-sectional view of the plunger head 620 in accordance with an embodiment of the present invention. With reference to FIGS. 13A and 13B, in various embodiments, the first protrusion portion 622 extends a first distance 682 from the body portion 621. Also, in various embodiments, the second protrusion portion 623 extends a second distance 683 from the body portion 621. In some embodiments, the first distance 682 is greater than the second distance 683. Also, in some embodiments, the second distance 683 is greater than one-fourth of the first distance 682. In various embodiments, the second protrusion portion 623 is dome shaped.

In various embodiments, the concave portion 624 of the plunger head 620 includes a curved surface that defines the bubble trap region 625. In various embodiments, the curved surface of the concave portion 624 has a first end position 672, a second end position 673, and an innermost position 671. The first end position 672 is located on the first protrusion portion 622, and the second end position 673 is located on the second protrusion portion 623. The innermost position 671 is located at an innermost position of the concave portion 624 with respect to a depth 680 of the plunger head 620. In various embodiments, a depth 684 of the bubble trap region 625 defined by the concave portion 624 is at least greater than one-half of a width 685 of the bubble trap region 625 from the first end position 672 to the second end position 673. In various embodiments, the depth 684 of the bubble trap region 625 is greater than or equal to one-fourth of the depth 680 of the plunger head 620. In various embodiments, the body portion 621 of the plunger head 620 has a depth 686 and a width 681. In various embodiments, the plunger head 620 includes one or more seal recesses 627 in which the seals 626 are located.

A method for expelling a fluidic medium from a reservoir in accordance with an embodiment of the present invention may be performed using the system 600. In various embodiments, the plunger head 620 includes the concave portion 624 that defines the bubble trap region 625. In various embodiments, the method includes expelling the fluidic medium from the reservoir 610 using the plunger head 620, and trapping, in the bubble trap region 625 defined by the concave portion 624 of the plunger head 620, air bubbles that are in the fluidic medium as the fluidic medium is being expelled from the reservoir 610 by the plunger head 620. In various embodiments, the fluidic medium expelled from the reservoir 610 is delivered to a body of a patient through the needle 650.

Figure 14A:
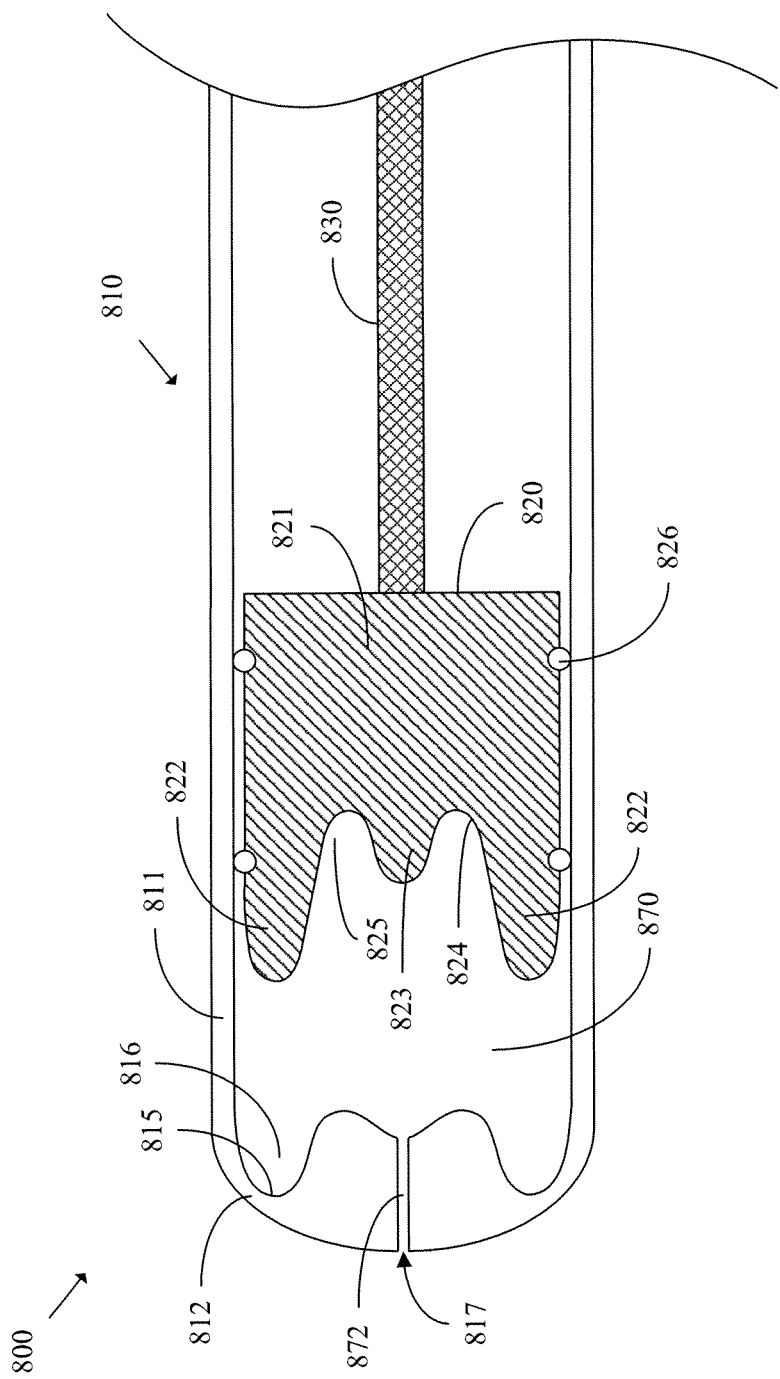
FIG. 14A illustrates a cross-sectional view of a system in accordance with an embodiment of the present invention.

FIG. 14A illustrates a cross-sectional view of a system 800 in accordance with an embodiment of the present invention. In various embodiments, the system 800 allows for delivering a fluidic medium, such as to a body of a patient. The system 800 includes a reservoir 810, a plunger head 820, and a plunger arm 830. The reservoir 810 includes a reservoir body portion 811, a reservoir bubble trap portion 812, and a port 817. The reservoir 810 has a hollow interior, and the hollow interior of the reservoir 810 is able to contain a fluidic medium. The port 817 of the reservoir 810 allows for the fluidic medium to be filled into or expelled from the hollow interior of the reservoir 810. The reservoir body portion 811 of the reservoir 810 may have any suitable shape, such as but not limited to, a cylinder shape, a tube shape, a barrel shape, a spherical shape, a shape with a rectangular cross-section, or the like.

The plunger head 820 is located within the reservoir 810, and is moveable in an axial direction of the reservoir 810, to expand or contract a volume of the reservoir 810 in which a fluidic medium may be contained. The plunger head 820 is connected to the plunger arm 830, such that movement of the plunger arm 830 in the axial direction of the reservoir 810 causes movement of the plunger head 820 in the axial direction of the reservoir 810. The plunger head 820 is shaped to form a bubble trap region 825 for trapping air bubbles that are in the fluidic medium as the fluidic medium is expelled from the reservoir 810 by the plunger head 820. In various embodiments, the plunger head 820 includes a concave portion 824 that defines the bubble trap region 825.

In various embodiments, the plunger head 820 includes a body portion 821, a first protrusion portion 822 protruding from the body portion 821, and a second protrusion portion 823 protruding from the body portion 821. In various embodiments, the bubble trap region 825 is located between the first protrusion portion 822 and the second protrusion portion 823. It should be appreciated that FIG. 14A is a cross-sectional view, and that the plunger head 820 is actually a three-dimensional object as rotated around a central axis passing in an axial direction of the reservoir 810. In various embodiments, the first protrusion portion 822 surrounds at least a portion of the second protrusion portion 823.

In various embodiments, the first protrusion portion 822 extends a first distance from the body portion 821. Also, in various embodiments, the second protrusion portion 823 extends a second distance from the body portion 821. In some embodiments, the first distance is greater than the second distance. Also, in some embodiments, the second distance is greater than one-fourth of the first distance. In various embodiments, the second protrusion portion 823 is dome shaped. In various embodiments, the concave portion 824 of the plunger head 820 includes a curved surface that defines the bubble trap region 825. In various embodiments, the curved surface of the concave portion 824 has a first end position, a second end position, and an innermost position. The first end position is located on the first protrusion portion 822, and the second end position is located on the second protrusion portion 823. The innermost position is located at an innermost position of the concave portion 824 with respect to a depth of the plunger head 820. In various embodiments, a depth of the bubble trap region 825 defined by the concave portion 824 is at least greater than one-half of a width of the bubble trap region 825 from the first end position to the second end position. In various embodiments, the depth of the bubble trap region 825 is greater than or equal to one-fourth of the depth of the plunger head 820.

The reservoir bubble trap portion 812 of the reservoir 810 is shaped to have a volume 816 within an interior of the reservoir 810, such that air bubbles in the fluidic medium may be trapped in the volume 816 when the fluidic medium is expelled from the reservoir 810 through the port 817. In various embodiments, an interior surface 815 of the reservoir bubble trap portion 812 is curved or angled near the port 817, so as to define the volume 816. In some embodiments, reservoir the bubble trap portion 812 extends from the reservoir body portion 811 of the reservoir 810 past a point of the reservoir 810 where the fluidic medium from an interior volume of the reservoir body portion 811 is able to move into an area or channel 872 of the reservoir 810 that leads to the port 817.

In various embodiments, the reservoir 810 and the plunger head 820 are shaped such that as the plunger head 820 is advanced within the reservoir 810, the fluidic medium is able to pass through the port 817 while some air bubbles in the reservoir 810 collect in the volume 816 defined by the interior surface 815 of the reservoir bubble trap portion 812 of the reservoir 810 and other air bubbles in the reservoir 810 collect in the bubble trap region 825 defined by the concave portion 824 of the plunger head 820. Such a geometry of the reservoir 810 and the plunger head 820 allows for decreasing an amount of air bubbles that are delivered with a fluidic medium as compared with traditional reservoir and plunger head geometries. In some embodiments, the reservoir bubble trap portion 812 of the reservoir 810 is curved outward from an interior volume 870 defined by the reservoir body portion 811, and a fluidic medium is able to pass directly from the interior volume 870 defined by the reservoir body portion 811 to the port 817.

In various embodiments, the body portion 821 of the plunger head 820 is shaped such that a contour of the body portion 821 substantially matches or is substantially the same as an inner contour of the reservoir body portion 811 of the reservoir 810. In various embodiments, the body portion 821 of the plunger head 820 has a diameter that is slightly smaller than a diameter of an inner surface of the reservoir body portion 811 of the reservoir 810, such that the plunger head 820 is able to slide within the reservoir 810. In some embodiments, a seal 826 on the body portion 821 of the plunger head 820 is in contact with the inner surface of the reservoir body portion 811 of the reservoir 810 when the plunger head 820 is within the reservoir 810.

In various embodiments, the reservoir body portion 811 has the interior volume 870 for containing the fluidic medium. Also, in various embodiments, the port 817 is in fluid flow communication with the interior volume 870. In various embodiments, the plunger head 820 is moveable within the reservoir 810, and the plunger head 820 is shaped to form the bubble trap region 825 for trapping air bubbles that are in the fluidic medium as the fluidic medium is being expelled from the interior volume 870 through the port 817 by the plunger head 820. Thus, in various embodiments, the geometry of the reservoir 810 and the plunger head 820 allow for capturing some air bubbles in the volume 816 of the reservoir bubble trap portion 812 and for capturing some air bubbles in the bubble trap region 825 defined by the plunger head 820 when the fluidic medium is being expelled through the port 817 of the reservoir 810.

In various embodiments, the reservoir includes the reservoir bubble trap portion 812 having the volume 816 in fluid flow communication with the interior volume 870 for trapping air bubbles that are in the fluidic medium as the fluidic medium is being expelled from the interior volume 870. In some embodiments, a contour of the first protrusion portion 822 of the plunger head 820 substantially matches an inner contour of the reservoir bubble trap portion 812. In various embodiments, the first protrusion portion 822 of the plunger head 820 is shaped and positioned such that the first protrusion portion 822 extends at least partially into the volume 816 of the reservoir bubble trap portion 812 when the plunger head 820 is sufficiently advanced within the reservoir 810. In some embodiments, the first protrusion portion 822 of the plunger head 820 is shaped and positioned such that when the plunger head 820 is fully advanced within the reservoir 810 the first protrusion portion 822 substantially fills the volume 816 of the reservoir bubble trap portion 812.

In various embodiments, the reservoir 810 is shaped such that in order for the fluidic medium to flow from the volume 816 of the reservoir bubble trap portion 812 to the port 817, the fluidic medium must flow through the interior volume 870. In some embodiments, the reservoir 810 further includes the channel 872 that leads from the interior volume 870 to the port 817. Also, in some embodiments, the reservoir bubble trap portion 812 includes a first portion that extends from the reservoir body portion 811 away from the interior volume 870, and a second portion that returns back toward the interior volume 870, where the reservoir bubble trap portion 812 encircles at least a portion of the channel 872.

With reference to FIGS. 3, 5C, 6C, and 14A, in various embodiments, the system 800 further includes the drive device 80, the disposable housing 20, and the durable housing 30, where the reservoir 810 of FIG. 14A may correspond to the reservoir 40 of FIG. 3. In some embodiments, the drive device 80 includes the drive device linkage portion 82 and the motor 84 for moving the drive device linkage portion 82. In some embodiments, the plunger arm 830 is connected to the plunger head 820, and the plunger arm 830 has a mating portion, which may include threads, teeth, or the like, for mating with the drive device linkage portion 82 of the drive device 80. In various embodiments, the disposable housing 20 allows for housing the reservoir 810 and for being secured to a user, such as the user 7 of FIG. 1. Also, in various embodiments, the durable housing 30 allows for housing the motor 84 of the drive device 80, where the durable housing 30 is configured to be selectively engaged with and disengaged from the disposable housing 20.

Figure 14B:
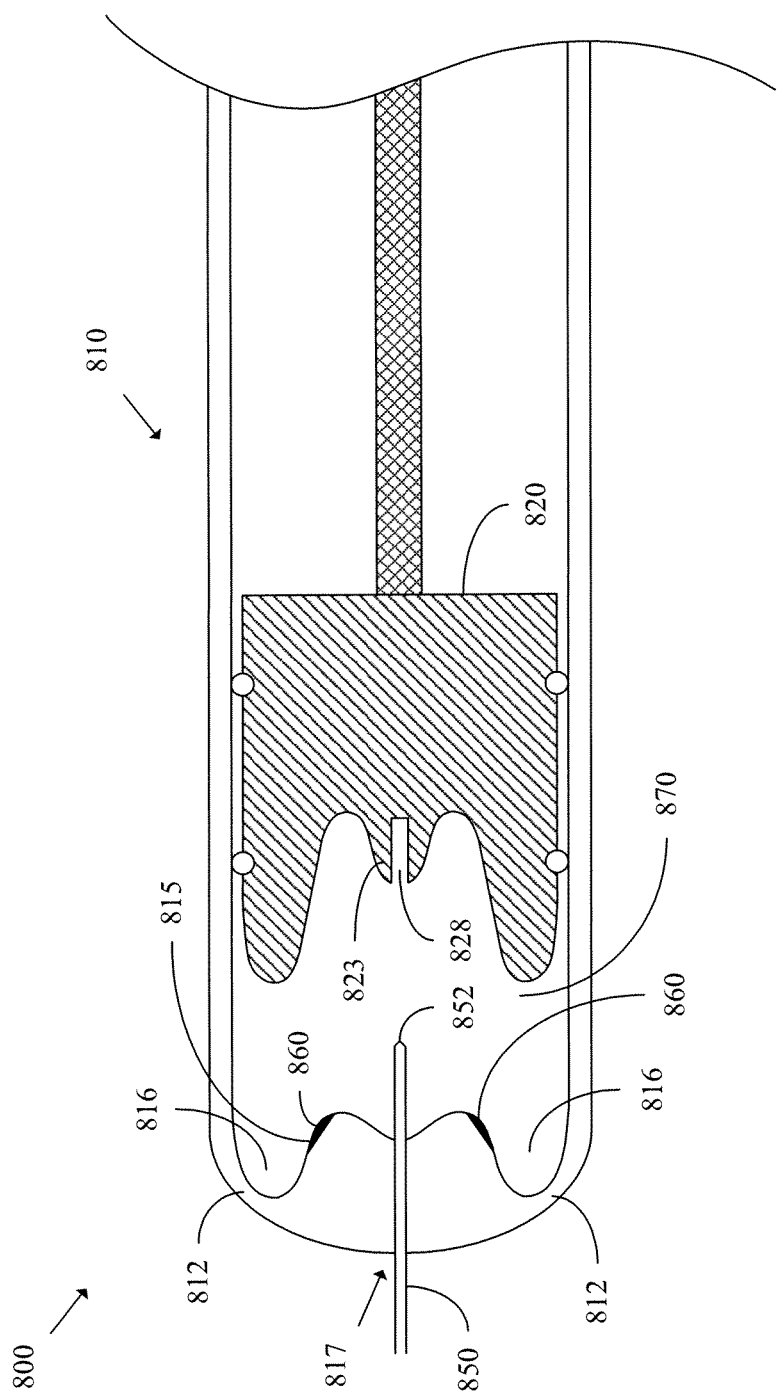
FIG. 14B illustrates a cross-sectional view of a system in accordance with an embodiment of the present invention.

FIG. 14B illustrates the system 800 in accordance with an embodiment of the present invention. In the embodiment illustrated in FIG. 14B, the second protrusion portion 823 of the plunger head 820 includes a cavity 828 for receiving a portion of a needle 850 when the plunger head 820 is sufficiently advanced within the reservoir 810. In various embodiments, the second protrusion portion 823 is aligned with the port 817, such that when the needle 850 is inserted into the port 817, an end 852 of the needle 850 is directed toward the second protrusion portion 823.

In some embodiments, the reservoir 810 includes a material 860 for shunting air bubbles in the fluidic medium away from the port 817 and toward the volume 816 of the reservoir bubble trap portion 812 when the fluidic medium is being expelled from the interior volume 870. In various embodiments, the material 860 is located on at least a portion of the interior surface 815 of the reservoir bubble trap portion 812, such that air bubbles substantially do not stick to the portion of the interior surface 815 covered with the material 860 and are shunted away from the port 817 toward the volume 816 defined by the reservoir bubble trap portion 812. In various embodiments, the material 860 includes a hydrophobic material, a hydrophilic material, or other suitable material.

FIGS. 15A-17 illustrate a system 1000 according to various embodiments of the present intention. The system 1000 may include features similar or may be employed as an embodiment of the system 100, 200, 300, 400, 500, 600, 800 (e.g., FIGS. 7A-14B) and/or any of the other embodiments described in the disclosure. Although the system 1000 may include features similar or used with the embodiments of FIGS. 7-14B, it should be understood that the system 1000 may also include some or all of the same features and operate in a manner similar to that shown and described in the embodiments of FIGS. 1-6C. In addition, some or all of the features shown in FIGS. 1-14B (and/or any of the other embodiments described in the disclosure) may be combined in various ways and included in the embodiments shown in FIGS. 15A-17. Likewise, it should be understood that any of the features of the embodiments of FIGS. 15A-17 may be combined or otherwise incorporated into any of the other embodiments of FIGS. 15A-17 as well as any other embodiment herein discussed.

The embodiments shown in FIGS. 7A-14B relate to reservoirs each having a single port through which fluidic media in the reservoir is expelled (and optionally through which the reservoir is filled). However, those embodiments may be employed with reservoirs having multiple ports, such as a first port for expelling fluidic media and a second port for receiving fluidic media. Further embodiments relating to multi-port reservoirs are discussed in the disclosure.

Figure 15A:
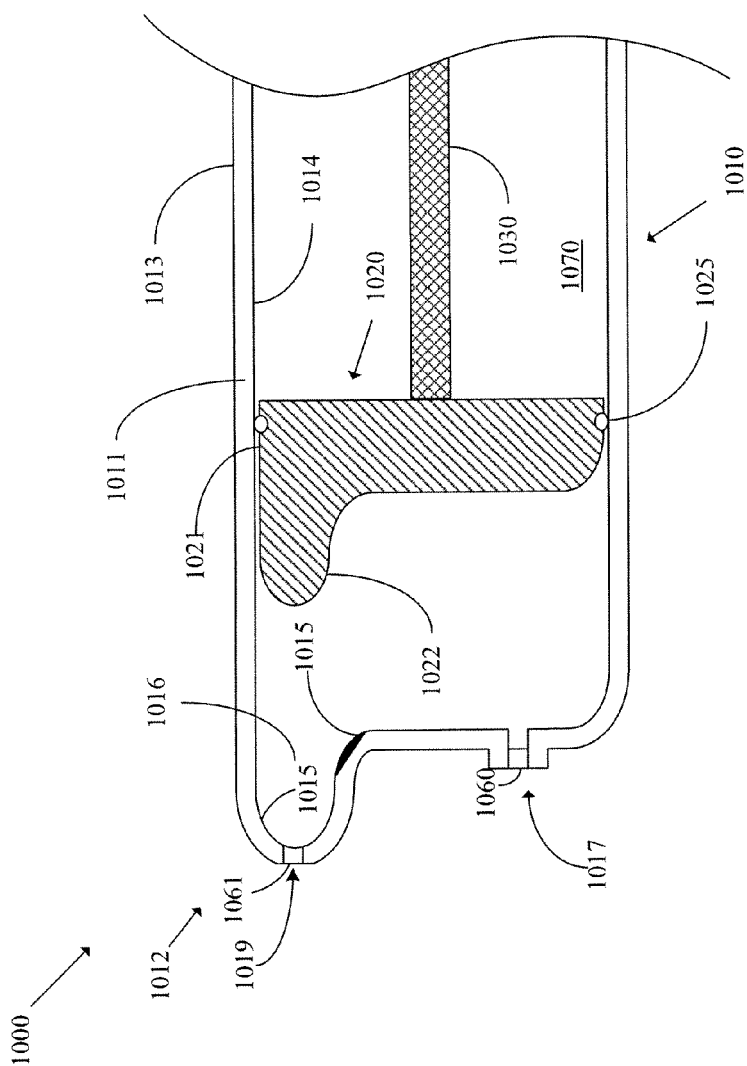
FIG. 15A illustrates a cross-sectional view of a system in accordance with an embodiment of the present invention.
Figure 16:
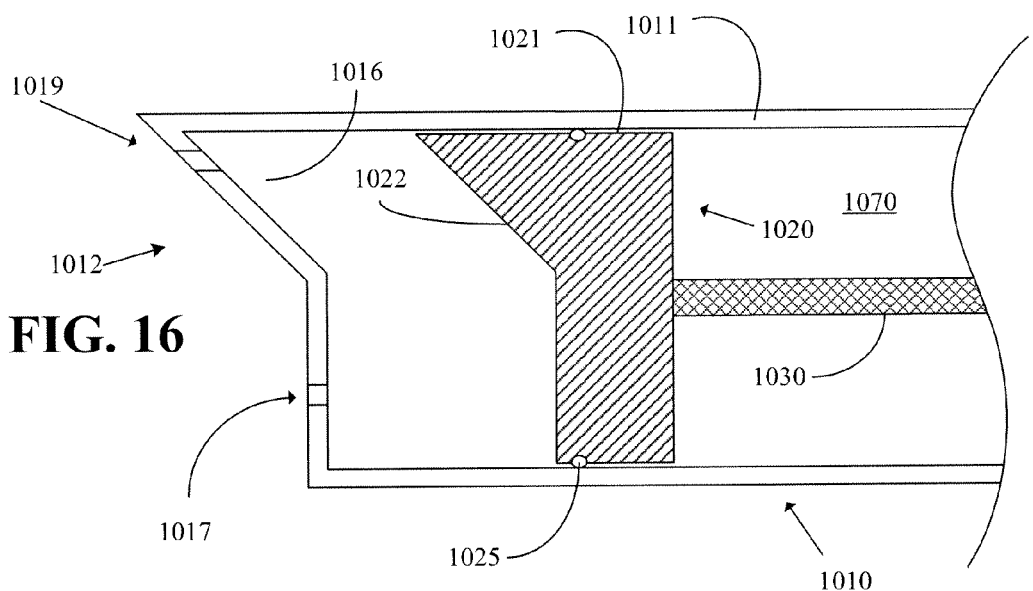
FIG. 16 illustrates a cross-sectional view of a system in accordance with an embodiment of the present invention.
Figure 17:
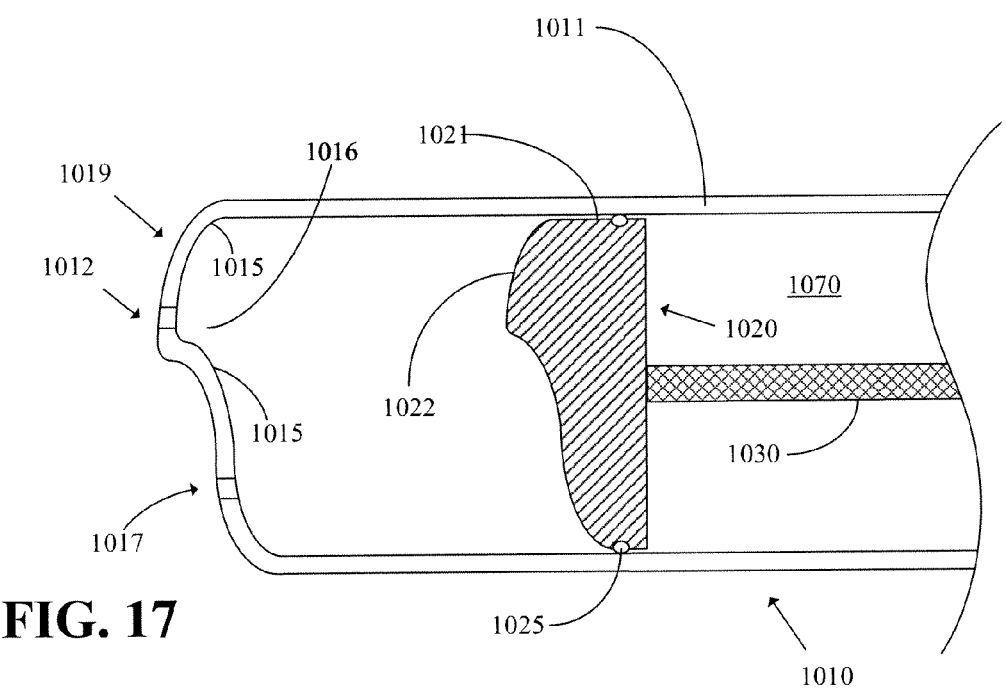
FIG. 17 illustrates a cross-sectional view of a system in accordance with an embodiment of the present invention.

FIG. 15A illustrates a cross-sectional view of a system 1000 in accordance with an embodiment of the present invention. FIGS. 16 and 17 illustrate cross-sectional views of exemplary (non-limiting) configurations and designs of the system 1000. With reference to FIG. 15A, the system 1000 includes a reservoir 1010, a plunger head 1020, and a plunger arm 1030. The reservoir 1010 includes a reservoir body portion 1011, a bubble trap portion 1012, a first port 1017, and a second port 1019. The reservoir 1010 has an outer surface 1013 and an inner surface 1014. The inner surface 1014 of the reservoir 1010 defines an interior volume 1070 of the reservoir 1010. The interior volume 1070 may be for containing fluidic media.

The first port 1017 of the reservoir 1010 may allow the fluidic media to be expelled from the interior volume 1070 of the reservoir 1010. The fluidic media may be expelled through the first port 1017 when a fluid connection is established with the interior volume 1070 through the first port 1017. In various embodiments, a septum 1060 is located in the first port 1017 of the reservoir 1000. The septum 1060 may be configured to be pierced by a needle (e.g., 650 in FIG. 13A) to establish the fluid connection out of the interior volume 1070 of the reservoir 1010. Examples of fluid connections are disclosed in, but not limited to, U.S. patent application Ser. No. 12/553,038, filed on Sep. 2, 2009 and patent application Ser. No. 12/336,367, filed on Dec. 16, 2008, all of which are herein incorporated by reference in their entirety.

The second port 1019 of the reservoir 1010 may allow for fluidic media to be received into the interior volume 1070 of the reservoir 1010. The fluidic media may be received through the second port 1019 when a fluid path is established with the interior volume 1070 through the second port 1019. In various embodiments, a septum 1061 is located in the second port 1019 of the reservoir 1000. The septum 1061, which may be similar to the septum 1060, may be configured to be pierced by a needle (e.g., 650 in FIG. 13A) to establish the fluid path into the interior volume 1070 of the reservoir 1010.

In various embodiments, the reservoir 1010 may be made of various suitable materials, including, but not limited to, glass, plastic, composite material, TOPAS® polymer (or any other cyclic olefin copolymer (or polymer)), or the like. The reservoir 1010 may be of any suitable shape, such as but not limited to, a cylinder shape, a tube shape, a barrel shape, a spherical shape, a shape with a rectangular cross-section, or the like, and/or size and may be adapted to hold any volume of fluidic media depending on needs of user-patients.

The plunger head 1020 is located within the reservoir 1010, and is moveable in an axial direction of the reservoir 1010, to expand or contract a volume of the reservoir 1010 in which fluidic media may be contained. The plunger head 1020 is connected to the plunger arm 1030, such that movement of the plunger arm 1030 in the axial direction of the reservoir 1010 causes movement of the plunger head 1020 in the axial direction of the reservoir 1010. The plunger head 1020 includes a plunger body portion 1021 and a plunger protruding portion 1022. The plunger head 1020 or a portion thereof may be made of Bromobutyl rubber, silicone rubber, or any other suitable material and/or any derivative thereof.

In various embodiments, the plunger head 1020 further includes one or more seals 1025 that surround a portion of the plunger body portion 1021. In various embodiments, the one or more seals 1025 may be made of any suitable material, such as but not limited to, rubber, plastic, composite material, or the like. The seals 1025 may be arranged in corresponding grooves (e.g., U6 in FIG. 7D) provided in the plunger body portion 1021. Examples of seals and arrangements thereof are disclosed in (but not limited to) U.S. patent application Ser. No. 12/417,976, filed Apr. 3, 2009 and U.S. patent application Ser. No. 12/533,942, filed Jul. 31, 2009, both of which are herein incorporated by reference in their entirety. In some embodiments, the plunger body portion 1021 may include one or more venting channels in communication with the groove. The venting channels may allow for gas in the groove to be vented. For instance, as fluidic media enters the reservoir, fluidic media may enter the venting channels to force out any air or other gas trapped in the groove. As with the other embodiments described in the disclosure, such embodiments help limit or reduce a presence of air bubbles in the fluidic medium. This is beneficial because it limits an amount of air bubbles that are later expelled from the reservoir into a patient or user, and thus helps to improve delivery accuracy when delivering a specified amount of the fluidic medium to a user.

The plunger head 1020 may be shaped such that a contour of the plunger head 1020 substantially matches or is substantially the same as an inner contour of the reservoir 1010. In various embodiments, the plunger body portion 1021 has a diameter that is slightly smaller than a diameter of the inner surface of the reservoir body portion 1011 of the reservoir 1010, such that the plunger head 1020 is able to slide within the reservoir 1010. In some embodiments, the seal 1025 on the plunger body portion 1021 is in contact with the inner surface of the reservoir body portion 1011 of the reservoir 1010 when the plunger head 1020 is within the reservoir 1010.

The plunge head 1020 has an axial dimension that corresponds to the axial dimension of the reservoir 1010 along which the plunger head 1020 moves. In particular embodiments, the plunger head 1020 is asymmetric about the axial dimension of plunger head 1020 (e.g., FIGS. 15A-17). In further embodiments, the plunger head 1020 is asymmetric about more than one dimension. For instance, the plunger head 1020 may be asymmetric about a width dimension (transverse the axial dimension) and/or thickness dimension (transverse the axial dimension and the width dimension).

In some embodiments, the plunger protruding portion 1022 is asymmetric about its axial dimension (e.g., FIGS. 16 and 17), which may be substantially parallel the axial dimension of the plunger head 1020. In further embodiments, the plunger protruding portion 1022 is asymmetric about more than one dimension. For instance, the plunger protruding portion 1022 may be asymmetric about a width dimension (transverse the axial dimension) and/or thickness dimension (transverse the axial dimension and the width dimension). In other embodiments, the plunger protruding portion 1022 is symmetric about its axis (e.g., FIGS. 15A-15B). In such embodiments, however, the plunger head 1020 is asymmetric about the axial dimension of the plunger head 1020.

The bubble trap portion 1012 of the reservoir 1010 is shaped to have a volume 1016 within an interior of the reservoir 1010, such that gas (e.g., air) bubbles in fluidic media may be trapped in the volume 1016 when the fluidic media is expelled from the reservoir 1010 through the first port 1017. The second port 1019 may be provided in the bubble trap portion 1012 to be in communication with the volume 1016. In various embodiments, an interior surface of the bubble trap portion 1012 is curved or angled near the second port 1017 so as to define the volume 1016. In particular embodiments, the second port 1019 is provided on the distal end of the bubble trap portion 1012. For instance, the second port 1019 may be provided at a location so that the second port 1019 is at the highest part of the reservoir 1010 when the reservoir 1010 is being filled with (and/or being dispensed of) fluidic media to allow air or the like to rise toward the second port 1019.

Thus, in various embodiments, the bubble trap portion 1012 is arranged so that when a user connects the reservoir 1010 to a vial of fluidic media to transfer fluidic media from the vial to the reservoir 1010, the bubble trap portion 1012 and the second port 1019 are positioned above the first port 1017 when held, for example, at about a 45-degree angle. As such, any gas (e.g., air) bubbles rise toward the bubble trap portion 1012 and the second port 1019. As fluid is expelled through the first port 1017, gas bubbles may continue to rise toward the bubble trap portion 1012 and the second port 1019. Gas collected or trapped in the bubble trap portion 1012 can then be expelled through the second port 1019.

Figure 18:
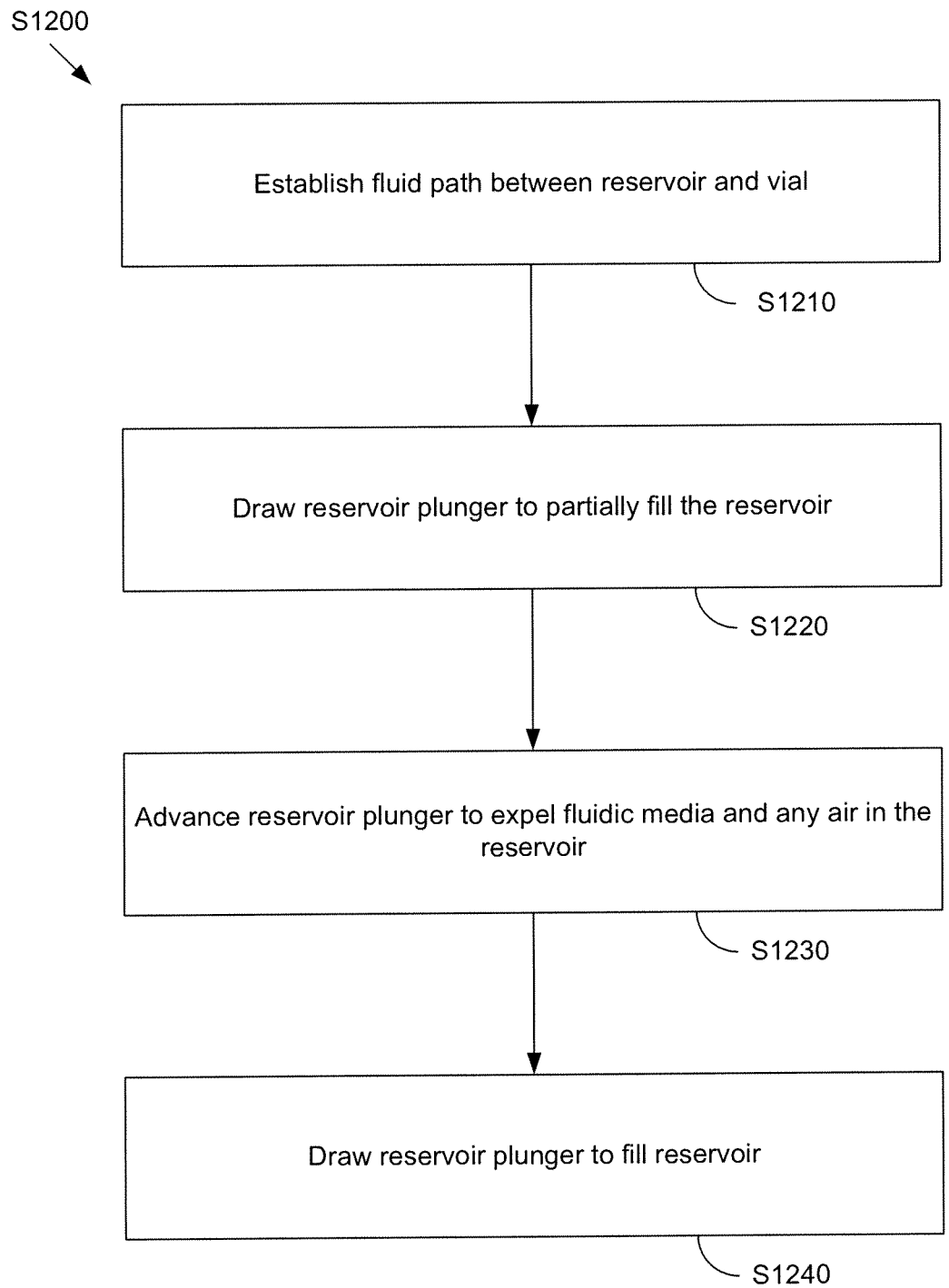
FIG. 18 illustrates a filling method in accordance with an embodiment of the present invention.

Examples of systems and methods for filling a reservoir from a vial or other source of fluidic media are disclosed in, but are not limited to, U.S. Pat. No. 6,453,956; U.S. patent application Ser. No. 12/537,579, filed on Aug. 7, 2009; and U.S. patent application Ser. No. 12/107,580, filed on Apr. 22, 2008, all of which are herein incorporated by reference in their entirety. Another example is shown in FIG. 18, discussed later.

Returning to FIGS. 15A, in various embodiments, the reservoir 1010 is shaped such that as the plunger head 1020 is advanced within the reservoir 1010, fluidic media is able to pass through the first port 1017 while gas bubbles in the reservoir 1010 collect in the volume 1016 defined by a curved or angled surface of the bubble trap portion 1012 of the reservoir 1010. Such geometry of the reservoir 1010 allows for decreasing an amount of gas bubbles that are delivered with fluidic media as compared with traditional reservoir geometries. In some embodiments, the bubble trap portion 1012 of the reservoir 1010 is curved outward from an interior volume defined by the reservoir body portion 1011 to collect gas bubbles, and fluidic media is able to pass directly from the interior volume defined by the reservoir body portion 1011 to the first port 1017.

In some embodiments, a surface 1015 of the reservoir 1010 may include a surface finish or material to prevent gas bubbles from substantially adhering to the surface 1015 and/or to direct gas bubbles (and/or fluidic media). The surface 1015, for instance, may be arranged between the bubble trap portion 1012 and the first port 1017. Thus, in various embodiments, the surface 1015 shunts gas bubbles in fluidic media away from the first port 1017 of the reservoir 510 and toward the volume 516 of the bubble trap portion 512 when fluidic media is being expelled from the interior volume 1070 of the reservoir body portion 511 of the reservoir 510. Alternatively, the surface 1015 may shunt fluidic media, but not the gas bubbles, toward the first port 1017. Accordingly, delivery accuracy may be able to be improved since a number of gas bubbles expelled from the reservoir 510 is further limited by the surface 1015. In various embodiments, such a surface finish or material includes a hydrophobic material, a hydrophilic material, or other suitable material for mitigating the amount of gas bubbles dispensed through the first port 1017. In some embodiments, the surface 1015 may be arranged in the bubble trap portion 1012 to shunt gas bubbles in fluidic media in the volume 1016 toward the second port 1019.

In various embodiments, the plunger head 1020 may be shaped such that a contour of the plunger head 1020 substantially matches or is substantially the same as an inner contour of the bubble trap portion 1012 of the reservoir 1010. In particular embodiments, the plunger protruding portion 1022 is shaped such that a contour of the plunger protruding portion 1022 substantially matches or is substantially the same as an inner contour of the bubble trap portion 1012 of the reservoir 1010. In some embodiments, the plunger protruding portion 1022 is curved and protrudes from the plunger body portion 1021. In various embodiments, the plunger protruding portion 1022 has a size that is slightly smaller than a region defined by the inner surface of the bubble trap portion 1012 of the reservoir 1010, such that the plunger protruding portion 1022 is able to slide within the volume 1016 of the reservoir 1010, and such that a space for a dead volume of gas (e.g., air) is left when the plunger head 1020 is fully advanced within the reservoir 1010. Thus, in various embodiments, the geometry of the reservoir 1010 and the plunger head 1020 allow for capturing gas bubbles in the volume 1016 of the bubble trap portion 1012 when fluidic media is being expelled from the first port 1017 of the reservoir 1010. In some embodiments, the plunger protruding portion 1022 includes a surface that is substantially parallel to the inner surface of the reservoir 1010.

In various embodiments, the plunger protruding portion 1022 has a size such that when the plunger head 1020 is fully advanced within the reservoir 1010, the plunger protruding portion 1022 substantially fills the volume 1016 of the bubble trap portion 1012. Also, in various embodiments, the plunger protruding portion 1022 fills less than all of the volume 1016 of the bubble trap portion 1012 when the plunger head 1020 is fully advanced within the reservoir 1010, so that one or more gas pockets for holding gas (e.g., air) exist between the plunger protruding portion 1222 and an inner surface of the bubble trap portion 1012, for example opposite the second port 1019, when the plunger head 1020 is fully advanced within the reservoir 1010. The plunger head 1020 may be fully advanced, for instance, when the plunger head 1020 cannot be advanced further in the reservoir 1010. In such an instance, the plunger head 1020 may be adjacent the first port 1017 to seal off the volume 1016 of the bubble trap portion 1012 from the first port 1017. In some embodiments, the plunger protruding portion 1022 extends at least partially into the volume 1016 of the bubble trap portion 1012 when the plunger head 1020 is sufficiently advanced within the reservoir 1010.

In various embodiments, the plunger protruding portion 1022 may be aligned with the volume 1016 of the bubble trap portion 1012 (e.g., the axis of the plunger protruding portion is aligned with the volume 1016) so that movement of the plunger 1020 in the axial direction of the reservoir 1010 causes the plunger protruding portion 1022 to move into the volume 1016 of the bubble trap portion 1012. In particular embodiments, the plunger protruding portion 1022 may be aligned with the second port 1019 e.g., the axis of the plunger protruding portion is aligned with the second port 1019).

Figure 15B:
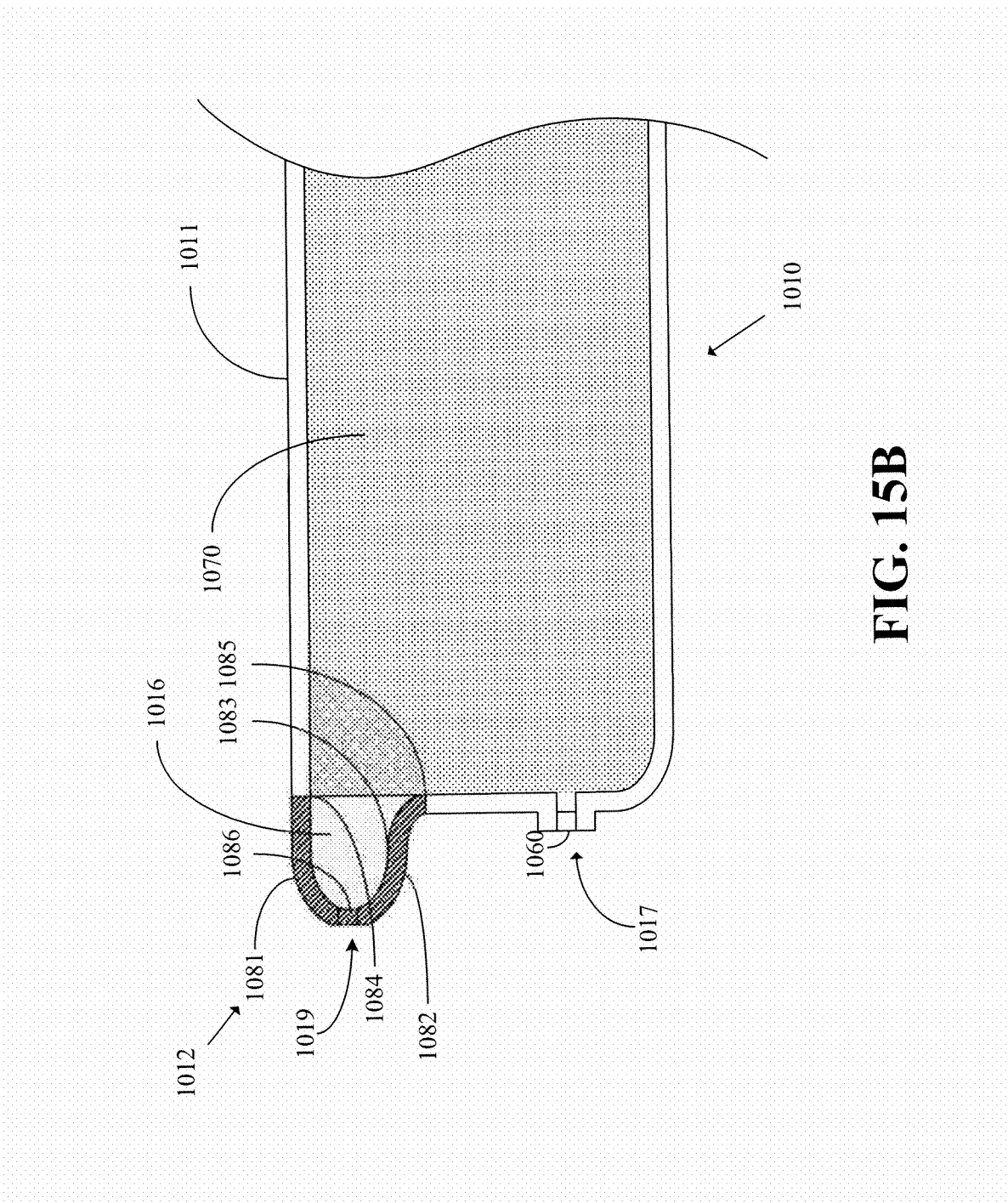
FIG. 15B illustrates a cross-sectional view of a reservoir in accordance with an embodiment of the present invention.

FIG. 15B illustrates a cross-sectional view of the reservoir 1010 in accordance with an embodiment of the present invention. FIG. 15B is shaded to highlight various features of the reservoir 210. With reference to FIGS. 15A and 15B, the reservoir 1010 includes the reservoir body portion 1011, the bubble trap portion 1012, the first port 1017, and the second port 1019. The reservoir body portion 1011 defines the interior volume 1070 for containing fluidic media. The first port 1017 is in fluid flow communication with the interior volume 1070 of the reservoir body portion 1011. The bubble trap portion 1012 has the volume 1016 in fluid flow communication with the interior volume 1070 of the reservoir body portion 1011 for trapping gas bubbles that are in the fluidic media as the fluidic media is being expelled from the interior volume 1070. The second port 1019 is in fluid flow communication with the interior volume 1070 of the reservoir body portion 1011.

In various embodiments, the first port 1017 and the second port 1019 are located to a particular end of the interior volume 1070 (e.g., the left end in the orientation shown in FIG. 15B), and the bubble trap portion 1012 is located to the particular end of the interior volume 1070. In further embodiments, the second port 1019 and the volume 1016 are located to a particular side of the interior volume 270 (e.g., the top side in the orientation shown in FIG. 15B).

Also, in various embodiments, the bubble trap portion 1012 has a first portion 1081 that extends from the reservoir body portion 1011 away from the interior volume 1070, and a second portion 1082 that returns back toward the interior volume 1070. In some embodiments, the reservoir body portion 1011 and the bubble trap portion 1012 are formed together as a single seamless unit. Also, in some embodiments, the first portion 1081 of the bubble trap portion 1012 extends from the reservoir body portion 1011 away from the interior volume 1070 and the second portion 1082 of the bubble trap portion 1012 extends from the first portion 1081 toward the interior volume 1070.

In various embodiments, the bubble trap portion 1012 includes a curved surface 1083 having a first end region 1084, a second end region 1085, and a middle region 1086 between the first end region 1084 and the second end region 1085. In some embodiments, the first end region 1084 and the second end region 1085 are closer to the interior volume 1070 of the reservoir body portion 1011 than the middle region 1086 is to the interior volume 1070. Also, in some embodiments, the first end region 1084 is in contact with the reservoir body portion 1011, and the second end region 1085 is located adjacent to the interior volume 1070 of the reservoir body portion 1011. In some embodiments, the middle portion 1086 may correspond to a location where the second port 1019 is provided.

In various embodiments, the curved surface 1083 of the bubble trap portion 1012 is in contact with the fluidic media when the fluidic media is in the volume 1016 of the bubble trap portion 1012. In further embodiments, the curved surface 1083 is shaped to receive at least a portion of the plunger head 1020. For instance, in embodiments where the plunger head 1020 (or the plunger protruding portion 1022) is dome-shaped, the curved surface 1083 is contoured to match the dome shape of the plunger head 1020.

The plunger head 1020 has an axial dimension that corresponds to the axial dimension of the reservoir 1010 along which the plunger head 1020 moves. In particular embodiments, the reservoir 1010 is asymmetric about its axis (e.g., FIGS. 15A-17). In further embodiments, the reservoir 1010 is asymmetric about more than one dimension. For instance, the reservoir 1010 may be asymmetric about its width dimension (transverse the axial dimension) and/or thickness dimension (transverse the axial dimension and the width dimension).

In some embodiments, the bubble trap portion 1012 has an axial dimension along which the plunger protruding portion 1022 travels as the plunger head 1020 is moved along the axial dimension of the reservoir 1010. In particular embodiments, the bubble trap portion 1012 is asymmetric about the axial dimension of the bubble trap portion 1012 (e.g., FIGS. 16 and 17). In further embodiments, the bubble trap portion 1012 is asymmetric about more than one dimension. For instance, the bubble trap portion 1012 may be asymmetric about a width dimension (transverse the axial dimension) and/or thickness dimension (transverse the axial dimension and the width dimension). In other embodiments, the bubble trap portion 1012 is symmetric about the axial dimension of the bubble trap portion 1012 (e.g., FIGS. 15A-15B). In such embodiments, however, the reservoir 1010 is asymmetric about the axial dimension of the reservoir 1010.

In various embodiments, the reservoir 1010 is shaped such that in order for fluidic media to flow from the volume 1016 of the bubble trap 10212 to the first port 1017, the fluidic media must flow through the interior volume 1070 of the reservoir body portion 1011. In some embodiments, the reservoir 1010 includes a channel that leads from the interior volume 1070 of the reservoir body portion 1011 to the second port 1019, and the bubble trap portion 1012 (and/or the volume 1016) encircles at least a portion of the channel.

In various embodiments, for example as shown in FIG. 16, the bubble trap portion 1012 includes a first surface that defines an edge of the volume 1016 of the bubble trap portion 1012, and a second surface that defines another edge of the volume 1016 of the bubble trap portion 1012, where the second surface is positioned at an angle with respect to the first surface. In some embodiments, the angle between the first surface and the second surface is less than 90 degrees. Also, in some embodiments, the first surface is planar with respect to an inner surface of the reservoir body portion 1011 of the reservoir 1010. In various embodiments, edges may be rounded to facilitate shuttling of gas bubbles into the volume 1016 from the interior volume 1070 and/or out of the second port 1019 from the volume 1016.

In various embodiments, the plunger protruding portion 1022 may comprise a shape of one of the protruding portions 122, 222, 322, 422, 522, 622, 822, or the like discussed with respect to FIGS. 7A, 7B, 9A, 10A, 11A, 12A, 13A, 13B, 14A, and 14B. For instance, the plunger protruding portion 1022 may have a U-shaped cross-section (such that the cross-section has two portions extending toward the volume 1016 of the bubble trap portion 1012). As such, a plunger head with a plunger protruding portion having a U-shaped cross-section may be asymmetric about the axis of the plunger head. Thus, some embodiments the plunger head 1020 may include a portion (e.g., 623 in FIG. 13A), recess (e.g., 523 in FIG. 12C; 828 in FIG. 14B) or the like for receiving a needle (e.g., 550 in FIG. 12C; 650 in FIG. 13A; 850 in FIG. 14B) when establishing a fluid path. In other embodiments, the plunger head 1020 may include additional cavities (e.g., 624 in FIG. 13A; 824 in FIG. 14A) for trapping gas bubbles. In various embodiments, the bubble trap portion 1012 may comprise a shape of one of the bubble trap portions 212, 312, 412, 512, 612, 812, or the like discussed with respect to FIGS. 9A, 10A, 11A, 12A, 13A, 13B, 14A, and 14B.

Referring to FIGS. 15A-17, various embodiments relate to a plunger head having an asymmetrical shape that mates with an asymmetrical cup shape or corresponding contour on an interior end of a reservoir. In particular, embodiments, the asymmetrical cup shape or corresponding contour bulges outward on a fill port side of the reservoir to trap bubbles near the fill port. Thus various embodiments help limit or reduce a presence of air (or other gas) bubbles in the fluidic medium. This is beneficial because it limits an amount of air bubbles that are later expelled from the reservoir into a patient or user, and thus helps to improve delivery accuracy when delivering a specified amount of the fluidic medium to a user.

FIG. 18 illustrates a method 1200 for filling a reservoir having any number of ports, and thus may be used with (but not limited to) any of the systems (e.g., 100, 200, 300, 400, 500, 600, 800, 1000 in FIGS. 7A-17) discussed in the disclosure. In step S1210, a fluid path may be established between the reservoir and a vial of fluidic media. The fluid path may be a needle connecting the vial and the reservoir. Then in step S1220, a plunger in the reservoir may be drawn to create a vacuum in the reservoir to draw in the fluidic media from the vial. In particular embodiments, the plunger may be drawn to partially (but not completely) fill the reservoir. For instance, the plunger may be drawn to draw in about half of the total fluidic media. As this fluidic media is drawn into the reservoir, any air (or other gas) present in the needle (or other fluid path) prior to filling is also drawn into the reservoir. Then, in step S1230, the plunger may be fully advanced to expel all of the fluidic media and air that is in the reservoir (e.g., as drawn in in step S1220) back through the needle into the vial. In other embodiments, the fluidic media and air that is in the reservoir (e.g., as drawn in in step S1220) may be expelled into a different fluid collection source, for instance, through a second needle or the like. During step S1230, the end of the needle arranged in the vial should be submerged in the fluidic media of the vial to prevent air from reentering the needle. As a result of step S1230, the reservoir and the needle are devoid of air (primed). In step S1240, the plunger in the reservoir may be drawn to fill the reservoir. As with the other embodiments described in the disclosure, such embodiments help limit or reduce a presence of air bubbles in the fluidic medium. This is beneficial because it limits an amount of air bubbles that are later expelled from the reservoir into a patient or user, and thus helps to improve delivery accuracy when delivering a specified amount of the fluidic medium to a user.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A reservoir having an axis and a plunger head moveable along the axis within the reservoir to transfer fluidic media, the reservoir comprising:
   a reservoir body portion having a wall defining an interior volume, the interior volume for containing the fluidic media, the reservoir having a first port in the reservoir body portion to be in fluid flow communication with the interior volume of the reservoir body portion, the first port for expelling fluidic media from the interior volume of the reservoir body portion as the plunger is moved within the reservoir; and
   a collecting portion having a wall defining a volume in fluid flow communication with the interior volume of the reservoir body portion, the volume of the collecting portion for collecting gas bubbles in the fluidic media as the fluidic media is expelled through the first port from the interior volume of the reservoir body portion, the reservoir having a second port in the collecting portion to be in fluid flow communication with the volume of the collecting portion, the second port for receiving fluidic media into the reservoir;
   the plunger head having a shape that is asymmetric about the axis of the reservoir and comprising a body portion and a protruding portion, the protruding portion of the plunger head extending toward the collecting portion of the reservoir;
   wherein the volume of the collecting portion has a size such that when the plunger head is fully advanced within the reservoir, the protruding portion extends into the volume of the collecting portion.

2. The reservoir of claim 1, wherein the first port and the second port are located to a same side of the interior volume of reservoir body portion.

3. The reservoir of claim 1,
   the reservoir having an axis along which the plunger head moves to expel fluidic media from the interior volume of the reservoir body portion through the first port;
   wherein the reservoir is shaped to be asymmetric about its axis.

4. The reservoir of claim 1, wherein the second port is arranged further from the interior volume of the reservoir body portion than the first port.

5. The reservoir of claim 1, the reservoir having a channel leading from the interior volume of the reservoir body portion to the first port of the reservoir.

6. A reservoir having a plunger head moveable within the reservoir to transfer fluidic media, the reservoir comprising:
   a reservoir body portion having a wall defining an interior volume, the interior volume for containing the fluidic media, the reservoir having a first port in the reservoir body portion to be in fluid flow communication with the interior volume of the reservoir body portion, the first port for expelling fluidic media from the interior volume of the reservoir body portion as the plunger is moved within the reservoir; and
   a collecting portion having a wall defining a volume in fluid flow communication with the interior volume of the reservoir body portion, the volume of the collecting portion for collecting gas bubbles in the fluidic media as the fluidic media is expelled through the first port from the interior volume of the reservoir body portion, the reservoir having a second port in the collecting portion to be in fluid flow communication with the volume of the collecting portion, the second port for receiving fluidic media into the reservoir;
   a channel leading from the interior volume of the reservoir body portion to the first port of the reservoir;
   wherein at least a portion of the reservoir is arranged between the channel and the volume of the collecting portion.

7. A reservoir having a plunger head moveable within the reservoir to transfer fluidic media, the reservoir comprising:
   a reservoir body portion having a wall defining an interior volume, the interior volume for containing the fluidic media, the reservoir having a first port in the reservoir body portion to be in fluid flow communication with the interior volume of the reservoir body portion, the first port for expelling fluidic media from the interior volume of the reservoir body portion as the plunger is moved within the reservoir; and
   a collecting portion having a wall defining a volume in fluid flow communication with the interior volume of the reservoir body portion, the volume of the collecting portion for collecting gas bubbles in the fluidic media as the fluidic media is expelled through the first port from the interior volume of the reservoir body portion, the reservoir having a second port in the collecting portion to be in fluid flow communication with the volume of the collecting portion, the second port for receiving fluidic media into the reservoir;

the reservoir having a channel leading from the interior volume of the reservoir body portion to the second port of the reservoir; wherein the volume of the collection portion surrounds the channel.

8. The reservoir of claim 1, the reservoir body portion having a length dimension extending from a rear end of the reservoir body portion to a front end of the reservoir body portion, the first port arranged on the front end of the reservoir body portion;

the reservoir having a length dimension extending from the rear end of the reservoir body portion to a front end of the collecting portion, the second port arranged on the front end of the collecting portion;

wherein the length dimension of the reservoir is greater than the length dimension of the reservoir body.

9. The reservoir of claim 1, wherein the collecting portion protrudes from the reservoir body portion.

10. The reservoir of claim 1, wherein the second port is for expelling gas collected in the volume of the collecting portion.

11. The reservoir of claim 1, the reservoir shaped such that in order for the fluidic media to flow from the volume of the collecting portion to the first port of the reservoir, the fluidic media must flow through the interior volume of the reservoir body portion.

12. The reservoir of claim 1, the collecting portion having a first portion that extends from the reservoir body portion away from the interior volume of the reservoir body portion, and a second portion that returns toward the interior volume of the reservoir body portion.

13. The reservoir of claim 1, the collecting portion having a first portion that extends from the reservoir body portion away from the interior volume of the reservoir body portion, and a second portion that extends from the first portion toward the interior volume of the reservoir body portion.

14. A reservoir having a plunger head moveable within the reservoir to transfer fluidic media, the reservoir comprising:

a reservoir body portion having a wall defining an interior volume, the interior volume for containing the fluidic media, the reservoir having a first port in the reservoir body portion to be in fluid flow communication with the interior volume of the reservoir body portion, the first port for expelling fluidic media from the interior volume of the reservoir body portion as the plunger is moved within the reservoir; and a collecting portion having a wall defining a volume in fluid flow communication with the interior volume of the reservoir body portion, the volume of the collecting portion for collecting gas bubbles in the fluidic media as the fluidic media is expelled through the first port from the interior volume of the reservoir body portion, the reservoir having a second port in the collecting portion to be in fluid flow communication with the volume of the collecting portion, the second port for receiving fluidic media into the reservoir;

the wall of the collecting portion comprising a curved surface, the curved surface having a first end region, a second end region, and a middle region between the first end region and the second end region, the first end region and the second end region extending from the middle region toward the interior volume of the reservoir body portion such that the first end region and the second end region are located closer to the interior volume of the reservoir body portion than the middle region is to the interior volume of the reservoir body portion.

15. The reservoir of claim 14, wherein the second port is arranged in the middle region.

16. The reservoir of claim 14, wherein the first end region is in contact with the wall of the reservoir body portion; and wherein the second end region is located adjacent the interior volume of the reservoir body portion.

17. The reservoir of claim 1, the reservoir further comprising:

at least one of a surface treatment and a material on at least a portion of a surface of the wall of the collecting portion that causes the at least a portion of the surface to be hydrophobic.

18. The reservoir of claim 1, the reservoir further comprising:

at least one of a surface treatment and a material on at least a portion of a surface of the wall of the collecting portion that causes the at least a portion of the surface to be hydrophilic.

19. The reservoir of claim 1, the reservoir further comprising:

at least one of a first surface treatment and a first material on at least a first portion of the wall of the collecting portion that causes the at least a first portion to be hydrophobic; and at least one of a second surface treatment and a second material on at least a second portion of the wall of the collecting portion that causes the at least a second portion to be hydrophilic.

20. The reservoir of claim 19, wherein the at least a second portion of the wall of the collecting portion is located closer to the interior volume of the reservoir body portion than the at least a first portion is to the interior volume of the reservoir body portion.

21. A method of manufacturing a reservoir having an axial dimension and a plunger head moveable along the axial dimension within the reservoir to transfer fluidic media, the method comprising:

providing a reservoir body portion having a wall defining an interior volume, the interior volume for containing the fluidic media, the reservoir having a first port in the reservoir body portion to be in fluid flow communication with the interior volume of the reservoir body portion, the first port for expelling fluidic media from the interior volume of the reservoir body portion as the plunger is moved within the reservoir;

providing a collecting portion having a wall defining a volume in fluid flow communication with the interior volume of the reservoir body portion, the volume of the collecting portion for collecting gas bubbles in the fluidic media as the fluidic media is expelled through the first port from the interior volume of the reservoir body portion, the reservoir having a second port in the collecting portion to be in fluid flow communication with the volume of the collecting portion, the second port for receiving fluidic media into the reservoir; and arranging the plunger head within the interior volume of the reservoir body for movement in the axial dimension of the reservoir, the plunger head having a shape that is asymmetric about the axial dimension of the reservoir and comprising a body portion and a protruding portion, the protruding portion of the plunger head extending toward the collecting portion of the reservoir;

wherein the volume of the collecting portion has a size such that when the plunger head is fully advanced within the reservoir, the protruding portion extends into the volume of the collecting portion.

22. A system for transferring fluidic media, the system comprising:
   a plunger head; and
   a reservoir, the reservoir comprising:
      a reservoir body portion having a wall defining an interior volume, the interior volume for containing the fluidic media, the reservoir having a first port in the reservoir body portion to be in fluid flow communication with the interior volume of the reservoir body portion, the first port for expelling fluidic media from the interior volume of the reservoir body portion as the plunger is moved within the reservoir; and
      a collecting portion having a wall defining a volume in fluid flow communication with the interior volume of the reservoir body portion, the volume of the collecting portion for collecting gas bubbles in the fluidic media as the fluidic media is expelled through the first port from the interior volume of the reservoir body portion, the reservoir having a second port in the collecting portion to be in fluid flow communication with the volume of the collecting portion, the second port for receiving fluidic media into the reservoir;
   the plunger head moveable with the reservoir along a length dimension of the reservoir body portion to expel the fluidic media through the first port from the interior volume of the reservoir body portion; and
   the reservoir having an axis along which the plunger head moves to expel fluidic media from the interior volume of the reservoir body portion through the first port;
   wherein the plunger head is shaped to be asymmetric about the axis of the reservoir.

23. The system of claim 22, the plunger head having a contour that substantially matches an inner contour of the wall of the collecting portion.

24. A system of claim 22, for transferring fluidic media, the system comprising:
   a plunger head; and
   a reservoir, the reservoir comprising:
      a reservoir body portion having a wall defining an interior volume, the interior volume for containing the fluidic media, the reservoir having a first port in the reservoir body portion to be in fluid flow communication with the interior volume of the reservoir body portion, the first port for expelling fluidic media from the interior volume of the reservoir body portion as the plunger is moved within the reservoir; and
      a collecting portion having a wall defining a volume in fluid flow communication with the interior volume of the reservoir body portion, the volume of the collecting portion for collecting gas bubbles in the fluidic media as the fluidic media is expelled through the first port from the interior volume of the reservoir body portion, the reservoir having a second port in the collecting portion to be in fluid flow communication with the volume of the collecting portion, the second port for receiving fluidic media into the reservoir;
   the plunger head moveable with the reservoir along a length dimension of the reservoir body portion to expel the fluidic media through the first port from the interior volume of the reservoir body portion; and
   the plunger head having a first side and a second side opposite the first side, the first side having a length dimension, the second side having a length dimension greater than the length dimension of the first side.

25. The system of claim 22, the plunger head comprising a body portion and a protruding portion, the protruding portion extending toward the collecting portion.

26. The system of claim 25, the protruding portion having a contour that substantially matches an inner contour of the wall of the collecting portion.

27. A system for transferring fluidic media, the system comprising:
   a plunger head; and
   a reservoir, the reservoir comprising:
      a reservoir body portion having a wall defining an interior volume, the interior volume for containing the fluidic media, the reservoir having a first port in the reservoir body portion to be in fluid flow communication with the interior volume of the reservoir body portion, the first port for expelling fluidic media from the interior volume of the reservoir body portion as the plunger is moved within the reservoir; and
      a collecting portion having a wall defining a volume in fluid flow communication with the interior volume of the reservoir body portion, the volume of the collecting portion for collecting gas bubbles in the fluidic media as the fluidic media is expelled through the first port from the interior volume of the reservoir body portion, the reservoir having a second port in the collecting portion to be in fluid flow communication with the volume of the collecting portion, the second port for receiving fluidic media into the reservoir;
   the plunger head moveable with the reservoir along a length dimension of the reservoir body portion to expel the fluidic media through the first port from the interior volume of the reservoir body portion;
   the plunger head comprising a body portion and a protruding portion, the protruding portion extending toward the collecting portion; and
   the protruding portion arranged to be aligned with the second port in a direction parallel to the length dimension of the reservoir body portion.

28. The system of claim 25, wherein the protruding portion is wedge shaped so as to direct gas in the fluidic media in the interior volume of the reservoir body portion into the volume of the collecting portion.

29. A system for transferring fluidic media, the system comprising:
   a plunger head; and
   a reservoir, the reservoir comprising:
      a reservoir body portion having a wall defining an interior volume, the interior volume for containing the fluidic media, the reservoir having a first port in the reservoir body portion to be in fluid flow communication with the interior volume of the reservoir body portion, the first port for expelling fluidic media from the interior volume of the reservoir body portion as the plunger is moved within the reservoir; and
      a collecting portion having a wall defining a volume in fluid flow communication with the interior volume of the reservoir body portion, the volume of the collecting portion for collecting gas bubbles in the fluidic media as the fluidic media is expelled through the first port from the interior volume of the reservoir body portion, the reservoir having a second port in the collecting portion to be in fluid flow communication with the volume of the collecting portion, the second port for receiving fluidic media into the reservoir;

the plunger head moveable with the reservoir along a length dimension of the reservoir body portion to expel the fluidic media through the first port from the interior volume of the reservoir body portion;

the plunger head comprising a body portion and a protruding portion, the protruding portion extending toward the collecting portion; and wherein the protruding portion of the plunger has a concavity for collecting gas bubbles as the fluidic media is expelled through the first port.

30. A system for transferring fluidic media, the system comprising:

a plunger head; and a reservoir, the reservoir comprising:

a reservoir body portion having a wall defining an interior volume, the interior volume for containing the fluidic media, the reservoir having a first port in the reservoir body portion to be in fluid flow communication with the interior volume of the reservoir body portion, the first port for expelling fluidic media from the interior volume of the reservoir body portion as the plunger is moved within the reservoir; and a collecting portion having a wall defining a volume in fluid flow communication with the interior volume of the reservoir body portion, the volume of the collecting portion for collecting gas bubbles in the fluidic media as the fluidic media is expelled through the first port from the interior volume of the reservoir body portion, the reservoir having a second port in the collecting portion to be in fluid flow communication with the volume of the collecting portion, the second port for receiving fluidic media into the reservoir;

the plunger head moveable with the reservoir along a length dimension of the reservoir body portion to expel the fluidic media through the first port from the interior volume of the reservoir body portion;

the plunger head comprising a body portion and a protruding portion, the protruding portion extending toward the collecting portion; and wherein the protruding portion has a size such that when the plunger head is fully advanced within the reservoir, the protruding portion substantially fills the volume of the collecting portion.

31. The system of claim 25, wherein the protruding portion is shaped such that the protruding portion fills less than all of the volume of the collecting portion when the plunger head is fully advanced within the reservoir, so that one or more pockets of gas exist between the protruding portion and an inner surface of the wall of the collecting portion when the plunger head is fully advanced within the reservoir.

32. The system of claim 25, the protruding portion positioned and shaped such that the protruding portion extends at least partially into the volume of the collecting portion when the plunger head is sufficiently advanced within the reservoir.

33. The system of claim 22, the system further comprising:

at least one of a surface treatment and a material on at least a portion of a surface of the plunger head that causes the at least a portion of the surface to be hydrophobic.

34. The system of claim 22, the system further comprising:

at least one of a surface treatment and a material on at least a portion of a surface of the plunger head that causes the at least a portion of the surface to be hydrophilic.

35. The system of claim 22, the plunger head comprising a seal member arranged to provide a seal between the plunger head and the wall of the reservoir body portion.

36. A system for transferring fluidic media, the system comprising:

a plunger head; and a reservoir, the reservoir comprising:

a reservoir body portion having a wall defining an interior volume, the interior volume for containing the fluidic media, the reservoir having a first port in the reservoir body portion to be in fluid flow communication with the interior volume of the reservoir body portion, the first port for expelling fluidic media from the interior volume of the reservoir body portion as the plunger is moved within the reservoir; and a collecting portion having a wall defining a volume in fluid flow communication with the interior volume of the reservoir body portion, the volume of the collecting portion for collecting gas bubbles in the fluidic media as the fluidic media is expelled through the first port from the interior volume of the reservoir body portion, the reservoir having a second port in the collecting portion to be in fluid flow communication with the volume of the collecting portion, the second port for receiving fluidic media into the reservoir;

the plunger head moveable with the reservoir along a length dimension of the reservoir body portion to expel the fluidic media through the first port from the interior volume of the reservoir body portion;

the plunger head comprising a seal member arranged to provide a seal between the plunger head and the wall of the reservoir body portion; and the plunger head having a recess for receiving the seal member, the plunger head having a channel from the recess to the interior volume of the reservoir body portion through which fluidic media may enter the recess from the interior volume of the reservoir body portion.

37. A method of manufacturing a system for transferring fluidic media, the method comprising:

providing a plunger head; and providing a reservoir, the reservoir comprising:

a reservoir body portion having a wall defining an interior volume, the interior volume for containing the fluidic media, the reservoir having a first port in the reservoir body portion to be in fluid flow communication with the interior volume of the reservoir body portion, the first port for expelling fluidic media from the interior volume of the reservoir body portion as the plunger is moved within the reservoir; and a collecting portion having a wall defining a volume in fluid flow communication with the interior volume of the reservoir body portion, the volume of the collecting portion for collecting gas bubbles in the fluidic media as the fluidic media is expelled through the first port from the interior volume of the reservoir body portion, the reservoir having a second port in the collecting portion to be in fluid flow communication with the volume of the collecting portion, the second port for receiving fluidic media into the reservoir;

the plunger head moveable with the reservoir along a length dimension of the reservoir body portion to expel the fluidic media through the first port from the interior volume of the reservoir body portion; and the reservoir having an axis along which the plunger head moves to expel fluidic media from the interior volume of the reservoir body portion through the first port;

wherein the plunger head is shaped to be asymmetric about the axis of the reservoir.

38. A reservoir system comprising a plunger head and a reservoir, the plunger head moveable along an axial dimension of the reservoir to expel fluidic media from an interior volume of the reservoir through a port of the reservoir; wherein the plunger head is asymmetric about the axial dimension of the reservoir, the plunger head comprising at least one of a surface treatment and a material on at least a portion of a surface of the plunger head that causes the at least a portion of the surface to be one of hydrophobic or hydrophilic.

39. The plunger head of claim 38,
the plunger head having an axial dimension;
wherein the plunger head is asymmetric about the axial dimension of the plunger head.

40. The plunger head of claim 38, the plunger head having a contour that substantially matches an inner contour of the reservoir.

41. The plunger head of claim 38, the plunger head having a first side and a second side opposite the first side, the first side having a length dimension parallel the axial dimension of the reservoir, the second side having a length dimension parallel the axial dimension of the reservoir, the length dimension of the second side greater than the length dimension of the first side.

42. The plunger head of claim 38, the plunger head comprising a body portion and a protruding portion, the protruding portion extending from the body portion along the axial dimension of the reservoir in a direction of movement that the plunger moves to expel fluidic media from the reservoir.

43. The plunger head of claim 42, wherein the protruding portion of the plunger has a concavity for collecting gas bubbles from the reservoir.

44. The plunger head of claim 42, wherein as the plunger head is moved in the reservoir, the protruding portion is aligned with a second port of the reservoir through which fluidic media is received into the reservoir in a direction parallel to the axial dimension of the reservoir.

45. The plunger head of claim 44, wherein as the plunger head is moved in the reservoir, the protruding portion is not aligned with the port of the reservoir through which fluidic media is expelled from the reservoir in a direction parallel to the axial dimension of the reservoir.

46. The plunger head of claim 44, the plunger head comprising a seal member arranged to provide a seal between the plunger head and the reservoir.

47. The plunger head of claim 46, the plunger head having a recess for receiving the seal member, the plunger head having a channel from the recess to the interior volume of the reservoir through which fluidic media may enter the recess from the interior volume of the reservoir.

* * * * *